US008119633B2

(12) United States Patent
Merla et al.

(10) Patent No.: US 8,119,633 B2
(45) Date of Patent: Feb. 21, 2012

(54) SUBSTITUTED SULFONAMIDE COMPOUNDS

(75) Inventors: Beatrix Merla, Aachen (DE); Stefan Oberboersch, Aachen (DE); Melanie Reich, Aachen (DE); Bernd Sundermann, Friedrichsdorf (DE); Werner Englberger, Stolberg (DE); Timo Struenker, Cologne (DE); Ruth Jostock, Stolberg (DE); Sabine Hees, Aachen (DE); Edward Bijsterveld, Nijmegen (NL); Fritz Theil, Berlin (DE); Heinz Graubaum, Berlin (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/112,592

(22) Filed: Apr. 30, 2008

(65) Prior Publication Data
US 2008/0312231 A1 Dec. 18, 2008

(30) Foreign Application Priority Data

Apr. 30, 2007 (DE) .................... 10 2007 020 492

(51) Int. Cl.
A61K 31/5377 (2006.01)
A61K 31/192 (2006.01)
A61K 31/495 (2006.01)
A61P 25/00 (2006.01)
A61P 25/24 (2006.01)
A61P 3/04 (2006.01)
A61P 25/06 (2006.01)
A61P 3/10 (2006.01)
C07D 241/04 (2006.01)
C07D 413/02 (2006.01)

(52) U.S. Cl. ............. 514/234.8; 514/255.01; 514/562; 544/383; 544/119; 562/432

(58) Field of Classification Search .................. None
See application file for complete search history.

(56) References Cited

U.S. PATENT DOCUMENTS
6,319,920 B1 * 11/2001 Caroon et al. ............. 514/235.5

FOREIGN PATENT DOCUMENTS
JP   2001172257 A  *  6/2001
WO  WO 2004/092164 A1  10/2004
WO  WO 2007/115821 A2  10/2007

OTHER PUBLICATIONS

Sara H. Bengtson, et al, "Kinin Receptor Expression during Staphylococcus aureus Infection", Blood, Sep. 15, 2006, pp. 2055-2063, vol. 108, No. 6, The American Society of Hematology, Washington, DC, USA.

Gabra et al., The kinin system mediates hyperalgesia through the inducible bradykinin B1 receptor subtype: evidence in various experimental animal models of type 1 and type 2 diabetic neuropathy, Biol. Chem. vol. 387, pp. 127-143, Feb. 2006.
Joao B. Calixto, et al., "Kinin $B_1$ Receptors: Key G-Protein-Coupled Receptors and their Role in Inflammatory and Painful Processes", British Journal of Pharmacology, 2004, pp. 803-818, vol. 143, Nature Publishing Group.
R. Hayashi et al., "Bradykinin Stimulates IL-6 and IL-8 Production by Human Lung Fibroblasts through ERK- and p38 MAPK-dependent Mechanisms", European Respiratory Journal, 2000, pp. 452-458, vol. 16, ERS Journals Ltd.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
Hess et al., Generation and characterization of a humanized bradykinin B1 receptor mouse, Biol. Chem., vol. 387, pp. 195-201, Feb. 2006.
Giselle F. Passos et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847, vol. 172, The American Association of Immunologists, Inc.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.
Joao B. Pesquero et al., "Genetically Altered Animal Models in the Kallikrein-Kinin System", Biol. Chem., Feb. 2006, pp. 119-126, vol. 387.
A. Prat et al, "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology.
Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol., Mar. 31, 2005, pp. G361-G366, vol. 289, American Physiological Society.
International Search Report and Written Opinion, mailed Aug. 21, 2008.

* cited by examiner

Primary Examiner — Yong Chu
(74) Attorney, Agent, or Firm — Crowell & Moring LLP

(57) ABSTRACT

Substituted sulfonamide compounds corresponding to formula I

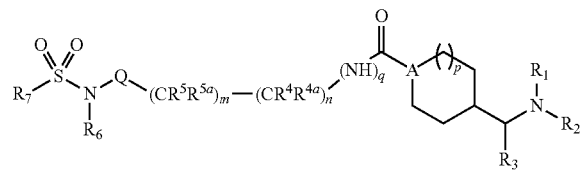

pharmaceutical compositions comprising them, a process for preparing them, and the use of such compounds to treat or inhibit pain and other disorders or disease states.

24 Claims, No Drawings

SUBSTITUTED SULFONAMIDE COMPOUNDS

BACKGROUND OF THE INVENTION

The present invention relates to substituted sulfonamide derivatives, to a process for their preparation, to medicaments comprising these compounds, and to the use of substituted sulfonamide derivatives in the preparation of medicaments and in the treatment of pain and various other conditions.

Unlike the constitutive expression of the bradykinin 2 receptor (B2R), the bradykinin 1 receptor (B1R) is not expressed or is expressed only weakly in most tissues. However, the expression of B1R in various cells is inducible. For example, following inflammation reactions there is a rapid and pronounced induction of B1R in neuronal cells but also in various peripheral cells such as fibroblasts, endothelial cells, granulocytes, macrophages and lymphocytes. Accordingly, in the course of inflammation reactions there is a switch from B2R to B1R dominance in the cells that are involved. The cytokines interleukin-1 (IL-1) and tumor necrosis factor alpha (TNFα) play a substantial part in this B1R up-regulation (Passos et al., J. Immunol. 2004, 172, 1839-1847). Following activation with specific ligands, B1R-expressing cells are then themselves able to secrete inflammation-promoting cytokines such as IL-6 and IL-8 (Hayashi et al., Eur. Respir. J. 2000, 16, 452-458). This results in the immigration of further inflammatory cells, for example neutrophilic granulocytes (Pesquero et al., PNAS 2000, 97, 8140-8145). By way of these mechanisms, the bradykinin B1R system can contribute to the chronification of diseases. This is proved by a large number of animal experiments (overviews in Leeb-Lundberg et al., Pharmacol. Rev. 2005, 57, 27-77 and Pesquero et al., Biol. Chem. 2006, 387, 119-126). In humans too, enhanced expression of B1R is found, for example, in enterocytes and macrophages in the affected tissue of patients with inflammatory intestinal diseases (Stadnicki et al., Am. J. Physiol. Gastrointest. Liver Physiol. 2005, 289, G361-366) or on T-lymphocytes of patients with multiple sclerosis (Prat 1999), or activation of the bradykinin B2R-B1R system is found following infections with *Staphylococcus aureus* (Bengtson et al., Blood 2006, 108, 2055-2063). Infections with *Staphylococcus aureus* are responsible for symptoms ranging from superficial skin infections to septic shock.

Due to the described pathophysiological relationships there is a great therapeutic potential for the use of B1R antagonists in acute and, in particular, chronic inflammatory diseases. These include respiratory diseases (Asthma bronchiale, allergies, COPD/chronic-obstructive pulmonary disease, cystic fibrosis, etc.), inflammatory intestinal diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucosa (Behcet's disease, pelvitis, prostatitis, etc.), rheumatic diseases (rheumatoid arthritis, osteoarthritis, etc.), septic shock and reperfusion syndrome (following heart attack, stroke).

In addition, the bradykinin (receptor) system is also involved in regulating angiogenesis (potential as an angiogenesis inhibitor in cancer and macular degeneration of the eye), and B1R knockout mice are protected against the induction of excess weight as a result of a particularly high-fat diet (Pesquero et al., Biol. Chem. 2006, 387, 119-126). B1R antagonists are therefore suitable also for the treatment of obesity.

B1R antagonists are suitable in particular for the treatment of pain, in particular inflammatory pain and neuropathic pain (Calixto et al., Br. J. Pharmacol. 2004, 1-16), in particular diabetic neuropathy (Gabra et al., Biol. Chem. 2006, 387, 127-143).

Compounds that bind to the t-opioid receptor are suitable in particular for the treatment of pain but also for the treatment of depression, pruritus, lack of drive, diarrhoea and for anxiolysis.

SUMMARY OF THE INVENTION

An object underlying the invention was to provide novel compounds which are suitable especially as pharmacological active ingredients in medicaments, in particular substances having analgesic activity, which are suitable for pain therapy—in particular also for the therapy of inflammatory pain and neuropathic pain.

The invention accordingly provides substituted sulfonamide derivatives of the general formula I

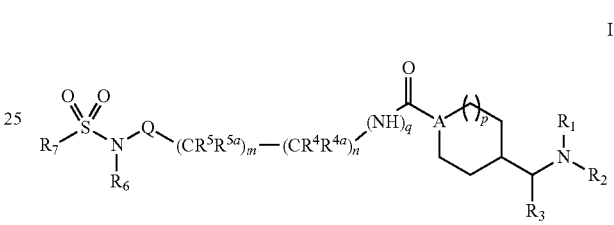

wherein
m represents 0, 1 or 2,
n represents 0, 1 or 2,
p represents 0, 1 or 2,
q represents 0 or 1,
A represents CH—NH—, CH—CH$_2$—NH—, CH—CH$_2$—CH$_2$—NH or CH—CH$_2$—CH$_2$—CH$_2$—NH, wherein individual hydrogen atoms can also be replaced by C$_{1-5}$-alkyl,
R$^1$ and R$^2$ independently of one another denote H; C$_{1-6}$-alkyl, in each case saturated or unsaturated, branched or unbranched, unsubstituted or mono- or poly-substituted; or aryl linked via a C$_{1-3}$-alkyl chain and unsubstituted or mono- or poly-substituted, wherein R$^1$ and R$^2$ do not simultaneously denote H, or
R$^1$ and R$^2$ together denote CH$_2$CH$_2$OCH$_2$CH$_2$, CH$_2$CH$_2$NR$^8$CH$_2$CH$_2$ or (CH$_2$)$_{3-6}$, wherein
R$^8$ denotes H; C$_{1-6}$-alkyl, in each case saturated or unsaturated, branched or unbranched, unsubstituted or mono- or poly-substituted; aryl, heteroaryl, in each case unsubstituted or mono- or poly-substituted, or aryl or heteroaryl linked via a C$_{1-3}$-alkyl chain and in each case unsubstituted or mono- or poly-substituted;
R$^3$ represents C$_{1-8}$-alkyl, in each case saturated or unsaturated, branched or unbranched, unsubstituted or mono- or poly-substituted; aryl or heteroaryl, in each case unsubstituted or mono- or poly-substituted; or aryl or heteroaryl linked via a C$_{1-3}$-alkyl chain and in each case unsubstituted or mono- or poly-substituted;
R$^4$ and R$^{4a}$ independently of one another represent H, C$_{1-6}$-alkyl, in each case saturated or unsaturated, branched or unbranched, unsubstituted or mono- or poly-substituted; F; Cl; aryl, in each case unsubstituted or mono- or poly-substituted; or aryl linked via a C$_{1-3}$-alkyl chain and in each case unsubstituted or mono- or poly-substituted;
R$^5$ and R$^{5a}$ independently of one another represent H; or C$_{1-6}$-alkyl, in each case saturated or unsaturated, branched or unbranched, unsubstituted or mono- or poly-substituted; OH, $OC_{1-6}$-alkyl, F, Cl, phenoxy or benzyloxy;

Q denotes a single bond, —$CH_2$—, —$CH_2$—$CH_2$— or

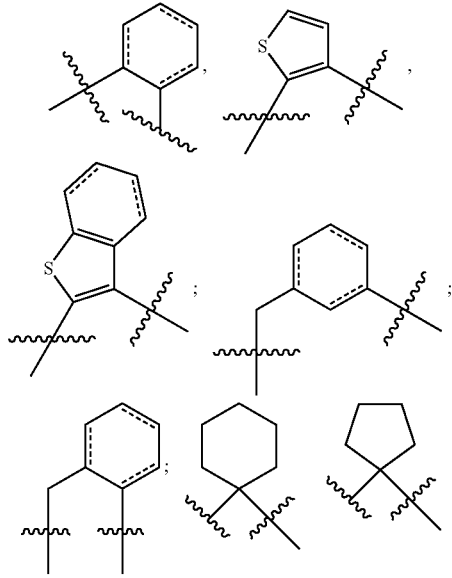

wherein ==== represents a single bond or a double bond;

$R^6$ represents H; $C_{1-6}$-alkyl, in each case saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; aryl or $C_{3-8}$-cycloalkyl linked via a $C_{1-3}$-alkyl chain; or $R^6$ together with Q and including the adjacent nitrogen forms a four-, five-, six- or seven-membered carbocyclic ring which can be saturated or unsaturated and can contain a further hetero atom O, S or N, to which a further five- or six-membered ring, saturated or unsaturated, can be fused; wherein in the case of the common ring closure Q represents

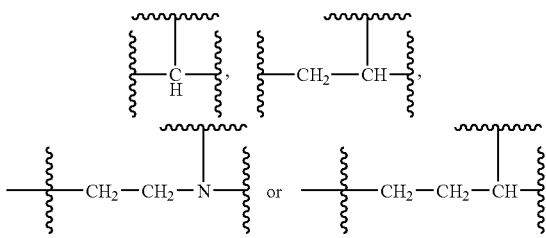

and the ring can be substituted in any position by phenyl, =O, OH, $OC_{1-6}$-alkyl, F, Cl, $CF_3$ or $C_{1-6}$-alkyl; and $R^7$ represents aryl or heteroaryl, in each case unsubstituted or mono- or poly-substituted; aryl or heteroaryl linked via a $C_{1-3}$-alkyl group and in each case unsubstituted or mono- or poly-substituted;

in the form of the racemate; of the enantiomers, diastereoisomers, mixtures of the enantiomers or diastereoisomers or of an individual enantiomer or diastereoisomer; of the bases and/or salts of physiologically acceptable acids.

The compounds have an affinity for the human B1 receptor. In addition, they especially have an affinity for the µ-opioid receptor.

When the group A in the compounds of the general formula I represents CH—NH—, CH—$CH_2$—NH—, CH—$CH_2$—$CH_2$—NH or CH—$CH_2$—$CH_2$—$CH_2$—NH—, the C-chain end is always bonded to the ring and the N-chain end is linked to the carbonyl group.

Within the scope of this invention, the expressions "$C_{1-3}$-alkyl", $C_{1-6}$-alkyl" and "$C_{1-8}$-alkyl" denote acyclic saturated or unsaturated hydrocarbon radicals which can be branched- or straight-chained as well as unsubstituted or mono- or poly-substituted, having from 1 to 3 carbon atoms or from 1 to 6 carbon atoms or from 1 to 8 carbon atoms, respectively, that is to say $C_{1-3}$-alkanyls, $C_{2-3}$-alkenyls and $C_{2-3}$-alkynyls or $C_{1-6}$-alkanyls, $C_{2-6}$-alkenyls and $C_{2-6}$-alkynyls or $C_{1-8}$-alkanyls, $C_{2-8}$-alkenyls and $C_{2-8}$-alkynyls. Alkenyls have at least one C—C double bond and alkynyls have at least one C—C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, hexyl, heptyl, octyl, ethylenyl (vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl. Methyl, ethyl and n-propyl are particularly advantageous.

Within the scope of this invention, the term "aryl" denotes aromatic hydrocarbons, including phenyls and naphthyls. The aryl radicals can also be fused with further saturated, (partially) unsaturated or aromatic ring systems. Each aryl radical can be unsubstituted or mono- or poly-substituted, wherein the aryl substituents can be identical or different and can be located at any desired and possible position of the aryl. Aryl is advantageously selected from the group comprising phenyl, 1-naphthyl and 2-naphthyl, each of which can be unsubstituted or mono- or poly-substituted. The phenyl radical is particularly advantageous.

The term "heteroaryl" denotes a 5-, 6- or 7-membered cyclic aromatic group containing at least one, optionally also 2, 3, 4 or 5, hetero atom(s), the hetero atoms being identical or different and the heterocycle being unsubstituted or mono- or poly-substituted; in the case of substitution on the heterocycle, the substituents can be identical or different and can be located at any desired and possible position of the heteroaryl. The heterocycle can also be part of a bi- or poly-cyclic system. Preferred hetero atoms are nitrogen, oxygen and sulfur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl and oxadiazolyl, it being possible for bonding to the compounds of the general structure I to take place via any desired and possible ring member of the heteroaryl radical. Thienyl, furyl, benzothiadiazolyl, oxadiazolyl and pyridyl are particularly preferred.

The expression "aryl or heteroaryl bonded via $C_{1-3}$-alkyl" means, for the purposes of the present invention, that $C_{1-3}$-alkyl and aryl or heteroaryl have the meanings defined above and the aryl or heteroaryl radical is bonded to the compound of the general structure I via a $C_{1-3}$-alkyl group. Phenyl, benzyl and phenethyl are particularly advantageous within the scope of this invention.

In connection with "alkyl" and "cycloalkyl", the term "substituted" within the scope of this invention is understood as meaning the substitution of a hydrogen radical by F, Cl, Br, I, —CN, $NH_2$, NH—$C_{1-6}$-alkyl, NH—$C_{1-6}$-alkyl-OH, $C_{1-6}$- alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, $C(=O)C_{1-6}$-alkyl, $CO_2H$, $CO_2$—$C_{1-6}$-alkyl, phenyl or benzyl, wherein polysubstituted radicals are to be understood as being those radicals that are polysubstituted, for example di- or tri-substituted, either on different atoms or on the same atom, for example trisubstituted on the same carbon atom, as in the case of $CF_3$ or —$CH_2CF_3$, or at different positions, as in the case of —CH(OH)—CH=CH—$CHCl_2$. Polysubstitution can be carried out with the same or with different substituents. Preferred radicals in connection with "alkyl" and "cycloalkyl" are F, Cl, —CN, $NH_2$, $OCH_3$, OH, $CO_2$—$CH_3$, $CO_2$—$C_2H_5$, =O and $SCH_3$.

In relation to "aryl" and "heteroaryl", "mono- or poly-substituted" within the scope of this invention is understood as meaning the substitution of one or more hydrogen atoms of the ring system one or more times, for example two, three or four times, by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, $C(=O)C_{1-6}$-alkyl, $CO_2H$, $CH_2SO_2$-phenyl, $CO_2$—$C_{1-6}$-alkyl, $OCF_3$, $CF_3$,

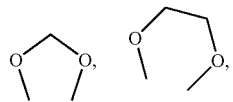

$C_{1-6}$-alkyl, phenyl, pyridyl, thienyl or furyl; on one atom or optionally on different atoms, wherein a substituent can itself optionally be substituted. The polysubstitution is carried out with the same substituent or with different substituents. Preferred substituents for "aryl" are —F, —Cl, tert-butyl, $CF_3$, $OCF_3$,

$CH_3$ or $OCH_3$.

Within the scope of this invention, the expression "a salt formed with a physiologically acceptable acid" is understood as meaning salts of the active ingredient in question with inorganic or organic acids that are physiologically acceptable—in particular when used in humans. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and aspartic acid. Citric acid and hydrochloric acid are particularly preferred.

The expressions $(CH_2)_{3-6}$ and $(CH_2)_{4-5}$ are to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and —$CH_2$—$CH_2$—$CH_2$—$CH_2$—, —$CH_2$—$CH_2$—$CH_2$—$CH_2$—$CH_2$—, respectively.

Preference is given to substituted amide derivatives of the general formula I wherein the radicals or groups $R^1$-$R^8$, $R^H$, $R^J$, A, Z and Q and also m, n, p and q have the meaning given above, wherein "alkyl substituted" and "cycloalkyl substituted" mean the substitution of one or more hydrogen radicals by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, $C(=O)C_{1-6}$-alkyl, $CO_2H$, $CO_2$—$C_{1-6}$-alkyl, phenyl or benzyl, "aryl substituted" and "heteroaryl substituted" mean the substitution of one or more hydrogen atoms of the ring system one or more times, for example two, three or four times, by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, $C(=O)C_{1-6}$-alkyl, $CO_2H$, $CH_2SO_2$-phenyl, $CO_2$—$C_{1-6}$-alkyl, $OCF_3$, $CF_3$,

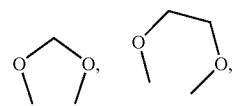

$C_{1-6}$-alkyl, phenyl, pyridyl, thienyl or furyl, in the form of the racemate; of the enantiomers, diastereoisomers, mixtures of the enantiomers or diastereoisomers or of an individual enantiomer or diastereoisomer; of the bases and/or salts of physiologically acceptable acids.

The radicals and groups or substituents described hereinafter as being preferred can be combined in the compounds according to the invention with the broadest meaning of the other radicals, but also with preferred meanings of other radicals and groups or substituents.

Preference is given within the scope of this invention to substituted sulfonamide derivatives wherein A represents CH—NH—, CH—$CH_2$—NH—, CH—$CH_2$—$CH_2$—NH or CH—$CH_2$—$CH_2$—$CH_2$—NH, wherein individual hydrogen atoms can also be replaced by $C_{1-5}$-alkyl.

p preferably represents 1.

Preference is given to compounds in which q represents 0.

Preference is given also to substituted sulfonamide derivatives wherein $R^1$ and $R^2$ independently of one another denote H; $CH_3$; $C_2H_5$; or phenyl linked via a $C_{1-3}$-alkyl chain, wherein $R^1$ and $R^2$ do not simultaneously denote H, or $R^1$ and $R^2$ together denote $CH_2CH_2OCH_2CH_2$, $CH_2CH_2NR^8CH_2CH_2$ or $(CH_2)_{3-5}$.

Particular preference is given to substituted sulfonamide derivatives wherein $R^1$ and $R^2$ independently of one another denote H or $CH_3$, in particular $CH_3$.

Preference is given within the scope of this invention also to substituted sulfonamide derivatives wherein $R^3$ represents aryl or heteroaryl, in each case unsubstituted or mono- or poly-substituted; or aryl linked via a $C_{1-3}$-alkyl chain and in each case unsubstituted or mono- or poly-substituted.

Particular preference is given to substituted sulfonamide derivatives wherein $R^3$ represents 2-thienyl, 4-fluorophenyl, 3-fluorophenyl, 4-chlorophenyl, phenethyl, phenyl or benzyl.

Preference is given also to substituted sulfonamide derivatives wherein $R^4$ and $R^{4a}$ each represent H.

In addition, preference is given to substituted sulfonamide derivatives wherein $R^5$ and $R^{5a}$ each represent H.

Preference is given also to substituted sulfonamide derivatives wherein $R^6$ represents methyl, ethyl or benzyl and Q represents a single bond, wherein $R^6$ in particular represents methyl.

Preference is further given to substituted sulfonamide derivatives wherein

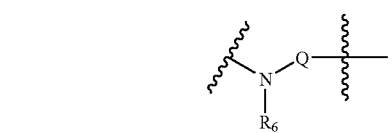

represents

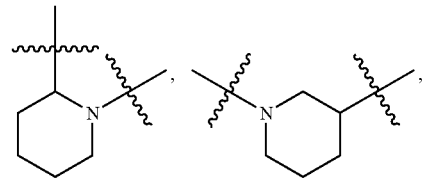

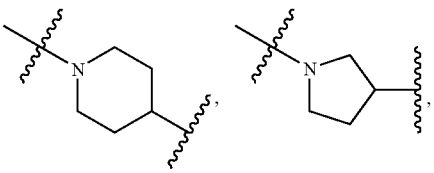

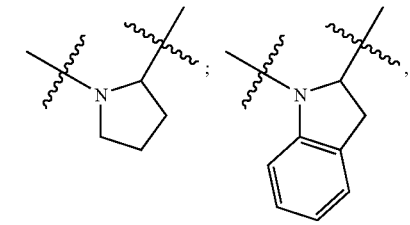

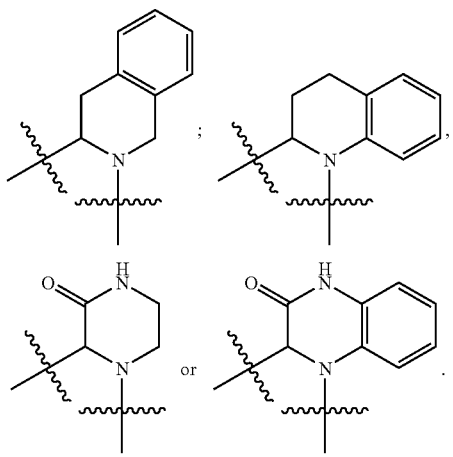

Preference is given also to substituted sulfonamide derivatives wherein Q is

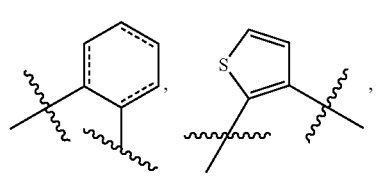

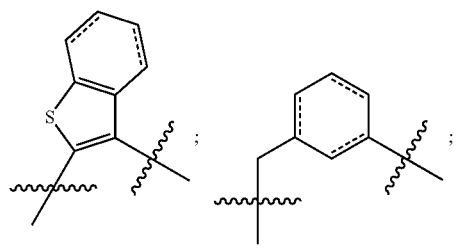

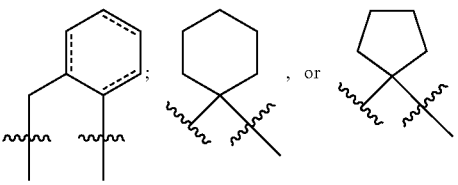

Preference is given also to substituted sulfonamide derivatives wherein $R^7$ represents phenyl or naphthyl, unsubstituted or mono- or poly-substituted, in particular phenyl.

Particular preference is given to substituted sulfonamide derivatives wherein $R^7$ represents 2,4-dichlorophenyl, 2,4,6-trichlorophenyl, 4-methoxyphenyl, 3-trifluoromethylphenyl, 2,6-dimethyl-4-methoxyphenyl, 3,4-dichlorophenyl, 2,5-dimethyl-4-chlorophenyl or naphthyl.

Preference is given also to substituted sulfonamide derivatives wherein the group

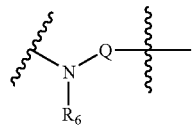

of formula I represents

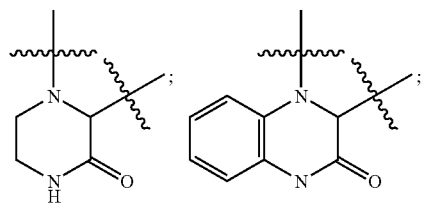

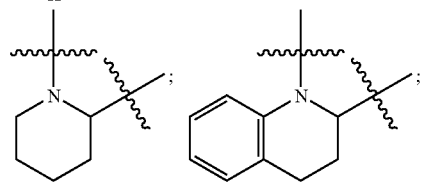

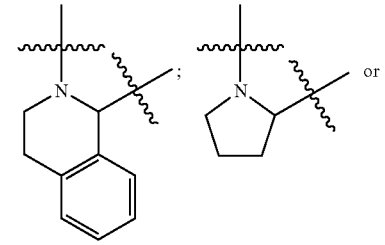

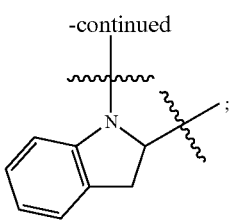

m represents 0, 1 or 2;
n represents 0;
q represents 0; and
$R^5$ and $R^{5a}$ represent H;
or
Q represents a single bond;
m represents 0, 1 or 2;
n represents 1 or 2;
q represents 0 or 1;
$R^4$ and $R^{4a}$ each independently of the other represents H or aryl;
$R^5$ and $R^{5a}$ represent H; and
$R^6$ represents H or $C_{1-6}$-alkyl;
or
Q represents

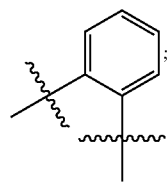 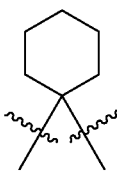 or 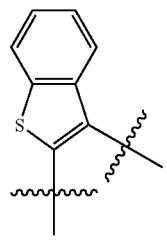

m represents 0 or 1, preferably 0;
n and q represent 0;
$R^5$ and $R^{5a}$ represent H; and
$R^6$ represents H or $C_{1-6}$-alkyl.

Preference is given also to substituted sulfonamide derivatives wherein in the general formula I
A represents N, NH—CH, NH—CH$_2$—CH or NH—CH$_2$—CH$_2$—CH, wherein individual hydrogen atoms can also be replaced by $C_{1-5}$-alkyl;
$R^1$ and $R^2$ independently of one another represent $C_{1-6}$-alkyl, in particular methyl, ethyl, n-propyl, isopropyl, n-butyl, sec-butyl, isobutyl and tert-butyl, or together with the nitrogen atom to which they are bonded form a group selected from

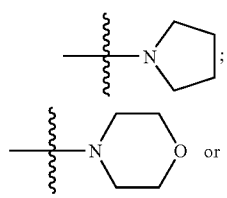

and
$R^3$ represents aryl, in particular phenyl or furanyl, which can be linked via a $C_{1-3}$-alkyl group, wherein the aryl is in each case unsubstituted or mono- or poly-substituted by identical or different substituents selected independently from the group consisting of methyl, ethyl, methoxy, ethoxy, F, Cl, Br, F, CN, CF$_3$, OCF$_3$ and OH.

Preference is further given to substituted sulfonamide derivatives wherein the group

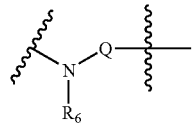

in formula I represents

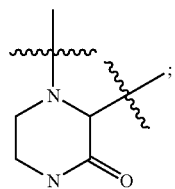 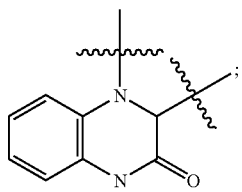

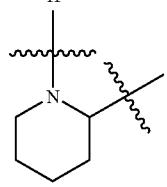 or 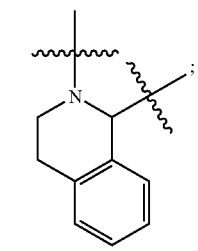

m represents 1 or 2, in particular 1;
n and q represent 0;
$R^5$ and $R^{5a}$ represent H;
A represents N, NH—CH or NH—CH$_2$—CH, in particular N or NH—CH;
$R^1$ and $R^2$ independently of one another represent $C_{1-6}$-alkyl, in particular methyl, ethyl, n-propyl, isopropyl, n-butyl, sec-butyl, isobutyl and tert-butyl, or together with the nitrogen atom to which they are bonded form a group selected from

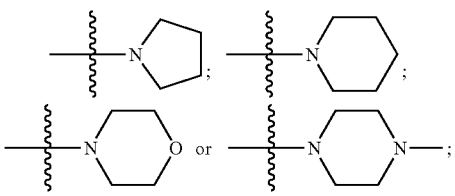

and
$R_3$ represents phenyl which can be linked via a $C_{1-3}$-alkyl group, wherein the phenyl is in each case unsubstituted or mono- or poly-substituted by identical or different substituents selected independently from the group consisting of methyl, ethyl, methoxy, ethoxy, F, Cl, Br, F, CN, CF$_3$, OCF$_3$ and OH, in particular methyl, methoxy, F, Cl, Br, CN, CF$_3$ and OH.

Very particular preference is given to substituted sulfonamide compounds selected from the group consisting of:
(1) N-(3-{3-[4-(dimethylaminophenyl]methyl)cyclohexyl]ureido}propyl)-4-methoxy-2,3,6,N-tetramethylbenzenesulfonamide (2) (N-(3-(3-((4-((dimethylamino)(phenyl)methyl)cyclohexyl)methyl)ureido)propyl)-4-methoxy-N,2,3,6-tetramethylbenzenesulfonamide
(3) 4-methoxy-N,2,3,6-tetramethyl-N-(3-(3-(4-(phenyl(pyrrolidin-1-yl)methyl)cyclohexyl)ureido)propyl)benzenesulfonamide
(4) 4-(dimethylamino-phenyl-methyl)-piperidine-1-carboxylic acid {3-[(4-methoxy-2,3,6-trimethyl-benzenesulfonyl)-methyl-amino]-propyl}-amide
(5) 5-[methyl-(2,4,6-trichloro-benzenesulfonyl)-amino]-pentanecarboxylic acid [4-(dimethylamino-phenyl-methyl)-cyclohexyl]-amide
(6) 5-[methyl-(2,4,6-trichloro-benzenesulfonyl)-amino]-pentanecarboxylic acid [4-(phenyl-piperidin-1-yl-methyl)-cyclohexyl]-amide
(7) 5-[methyl-(2,4,6-trichloro-benzenesulfonyl)-amino]-pentanecarboxylic acid [4-(dimethylamino-phenyl-methyl)-cyclohexylmethyl]-amide
(8) N-[4-(dimethylamino-phenyl-methyl)-cyclohexylmethyl]-2-[1-(3-trifluoromethylbenzenesulfonyl)-piperidin-2-yl]-acetamide
(9) N-[4-(dimethylamino-phenyl-methyl)-cyclohexyl]-2-[2-(4-methoxy-benzenesulfonyl)-1,2,3,4-tetrahydro-isoquinolin-1-yl]-acetamide
(10) 2-[2-(3,4-dichloro-benzenesulfonyl)-1,2,3,4-tetrahydro-isoquinolin-1-yl]-N-[4-(dimethylamino-phenyl-methyl)-cyclohexyl]-acetamide
(11) 2-[(3,4-dichloro-benzenesulfonyl)-methyl-amino]-N-[4-(dimethylamino-phenylmethyl)-cyclohexyl]-benzamide
(12) 2-[(3,4-dichloro-benzenesulfonyl)-methyl-amino]-4,5,6,7-tetrahydrobenzo[b]thiophene-3-carboxylic acid [4-(dimethylamino-phenyl-methyl)cyclohexyl]-amide
(13) N-{4-[dimethylamino-(3-fluoro-phenyl)-methyl]-cyclohexyl}-2-[2-(4-methoxybenzenesulfonyl)-1,2,3,4-tetrahydro-isoquinolin-1-yl]-acetamide
(14) N-{4-[dimethylamino-(4-fluoro-phenyl)-methyl]-cyclohexyl}-2-[2-(4-methoxybenzenesulfonyl)-1,2,3,4-tetrahydro-isoquinolin-1-yl]-acetamide
(15) N-[4-(dimethylamino-thiophen-2-yl-methyl)-cyclohexyl]-2-[2-(4-methoxybenzenesulfonyl)-1,2,3,4-tetrahydro-isoquinolin-1-yl]-acetamide
(16) N-{4-[dimethylamino-(3-fluoro-phenyl)-methyl]-cyclohexylmethyl}-2-[2-(4-methoxy-benzenesulfonyl)-1,2,3,4-tetrahydro-isoquinolin-1-yl]-acetamide
(17) N-[4-(dimethylamino-phenyl-methyl)-cyclohexylmethyl]-2-[2-(4-methoxybenzenesulfonyl)-1,2,3,4-tetrahydro-isoquinolin-1-yl]-acetamide
(18) N-[4-(1-dimethylamino-3-phenyl-propyl)-cyclohexylmethyl]-2-[2-(4-methoxybenzenesulfonyl)-1,2,3,4-tetrahydro-isoquinolin-1-yl]-acetamide
(19) N-{4-[dimethylamino-(4-fluoro-phenyl)-methyl]-cyclohexylmethyl}-2-[2-(4-methoxy-benzenesulfonyl)-1,2,3,4-tetrahydro-isoquinolin-1-yl]-acetamide
(20) N-{4-[(4-chloro-phenyl)-dimethylamino-methyl]-cyclohexylmethyl}-2-[2-(4-methoxy-benzenesulfonyl)-1,2,3,4-tetrahydro-isoquinolin-1-yl]-acetamide
(21) N-[4-(dimethylamino-thiophen-2-yl-methyl)-cyclohexylmethyl]-2-[2-(4-methoxybenzenesulfonyl)-1,2,3,4-tetrahydro-isoquinolin-1-yl]-acetamide
(22) N-(2-{4-[(4-chloro-phenyl)-dimethylamino-methyl]-cyclohexyl}-ethyl)-2-[2-(4-methoxy-benzenesulfonyl)-1,2,3,4-tetrahydro-isoquinolin-1-yl]-acetamide
(23) N-(2-{4-[dimethylamino-(3-fluoro-phenyl)-methyl]-cyclohexyl}-ethyl)-2-[2-(4-methoxy-benzenesulfonyl)-1,2,3,4-tetrahydro-isoquinolin-1-yl]-acetamide
(24) N-(2-{4-[dimethylamino-(4-fluoro-phenyl)-methyl]-cyclohexyl}-ethyl)-2-[2-(4-methoxy-benzenesulfonyl)-1,2,3,4-tetrahydro-isoquinolin-1-yl]-acetamide
(25) N-{2-[4-(dimethylamino-thiophen-2-yl-methyl)-cyclohexyl]-ethyl}-2-[2-(4-methoxy-benzenesulfonyl)-1,2,3,4-tetrahydro-isoquinolin-1-yl]-acetamide
(26) 2-(2-(3,4-dichlorophenylsulfonyl)-1,2,3,4-tetrahydroisoquinolin-1-yl)-N-(4-((dimethylamino)(3-fluorophenyl)methyl)cyclohexyl)acetamide
(27) 2-(2-(3,4-dichlorophenylsulfonyl)-1,2,3,4-tetrahydroisoquinolin-1-yl)-N-(4-((dimethylamino)(4-fluorophenyl)methyl)cyclohexyl)acetamide
(28) 2-[2-(3,4-dichloro-benzenesulfonyl)-1,2,3,4-tetrahydro-isoquinolin-1-yl]-N-{4-[dimethylamino-(3-fluoro-phenyl)-methyl]-cyclohexylmethyl}-acetamide
(29) 2-[2-(3,4-dichloro-benzenesulfonyl)-1,2,3,4-tetrahydro-isoquinolin-1-yl]-N-[4-(dimethylamino-phenyl-methyl)-cyclohexylmethyl]-acetamide
(30) 2-[2-(3,4-dichloro-benzenesulfonyl)-1,2,3,4-tetrahydro-isoquinolin-1-yl]-N-[4-(1-dimethylamino-3-phenyl-propyl)-cyclohexylmethyl]-acetamide
(31) 2-[2-(3,4-dichloro-benzenesulfonyl)-1,2,3,4-tetrahydro-isoquinolin-1-yl]-N-{4-[dimethylamino-(4-fluoro-phenyl)-methyl]-cyclohexylmethyl}-acetamide
(32) N-{4-[(4-chloro-phenyl)-dimethylamino-methyl]-cyclohexylmethyl}-2-[2-(3,4-dichloro-benzenesulfonyl)-1,2,3,4-tetrahydro-isoquinolin-1-yl]-acetamide
(33) N-(2-{4-[(4-chloro-phenyl)-dimethylamino-methyl]-cyclohexyl}-ethyl)-2-[2-(3,4-dichloro-benzenesulfonyl)-1,2,3,4-tetrahydro-isoquinolin-1-yl]-acetamide
(34) 2-[2-(3,4-dichloro-benzenesulfonyl)-1,2,3,4-tetrahydro-isoquinolin-1-yl]-N-(2-{4-[dimethylamino-(3-fluoro-phenyl)-methyl]-cyclohexyl}-ethyl)-acetamide
(35) 2-[2-(3,4-dichloro-benzenesulfonyl)-1,2,3,4-tetrahydro-isoquinolin-1-yl]-N-(2-{4-[dimethylamino-(4-fluoro-phenyl)-methyl]-cyclohexyl}-ethyl)-acetamide
(36) 2-[(3,4-dichloro-benzenesulfonyl)-methyl-amino]-N-{4-[dimethylamino-(3-fluoro-phenyl)-methyl]-cyclohexyl}-benzamide
(37) 2-[(3,4-dichloro-benzenesulfonyl)-methyl-amino]-N-{4-[dimethylamino-(4-fluoro-phenyl)-methyl]-cyclohexyl}-benzamide
(38) 2-[(3,4-dichloro-benzenesulfonyl)-methyl-amino]-N-[4-(dimethylamino-phenylmethyl)-cyclohexylmethyl]-benzamide
(39) 2-[(3,4-dichloro-benzenesulfonyl)-methyl-amino]-N-[4-(1-dimethylamino-3-phenyl-propyl)-cyclohexylmethyl]-benzamide
(40) 2-[(3,4-dichloro-benzenesulfonyl)-methyl-amino]-N-{4-[dimethylamino-(4-fluoro-phenyl)-methyl]-cyclohexylmethyl}-benzamide
(41) N-{4-[(4-chloro-phenyl)-dimethylamino-methyl]-cyclohexylmethyl}-2-[(3,4-dichloro-benzenesulfonyl)-methyl-amino]-benzamide
(42) 2-[(3,4-dichloro-benzenesulfonyl)-methyl-amino]-N-[4-(dimethylamino-thiophen-2-yl-methyl)-cyclohexylmethyl]-benzamide
(43) N-(2-{4-[(4-chloro-phenyl)-dimethylamino-methyl]-cyclohexyl}-ethyl)-2-[(3,4-dichloro-benzenesulfonyl)-methyl-amino]-benzamide
(44) 2-[(3,4-dichloro-benzenesulfonyl)-methyl-amino]-N-(2-{4-[dimethylamino-(3-fluoro-phenyl)-methyl]-cyclohexyl}-ethyl)-benzamide
(45) 2-[(3,4-dichloro-benzenesulfonyl)-methyl-amino]-N-(2-{4-[dimethylamino-(4-fluoro-phenyl)-methyl]-cyclohexyl}-ethyl)-benzamide

(46) 2-[(3,4-dichloro-benzenesulfonyl)-methyl-amino]-4,5,6,7-tetrahydrobenzo[b]thiophene-3-carboxylic acid [4-(dimethylamino-phenyl-methyl)cyclohexylmethyl]-amide

(47) 2-[(3,4-dichloro-benzenesulfonyl)-methyl-amino]-4,5,6,7-tetrahydrobenzo[b]thiophene-3-carboxylic acid {4-[dimethylamino-(4-fluoro-phenyl)methyl]-cyclohexylmethyl}-amide

(48) 2-[(3,4-dichloro-benzenesulfonyl)-methyl-amino]-4,5,6,7-tetrahydrobenzo[b]thiophene-3-carboxylic acid {4-[(4-chloro-phenyl)-dimethylamino-methyl]-cyclohexylmethyl}-amide

(49) 2-[(3,4-dichloro-benzenesulfonyl)-methyl-amino]-4,5,6,7-tetrahydrobenzo[b]thiophene-3-carboxylic acid [4-(dimethylamino-thiophen-2-yl-methyl)cyclohexylmethyl]-amide

(50) N-(2-(4-((4-chlorophenyl)(dimethylamino)methyl)cyclohexyl)ethyl)-2-(3,4-dichloro-N-methylphenylsulfonamido)-4,5,6,7-tetrahydrobenzo[b]thiophene-3-carboxamide

(51) 2-(3,4-dichloro-N-methylphenylsulfonamido)-N-(2-(4-((dimethylamino)(3-fluorophenyl)methyl)cyclohexyl)ethyl)-4,5,6,7-tetrahydrobenzo[b]thiophene-3-carboxamide

(52) 2-(3,4-dichloro-N-methylphenylsulfonamido)-N-(2-(4-((dimethylamino)(4-fluorophenyl)methyl)cyclohexyl)ethyl)-4,5,6,7-tetrahydrobenzo[b]thiophene-3-carboxamide

(53) 2-(3,4-dichloro-N-methylphenylsulfonamido)-N-(2-(4-((dimethylamino)(thiophen-2-yl)methyl)cyclohexyl)ethyl)-4,5,6,7-tetrahydrobenzo[b]thiophene-3-carboxamide

(54) 2-[1-(3,4-dichloro-benzenesulfonyl)-3-oxo-1,2,3,4-tetrahydro-quinoxalin-2-yl]-N-[4-(morpholin-4-yl-phenyl-methyl)-cyclohexyl]-acetamide

(55) 2-[1-(2,4-dichloro-benzenesulfonyl)-3-oxo-piperazin-2-yl]-N-[4-(morpholin-4-yl-phenyl-methyl)-cyclohexylmethyl]-acetamide

(56) 2-[1-(2,4-dichloro-benzenesulfonyl)-3-oxo-piperazin-2-yl]-N-[4-(1-morpholin-4-yl-3-phenyl-propyl)-cyclohexylmethyl]-acetamide

(57) 2-[1-(2,4-dichloro-benzenesulfonyl)-3-oxo-piperazin-2-yl]-N-[4-(3-phenyl-1-pyrrolidin-1-yl-propyl)-cyclohexylmethyl]-acetamide

(58) 2-[1-(2,4-dichloro-benzenesulfonyl)-3-oxo-piperazin-2-yl]-N-[4-(phenyl-pyrrolidin-1-yl-methyl)-cyclohexylmethyl]-acetamide

(59) 2-[1-(2,4-dichloro-benzenesulfonyl)-3-oxo-piperazin-2-yl]-N-[4-(3-phenyl-1-piperidin-1-yl-propyl)-cyclohexyl]-acetamide

(60) 2-[1-(2,4-dichloro-benzenesulfonyl)-3-oxo-piperazin-2-yl]-N-[4-(1-morpholin-4-yl-3-phenyl-propyl)-cyclohexyl]-acetamide

(61) 2-[1-(2,4-dichloro-benzenesulfonyl)-3-oxo-piperazin-2-yl]-N-{4-[(4-methyl-piperazin-1-yl)-phenyl-methyl]-cyclohexyl}-acetamide

(62) 4-(2,4-dichloro-benzenesulfonyl)-3-{2-[4-(morpholin-4-yl-phenyl-methyl)piperidin-1-yl]-2-oxo-ethyl}-piperazin-2-one

(63) 4-(2,4-dichlorophenylsulfonyl)-3-(2-(2-(1-morpholino-2-phenylethyl)piperidin-1-yl)-2-oxoethyl)piperazin-2-one

(64) 2-[1-(3,4-dichloro-benzenesulfonyl)-3-oxo-1,2,3,4-tetrahydro-quinoxalin-2-yl]-N-[4-(morpholin-4-yl-phenyl-methyl)-cyclohexylmethyl]-acetamide

(65) 2-[1-(3,4-dichloro-benzenesulfonyl)-3-oxo-1,2,3,4-tetrahydro-quinoxalin-2-yl]-N-[4-(1-morpholin-4-yl-3-phenyl-propyl)-cyclohexylmethyl]-acetamide

(66) 2-[1-(3,4-dichloro-benzenesulfonyl)-3-oxo-1,2,3,4-tetrahydro-quinoxalin-2-yl]-N-[4-(3-phenyl-1-pyrrolidin-1-yl-propyl)-cyclohexylmethyl]-acetamide

(67) 2-[1-(3,4-dichloro-benzenesulfonyl)-3-oxo-1,2,3,4-tetrahydro-quinoxalin-2-yl]-N-[4-(phenyl-pyrrolidin-1-yl-methyl)-cyclohexylmethyl]-acetamide

(68) 2-[1-(3,4-dichloro-benzenesulfonyl)-3-oxo-1,2,3,4-tetrahydro-quinoxalin-2-yl]-N-[4-(3-phenyl-1-piperidin-1-yl-propyl)-cyclohexyl]-acetamide

(69) 2-[1-(3,4-dichloro-benzenesulfonyl)-3-oxo-1,2,3,4-tetrahydro-quinoxalin-2-yl]-N-[4-(1-morpholin-4-yl-3-phenyl-propyl)-cyclohexyl]-acetamide

(70) 2-[1-(3,4-dichloro-benzenesulfonyl)-3-oxo-1,2,3,4-tetrahydro-quinoxalin-2-yl]-N-{4-[(4-methyl-piperazin-1-yl)-phenyl-methyl]-cyclohexyl}-acetamide

(71) 4-(3,4-dichloro-benzenesulfonyl)-3-{2-[4-(morpholin-4-yl-phenyl-methyl)piperidin-1-yl]-2-oxo-ethyl}-3,4-dihydro-1H-quinoxalin-2-one

(72) 4-(3,4-dichlorophenylsulfonyl)-3-(2-(4-(1-morpholino-2-phenylethyl)piperidin-1-yl)-2-oxoethyl)-3,4-dihydroquinoxalin-2(1H)-one

(73) 2-[1-(3,4-dichloro-benzenesulfonyl)-pyrrolidin-2-yl]-N-[4-(morpholin-4-yl-phenyl-methyl)-cyclohexylmethyl]-acetamide

(74) 2-[1-(3,4-dichloro-benzenesulfonyl)-pyrrolidin-2-yl]-N-[4-(1-morpholin-4-yl-3-phenyl-propyl)-cyclohexylmethyl]-acetamide

(75) 2-[1-(3,4-dichloro-benzenesulfonyl)-pyrrolidin-2-yl]-N-[4-(3-phenyl-1-pyrrolidin-1-yl-propyl)-cyclohexylmethyl]-acetamide

(76) 2-[1-(3,4-dichloro-benzenesulfonyl)-pyrrolidin-2-yl]-N-[4-(phenyl-pyrrolidin-1-ylmethyl)-cyclohexylmethyl]-acetamide

(77) 2-(1-(3,4-dichlorophenylsulfonyl)pyrrolidin-2-yl)-N-(4-(3-phenyl-1-(piperidin-1-yl)propyl)cyclohexyl)acetamide

(78) 2-(1-(3,4-dichlorophenylsulfonyl)pyrrolidin-2-yl)-N-(4-(1-morpholino-3-phenylpropyl)cyclohexyl)acetamide

(79) 2-[1-(3,4-dichloro-benzenesulfonyl)-pyrrolidin-2-yl]-N-{4-[(4-methyl-piperazin-1-yl)-phenyl-methyl]-cyclohexyl}-acetamide

(80) 2-[1-(3,4-dichloro-benzenesulfonyl)-pyrrolidin-2-yl]-1-[4-(morpholin-4-yl-phenylmethyl)-piperidin-1-yl]-ethanone;

(81) 2-(1-(3,4-dichlorophenylsulfonyl)pyrrolidin-2-yl)-1-(4-(1-morpholino-2-phenylethyl)piperidin-1-yl)ethanone;

(82) 2-[1-(3,4-dichloro-benzenesulfonyl)-piperidin-2-yl]-N-[4-(morpholin-4-yl-phenylmethyl)-cyclohexylmethyl]-acetamide

(83) 2-[1-(3,4-dichloro-benzenesulfonyl)-piperidin-2-yl]-N-[4-(1-morpholin-4-yl-3-phenyl-propyl)-cyclohexylmethyl]-acetamide

(84) 2-[1-(3,4-dichloro-benzenesulfonyl)-piperidin-2-yl]-N-[4-(3-phenyl-1-pyrrolidin-1-yl-propyl)-cyclohexylmethyl]-acetamide

(85) 2-[1-(3,4-dichloro-benzenesulfonyl)-piperidin-2-yl]-N-[4-(phenyl-pyrrolidin-1-ylmethyl)-cyclohexylmethyl]-acetamide

(86) 2-[1-(3,4-dichloro-benzenesulfonyl)-piperidin-2-yl]-N-[4-(3-phenyl-1-piperidin-1-yl-propyl)-cyclohexyl]-acetamide

(87) 2-[1-(3,4-dichloro-benzenesulfonyl)-piperidin-2-yl]-N-[4-(1-morpholin-4-yl-3-phenyl-propyl)-cyclohexyl]-acetamide

(88) 2-[1-(3,4-dichloro-benzenesulfonyl)-piperidin-2-yl]-N-{4-[(4-methyl-piperazin-1-yl)-phenyl-methyl]-cyclohexyl}-acetamide
(89) 2-[1-(3,4-dichloro-benzenesulfonyl)-piperidin-2-yl]-1-[4-(morpholin-4-yl-phenylmethyl)-piperidin-1-yl]-ethanone;
(90) 2-(1-(3,4-dichlorophenylsulfonyl)piperidin-2-yl)-1-(4-(1-morpholino-2-phenylethyl)piperidin-1-yl)ethanone;
(91) 1-(3,4-dichlorophenylsulfonyl)-N-(4-((dimethylamino)(phenyl)methyl)cyclohexyl)indoline-2-carboxamide
(92) 1-(3,4-dichlorophenylsulfonyl)-N-(4-((dimethylamino)(3-fluorophenyl)methyl)cyclohexyl)indoline-2-carboxamide
(93) 1-(3,4-dichlorophenylsulfonyl)-N-(4-(1-(dimethylamino)-3-phenylpropyl)cyclohexyl)indoline-2-carboxamide
(94) 1-(3,4-dichlorophenylsulfonyl)-N-(4-((dimethylamino)(4-fluorophenyl)methyl)cyclohexyl)indoline-2-carboxamide
(95) 1-(3,4-dichlorophenylsulfonyl)-N-((4-((dimethylamino)(phenyl)methyl)cyclohexyl)methyl)indoline-2-carboxamide
(96) 1-(3,4-dichlorophenylsulfonyl)-N-((4-(1-(dimethylamino)-3-phenylpropyl)cyclohexyl)methyl)indoline-2-carboxamide
(97) 1-(3,4-dichlorophenylsulfonyl)-N-(2-(4-(1-(dimethylamino)-3-phenylpropyl)cyclohexyl)ethyl)indoline-2-carboxamide
(98) 2-(2-(3,4-dichloro-N-methylphenylsulfonamido)phenyl)-N-(2-(4-((dimethylamino)(phenyl)methyl)cyclohexyl)ethyl)acetamide
(99) 2-(2-(3,4-dichloro-N-methylphenylsulfonamido)phenyl)-N-(2-(4-(1-(dimethylamino)-3-phenylpropyl)cyclohexyl)ethyl)acetamide
(100) N-(2-(4-((dimethylamino)(phenyl)methyl)cyclohexyl)ethyl)-1-(4-methoxy-N-methylphenylsulfonamido)cyclohexanecarboxamide
(101) 2-(1-(2,4-dichlorophenylsulfonyl)-3-oxopiperazin-2-yl)-N-(4-(morpholino(phenyl)methyl)cyclohexyl)acetamide
(102) 2-(1-(2,4-dichlorophenylsulfonyl)-3-oxopiperazin-2-yl)-N-(4-(phenyl(pyrrolidin-1-yl)methyl)cyclohexyl)acetamide
(103) 2-(1-(3,4-dichlorophenylsulfonyl)-3-oxo-1,2,3,4-tetrahydroquinoxalin-2-yl)-N-(4-(phenyl(pyrrolidin-1-yl)methyl)cyclohexyl)acetamide
(104) 2-(1-(3,4-dichlorophenylsulfonyl)pyrrolidin-2-yl)-N-(4-(morpholino(phenyl)methyl)cyclohexyl)acetamide
(105) 2-(1-(3,4-dichlorophenylsulfonyl)pyrrolidin-2-yl)-N-(4-(phenyl(pyrrolidin-1-yl)methyl)cyclohexyl)acetamide
(106) 2-(1-(3,4-dichlorophenylsulfonyl)piperidin-2-yl)-N-(4-(morpholino(phenyl)methyl)cyclohexyl)acetamide
(107) 2-(1-(3,4-dichlorophenylsulfonyl)piperidin-2-yl)-N-(4-(phenyl(pyrrolidin-1-yl)methyl)cyclohexyl)acetamide
(108) 1-(4-((4-methylpiperazin-1-yl)(phenyl)methyl)piperidin-1-yl)-2-(1-(3-(trifluoromethyl)phenylsulfonyl)piperidin-2-yl)ethanone;
(109) 1-(4-((4-fluorophenyl)(4-methylpiperazin-1-yl)methyl)piperidin-1-yl)-2-(1-(3-(trifluoromethyl)phenylsulfonyl)piperidin-2-yl)ethanone;
(110) N-(3-(4-((3-fluorophenyl)(4-methylpiperazin-1-yl)methyl)piperidin-1-yl)-3-oxo-1-phenylpropyl)naphthalene-2-sulfonamide
(111) 1-(4-(1-(4-methylpiperazin-1-yl)-2-phenylethyl)piperidin-1-yl)-2-(1-(3-(trifluoromethyl)phenylsulfonyl)piperidin-2-yl)ethanone;
(112) 1-(4-(1-(4-methylpiperazin-1-yl)-3-phenylpropyl)piperidin-1-yl)-2-(1-(3-(trifluoromethyl)phenylsulfonyl)piperidin-2-yl)ethanone;
(113) N-(3-(4-(1-(4-methylpiperazin-1-yl)-3-phenylpropyl)piperidin-1-yl)-3-oxo-1-phenylpropyl)naphthalene-2-sulfonamide
(114) N-(3-(4-((4-methylpiperazin-1-yl)(phenyl)methyl)piperidin-1-yl)-3-oxo-1-phenylpropyl)naphthalene-2-sulfonamide
(115) 1-(4-((3-fluorophenyl)(4-methylpiperazin-1-yl)methyl)piperidin-1-yl)-2-(1-(3-(trifluoromethyl)phenylsulfonyl)piperidin-2-yl)ethanone;
(116) N-(3-(4-(1-(4-methylpiperazin-1-yl)-2-phenylethyl)piperidin-1-yl)-3-oxo-1-phenylpropyl)naphthalene-2-sulfonamide
(117) N-(3-(4-((4-fluorophenyl)(4-methylpiperazin-1-yl)methyl)piperidin-1-yl)-3-oxo-1-phenylpropyl)naphthalene-2-sulfonamide
(118) 3-(1-(4-chloro-2,5-dimethylphenylsulfonyl)piperidin-2-yl)-1-(4-(1-(4-methyl-piperazin-1-yl)-2-phenylethyl)piperidin-1-yl)propan-1-one
(119) 3-(1-(4-chloro-2,5-dimethylphenylsulfonyl)piperidin-2-yl)-1-(4-(1-(4-methyl-piperazin-1-yl)-3-phenylpropyl)piperidin-1-yl)propan-1-one
(120) 3-(1-(4-chloro-2,5-dimethylphenylsulfonyl)piperidin-2-yl)-1-(4-((3-fluorophenyl)(4-methylpiperazin-1-yl)methyl)piperidin-1-yl)propan-1-one
(121) 3-(1-(4-chloro-2,5-dimethylphenylsulfonyl)piperidin-2-yl)-1-(4-((4-fluorophenyl)(4-methylpiperazin-1-yl)methyl)piperidin-1-yl)propan-1-one, and
(122) 3-(1-(4-chloro-2,5-dimethylphenylsulfonyl)piperidin-2-yl)-1-(4-((4-methyl-piperazin-1-yl)(phenyl)methyl)piperidin-1-yl)propan-1-one, in the form of the racemate; of the enantiomers, diastereoisomers, mixtures of the enantiomers or diastereoisomers or of an individual enantiomer or diastereoisomer; of the bases and/or salts of physiologically acceptable acids.

The invention further provides a process for the preparation of a substituted sulfonamide derivative according to the invention. In order to prepare compounds of formula Ia wherein q denotes 0, amines of the general formula II are reacted with acids of the general formula III with the addition of a coupling reagent.

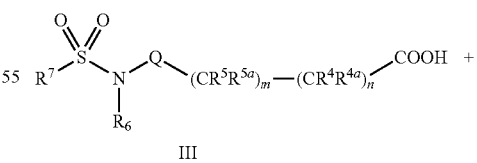

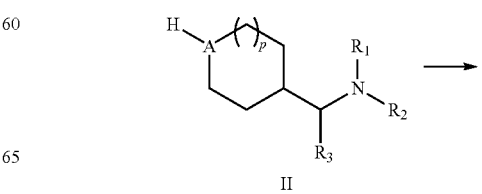

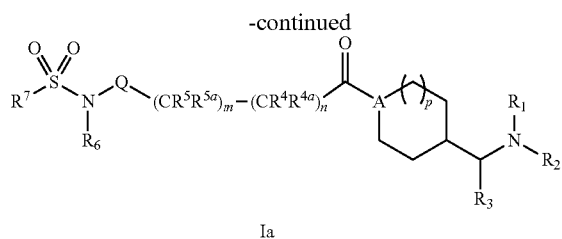

Ia

In this reaction, the carboxylic acids III are reacted in an amide formation using primary or secondary amines of the general formula II in the presence of water-removing agents such as sodium or magnesium sulfate, phosphorus oxide or reagents such as, for example, CDI, DCC (optionally polymer-bonded), TBTU, EDCI, PyBOP or PFPTFA, also in the presence of HOAt or HOBt and of an organic base, for example DIPEA or pyridine, in an organic solvent such as THF, dichloromethane, diethyl ether, dioxane, DMF or acetonitrile, to give the products of the general formula I.

In order to prepare compounds of the general formula Ib wherein q denotes 1, amines of the general formula II are reacted with isocyanates or carbamates of formula IV.

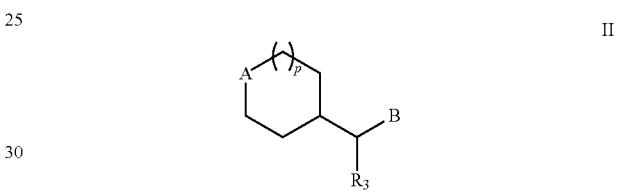

IV

In this reaction, carbamates are reacted with amines of the general formula II in an organic solvent, for example 1,4-dioxane, to give the compounds of the general formula Ib. Alternatively, the amines of the general formula II are reacted in an organic solvent with isocyanates of the general formula IV, optionally in the presence of at least one base, preferably in the presence of at least one base selected from the group consisting of triethylamine, 4,4-dimethylaminopyridine and diisopropylethylamine, to give the compounds of the general formula Ib, which are optionally purified and/or isolated.

The amine structural units of the general formula II that are used can be prepared by the following processes, for example. According to the process designated Process A hereinbelow it is possible to prepare amine structural units wherein A in the structural unit of the general formula II represents $CHNH_2$ or $(CH_2)_n NH_2$.

II

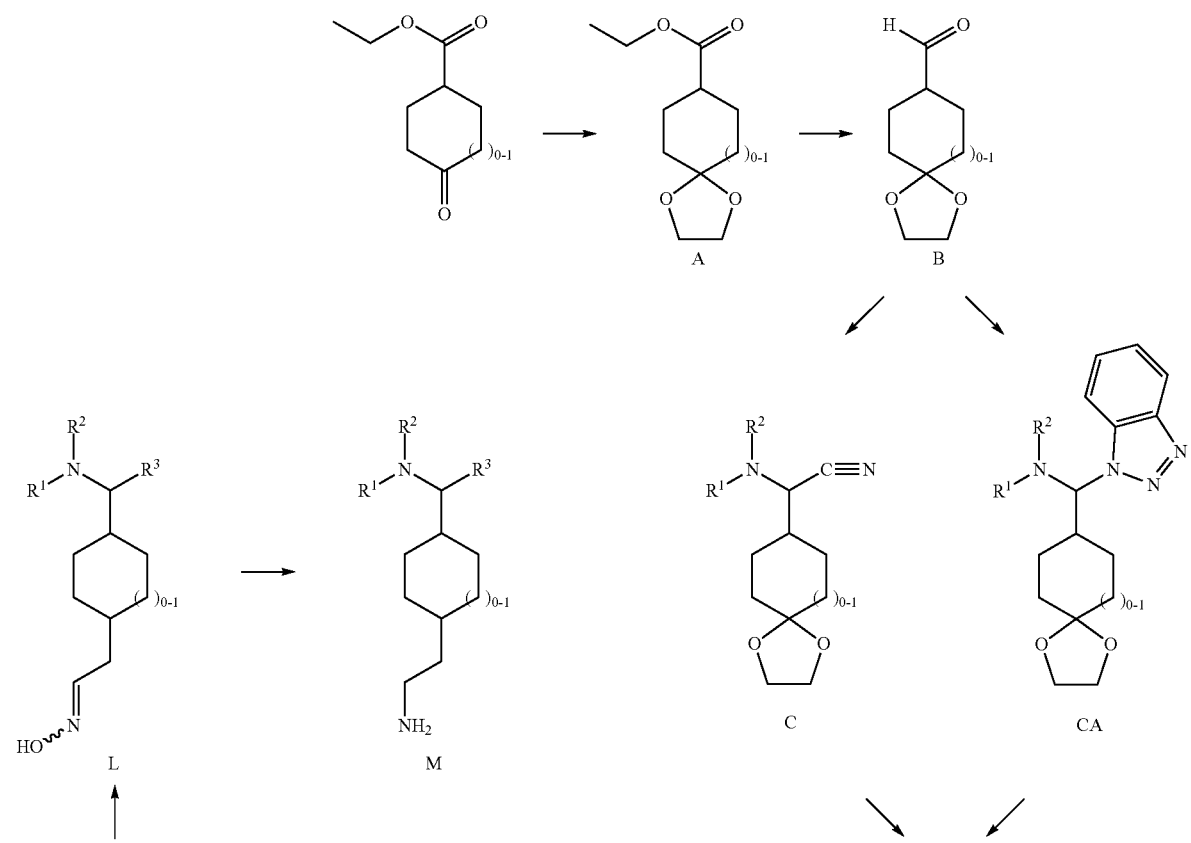

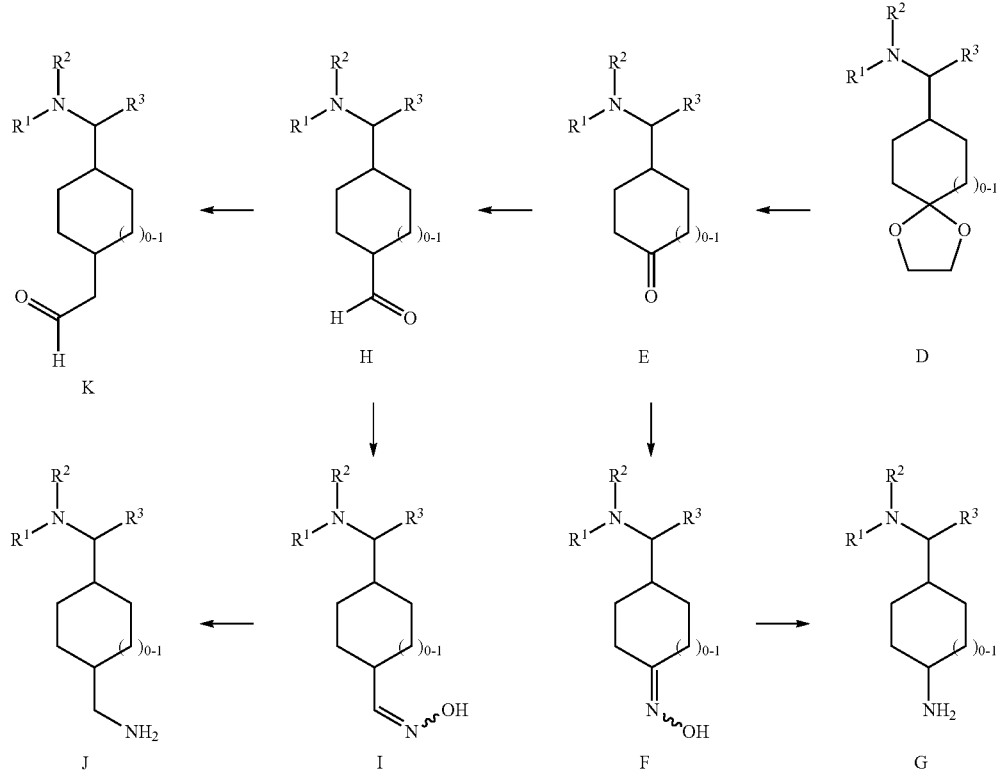

In this process, ethyl 4-oxocyclohexanecarboxylate or cyclopentanone-3-carboxylic acid ethyl ester is reacted in an acetal-forming reaction with a diol derivative in an organic solvent, such as benzene, toluene or xylene, dichloromethane, cyclohexane or ethanol, optionally with the addition of catalytic amounts of p-toluenesulfonic acid, camphorsulfonic acid, pyridinium tosylate or acetic acid, possibly also in the presence of a water-removing reagent, such as sulfuric acid, sodium or magnesium sulfate, molecular sieve or phosphorus oxides, at a temperature of from RT to the reflux temperature of the organic solvent in question, to give the acetal A.

The prior esterification of cyclopentanone-3-carboxylic acid to give cyclopentanone-3-carboxylic acid ethyl ester can be carried out by reacting cyclopentanone-3-carboxylic acid with ethanol using sulfuric acid or hydrochloric acid or by reacting cyclopentanone-3-carboxylic acid with iodoethane using sodium ethanolate or caesium carbonate in DMF.

The acetal A can be reduced to the aldehyde B in a reduction reaction with a reducing agent, for example diisobutylaluminium hydride, sodium aluminium hydride or borane-THF complex, in diethyl ether, dichloromethane, THF, hexane, toluene or a mixture of the mentioned solvents, at a temperature of from −95° C. to −20° C.

The aldehyde B can be converted into the nitrile C by addition of an amine and a cyanide source. The reaction can take place in one or two stages. In the two-stage variant, a nitrile alcohol is first formed and isolated. The formation of the nitrile alcohol can be carried out by reacting the aldehyde B with HCN, KCN or NaCN. Suitable solvents are water, methanol, ethanol, THF, piperidine, diethyl ether or a mixture of these solvents. When NaCN and KCN are used, the required cyanide is typically liberated by addition of, for example, sodium hydrogen sulfite, sulfuric acid, acetic acid or hydrochloric acid. Trimethylsilyl cyanide, for example, is also suitable as the nitrile source. The liberation of the cyanide can be effected, for example, by boron trifluoride etherate, InF$_3$ or HCl. Typical solvents here are water or toluene. An example of a further suitable cyanide source is (cyano-C) diethylaluminium. THF, toluene or a mixture of the two solvents can be used as solvent.

The reaction temperature can be from −78° C. to +25° C. for all variants. Particularly suitable solvents for the reaction of the nitrile alcohol with the amine are alcohols, such as methanol or ethanol. The reaction temperature can be from 0° C. to +25° C. In the single-stage variant, the nitrile alcohol formed as primary product is formed and reacted with the amine in situ. In a variant of the reaction procedure, the aldehyde B is reacted with an amine and 1H-benzotriazole in an aminal-forming reaction to give the benzotriazole aminal CA. The benzotriazole aminal can be present in equilibrium in both the 1H and the 2H form. Suitable solvents include benzene, toluene, ethanol, diethyl ether or THF. It may be necessary to use a Dean-Stark water separator, molecular sieve or other water-removing means. The reaction time is normally from 1 to 20 hours at a reaction temperature of from +20° C. to +110° C. Both the nitrile C and the benzotriazole aminal CA can be reacted with metal organyls, such as magnesium, zinc or lithium organyls, in organic solvents, for example diethyl ether, dioxane or tetrahydrofuran, to give aminoacetals D.

The amine ketones E are obtained in an acetal cleavage reaction under acidic conditions. Suitable acids are both inorganic Brönstedt or Lewis acids, such as hydrochloric acid, sulfuric acid, ammonium chloride or hydrogen sulfate, or AlI$_3$, as well as organic acids, such as, for example, p-toluenesulfonic acid, acetic acid, oxalic acid, trifluoromethanesulfonic acid, formic acid, trifluoroacetic acid or citric acid.

The reaction can be carried out in various solvents, such as, for example, toluene, THF, chloroform, DCM, xylene, acetonitrile, water, dioxane, acetone, diethyl ether or ethyl acetate, at temperatures of from −10° C. to room temperature. The aldehyde H is obtained from the amine ketone E in a Wittig reaction using phosphorylides and a strong base, for example potassium tert-butoxide, n-butyllithium, s-butyllithium, phenyllithium, lithium diisopropylamide or lithium hexamethyldisilazide, in organic solvents, such as THF, diethyl ether, cyclohexane, toluene or a mixture of the solvents, at a temperature of from −78° C. to +30° C., after acidic working up of the reaction mixture.

To synthesize the aldehyde K, the Wittig reaction is repeated under identical conditions using the aldehyde H as starting compound. For synthesis of structural units in which A represents $(CH_2)_nNH_2$ wherein n>1, the step is repeated n times.

The ketone E is reacted in an oxime-forming reaction with hydroxylamine hydrochloride, sulfate or acetate in an organic solvent, for example ethanol, methanol, 2-propanol, 2-methyl-propan-2-ol or acetonitrile, with the addition of an organic base, such as, for example, pyridine, sodium acetate, triethylamine, 4-dimethylaminopyridine or potassium tert-butoxide, or of an aqueous solution of an inorganic base, such as sodium hydrogen carbonate, sodium carbonate, potassium carbonate, sodium hydroxide or potassium hydroxide, or basic ion exchanger Amberlyst, to give the oximes F.

The aldehydes H and K can likewise be reacted under the same conditions to give the oximes I and L, respectively. The amines G can be obtained by a reduction reaction of the oximes F with a reducing agent, such as, for example, LiAlH₄, sodium, zinc, borane-dimethyl sulfide, sodium borohydride/nickel(II) chloride hexahydrate, in ethanol, methanol, glacial acetic acid, THF, diethyl ether or dioxane, or by catalytic hydrogenation with palladium or platinum oxide as heterogeneous catalyst, with the addition of HCl in an alcohol, such as methanol or ethanol. The amines J and M can be prepared from the respective oximes I and L under the same conditions.

Amine structural units of the general formula II wherein A denotes NH can be prepared by the following process:

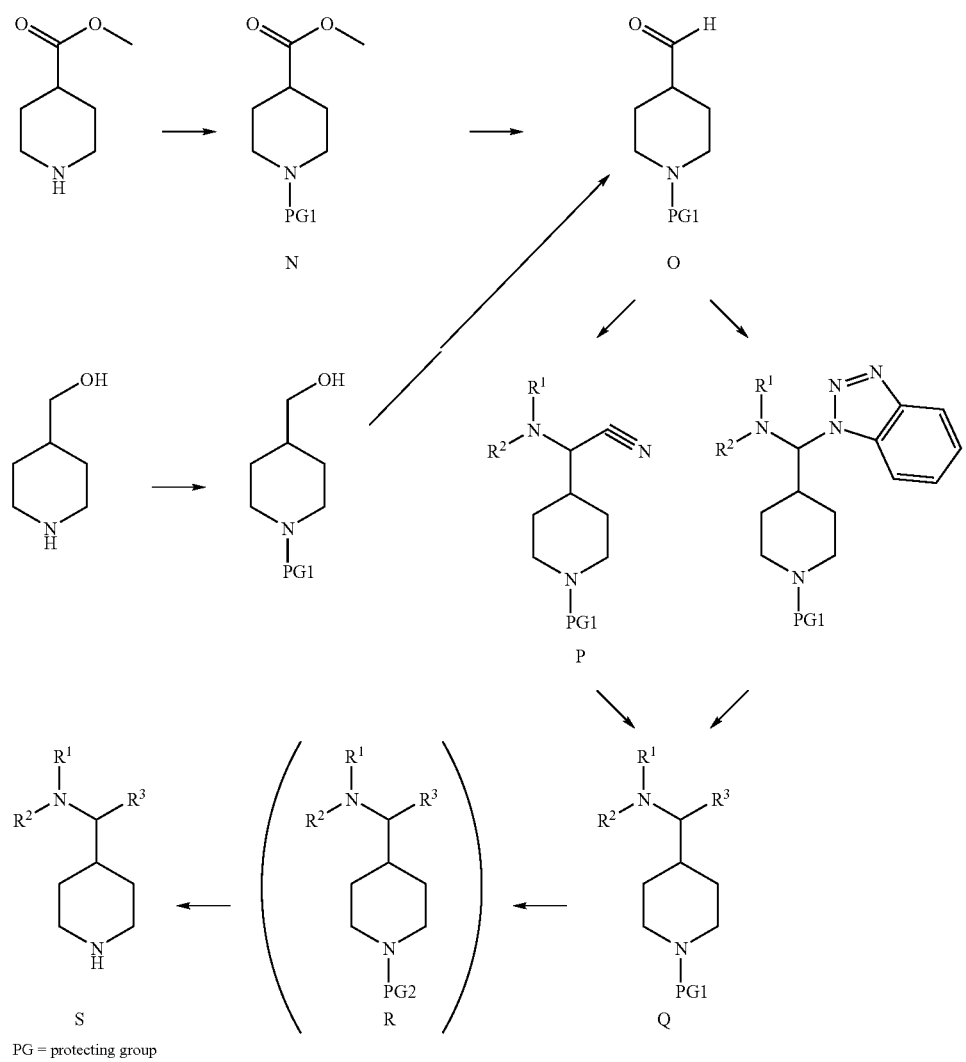

PG = protecting group

Isonipecotic acid methyl ester or piperidin-4-ylmethanol is subjected to an alkylation reaction. p-Methoxybenzyl halides are particularly suitable as the alkylating reagent. The reaction can be carried out in from 1 to 72 hours by reacting p-methoxybenzyl chloride or bromide in THF, benzene, toluene, dimethylformamide, acetonitrile, dichloromethane, ethanol or acetone using a base, such as, for example, triethylamine, diisopropylethylamine, potassium carbonate or sodium carbonate, at a temperature of from +20° C. to +80° C. Alternatively, it is also possible to introduce a BOC group as protecting group by reaction with di-tert-butyl dicarbonate in an organic solvent such as THF, dichloromethane, methanol, dioxane, DMF or diethyl ether, optionally with the use of an inorganic base, such as sodium carbonate, sodium hydrogen carbonate or sodium hydroxide, or of an organic base, such as triethylamine, diisopropylethylamine or n-butyllithium, at a temperature of from −78° C. to room temperature.

The synthesis steps for reducing the ester N to the aldehyde O, reaction of the aldehyde O to the aminonitrile P and reaction with a metal organyl to give the protected amine Q are carried out analogously to the synthesis steps described for compounds A→B→C→D.

The protected piperidin-4-ylmethanol can be reacted to give the aldehyde O by the use of reagents, such as PCC, periodinane, IBX, TPAP, NMO, $MnO_2$ or oxalyl chloride, optionally also in the presence of molecular sieve or of a base, such as triethylamine, in an organic solvent such as dichloromethane, DMSO, methanol, ethanol, diethyl ether, THF, DMF, DME, at a temperature of from −78° C. to the reflux temperature of the organic solvent in question.

An alternative route for reacting the compounds Q to give the compound R is carried out analogously to the synthesis steps described for compounds B→CA→D.

The debenzylation of the compounds Q to give the piperidine derivative S can be carried out directly with ceric ammonium nitrate in acetonitrile at room temperature in the course of from 0.5 to 2 hours, or indirectly by reaction of the compound Q with chloroformic acid benzyl ester in dichloromethane at room temperature to give the compounds of the general formula R.

Various methods are known for deprotecting the compounds R, for example in the case of the use of benzyl carbamate protecting groups, such as, for example, catalytic hydrogenation with Pd or $Pd(OH)_2$ as catalyst in solvents such as alcohols, preferably methanol or ethanol, THF, dioxane, ethyl acetate, DMF or mixtures of the mentioned solvents. Auxiliary reagents such as, for example, acetic acid, acetic acid chloride, HCl, ammonium acetate, ammonium formate, water, potassium carbonate, potassium hydroxide, cyclohexene or 1,4-cyclohexadiene can optionally be added. Also known is deprotection with the aid of trimethylsilyl iodide in organic solvents, such as chloroform, dichloromethane or acetonitrile. It is further possible to use methylsulfonic acid with the addition of anisole in chloroform or dichloromethane, or alternatively HCl gas in chloroform or dichloromethane, or HBr in glacial acetic acid.

BOC protecting groups can be removed by reaction with HCl in organic solvents, such as dioxane, methanol, ethanol, acetonitrile or ethyl acetate, or by reaction with trifluoroacetic acid or methanesulfonic acid in dichloromethane or THF at a temperature of from 0° C. to 110° C. and with a reaction time of from 0.5 to 20 hours. The acid structural units used can be obtained by various methods.

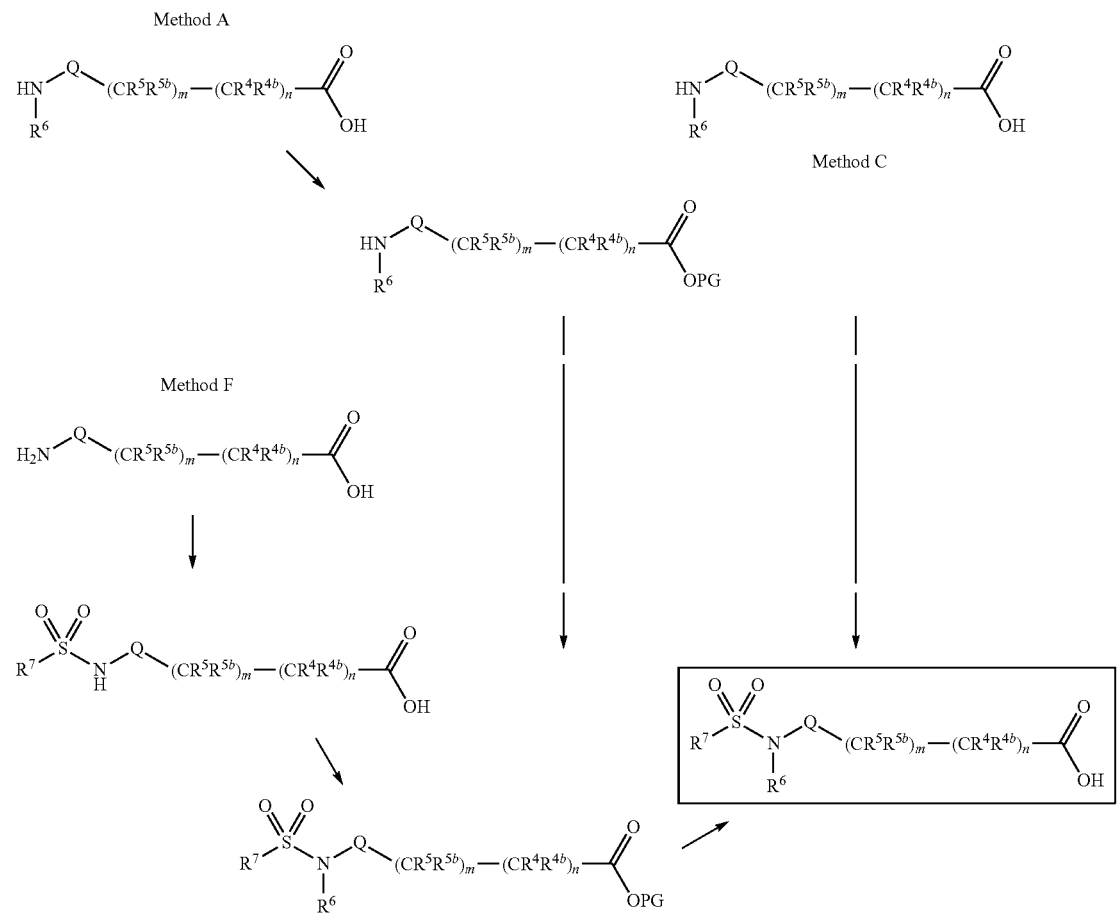

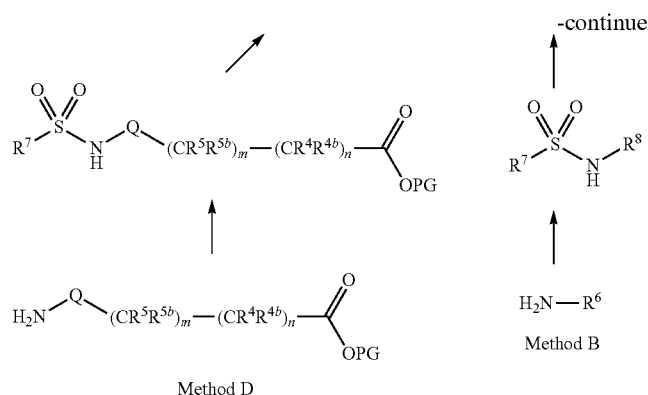

Method D

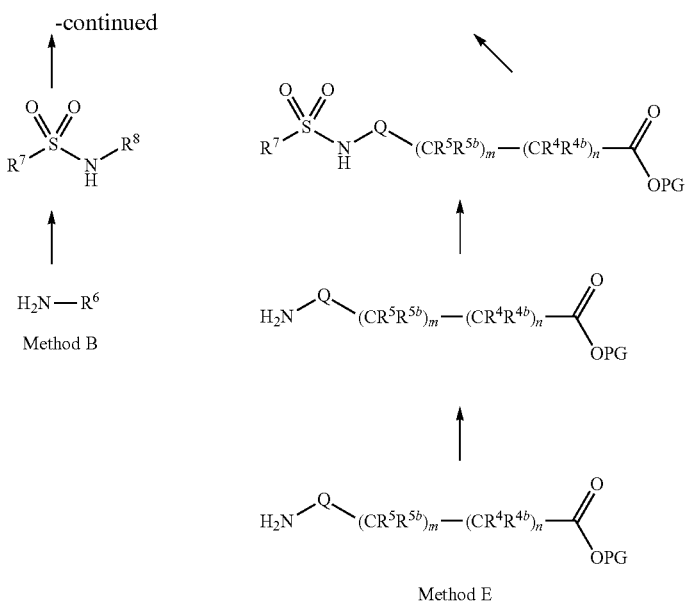

Method B

Method E

Method A

The amino acids used are esterified using water-removing reagents, for example inorganic acids such as $H_2SO_4$ or phosphorus oxides or organic reagents such as thionyl chloride, in organic solvents such as THF, diethyl ether, methanol, ethanol or DCM, to give the amino acid esters, which are then converted into the sulfonylated amino acid esters in a sulfonylation with sulfonyl chlorides or bromides or pentafluorophenolates $R_3SO_2X$ (X=Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, DCM or THF. The sulfonylated amino acid esters react in an ester cleavage using organic acids, such as trifluoroacetic acid, or aqueous inorganic acids, such as hydrochloric acid, or using aqueous inorganic bases such as lithium hydroxide, potassium hydroxide, sodium hydroxide, sodium carbonate, sodium hydrogen carbonate, potassium carbonate in organic solvents such as methanol, dioxane, DCM, THF, diethyl ether or these solvents in the form of mixtures, to give the sulfonylated amino acids.

Method B

The primary amines used are first converted into the sulfonamides in a sulfonylation reaction with sulfonyl chlorides or bromides or pentafluorophenolates $R_3SO_2X$ (X Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, DCM or THF. The sulfonamides are then converted into the sulfonylated amino acid esters in a second step by an alkylation reaction with haloalkanes or alcohols in solvents, such as acetone, DMF, DCM, THF, hexane, toluene, methanol or water, using inorganic or organic bases, such as potassium carbonate, n-butyllithium, lithium diisopropylamide, sodium hydride, sodium hydroxide, sodium methanolate, diisopropylethylamine and triethylamine, and optionally with the aid of reagents, such as triphenylphosphine, diisopropyl azodicarboxylate, diethyl azodicarboxylate, (cyanomethylene)trimethylphosphonate, at a temperature of from −78° C. to +80° C.

The sulfonylated amino acid esters react in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents such as methanol, dioxane, DCM, THF, diethyl ether or these solvents in the form of mixtures, to give the sulfonylated amino acids.

Method C

The amino acids used are converted into the sulfonylated amino acids in a sulfonylation reaction with sulfonyl chlorides or bromides or pentafluorophenolates $R_3SO_2X$ (X=Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, DCM or THF.

Method D

The amino acid esters used are converted into the sulfonylated amino acid esters in a sulfonylation reaction with sulfonyl chlorides or bromides or pentafluorophenolates $R_3SO_2X$ (X=Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, dichloromethane or tetrahydrofuran. The sulfonylated amino acid esters are then converted into the sulfonylated amino acid esters in a second step by an alkylation reaction with haloalkanes or alcohols in solvents, such as acetone, DMF, DCM, THF, hexane, toluene, methanol or water, using inorganic or organic bases, such as potassium carbonate, n-butyllithium, lithium diisopropylamide, sodium hydride, sodium hydroxide, sodium methanolate, diisopropylethylamine and triethylamine, and optionally with the aid of reagents, such as triphenylphosphine, diisopropyl azodicarboxylate, diethyl azodicarboxylate, (cyanomethylene)trimethylphosphonate, at a temperature of from −78° C. to +80° C. The sulfonylated amino acid esters react in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents such as methanol, dioxane, dichloromethane, THF, diethyl ether or these solvents in the form of mixtures, to give the sulfonylated amino acids.

Method E

The amino acids used are esterified using water-removing reagents, for example inorganic acids such as $H_2SO_4$ or phosphorus oxides or organic reagents such as thionyl chloride, in organic solvents such as THF, diethyl ether, methanol, ethanol or DCM, to give the amino acid esters, which are then reacted in a sulfonylation with sulfonyl chlorides or bromides or pentafluorophenolates $R_3SO_2X$ (X=Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, DCM or THF, to give the sulfonylated amino acid esters. The sulfonylated amino acid esters are then converted into the alkylated, sulfonylated amino acid esters by an alkylation reaction with haloalkanes or alcohols in solvents, such as acetone, DMF, DCM, THF, hexane, toluene, methanol or water, using inorganic or organic bases, such as potassium carbonate, n-butyllithium, lithium diisopropylamide, sodium hydride, sodium hydroxide, sodium methanolate, diisopropylethylamine and triethylamine, and optionally with the aid of reagents, such as triphenylphosphine, diisopropyl azodicarboxylate, diethyl azodicarboxylate, (cyanomethylene)trimethylphosphonate, at a temperature of from −78° C. to +80° C. The sulfonylated amino acid esters react in an ester cleavage using organic acids, such as trifluoroacetic acid, or aqueous inorganic acids, such as hydrochloric acid, or using aqueous inorganic bases such as lithium hydroxide, potassium hydroxide, sodium hydroxide, sodium carbonate, sodium hydrogen carbonate, potassium carbonate in organic solvents such as methanol, dioxane, DCM, THF, diethyl ether or these solvents in the form of mixtures, to give the sulfonylated amino acids.

Method F

The amino acids are first converted into the sulfonylated amino acids in a sulfonylation reaction with sulfonyl chlorides or bromides or pentafluorophenolates $R_3SO_2X$ (X=Cl, Br, OPFP), optionally in the presence of an organic or inorganic base, for example potassium carbonate, sodium hydrogen carbonate, diisopropylethylamine, triethylamine, pyridine, diethylamine or DBU, preferably in an organic solvent, for example acetonitrile, dichloromethane or tetrahydrofuran. The sulfonylated amino acids are then converted into the alkylated, sulfonylated amino acid esters by an alkylation reaction with haloalkanes or alcohols in solvents, such as acetone, DMF, DCM, THF, hexane, toluene, methanol or water, using inorganic or organic bases, such as potassium carbonate, n-butyllithium, lithium diisopropylamide, sodium hydride, sodium hydroxide, sodium methanolate, diisopropylethylamine and triethylamine, and optionally with the aid of reagents, such as triphenylphosphine, diisopropyl azodicarboxylate, diethyl azodicarboxylate, (cyanomethylene)trimethylphosphonate, at a temperature of from −78° C. to +80° C. The sulfonylated amino acid esters react in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents such as methanol, dioxane, dichloromethane, THF, diethyl ether or these solvents in the form of mixtures, to give the sulfonylated amino acids.

If the substituted sulfonamide compounds according to the invention are obtained after their preparation in the form of a mixture of their stereoisomers, preferably in the form of their racemates or other mixtures of their various enantiomers and/or diastereoisomers, these can be separated and optionally isolated by conventional processes known to the person skilled in the art. Examples which may be mentioned include chromatographic separation processes, in particular liquid chromatography processes under normal pressure or under elevated pressure, preferably MPLC and HPLC processes, as well as fractional crystallisation processes. It is thereby possible to separate from one another in particular individual enantiomers, for example by means of HPLC on chiral stationary phase, or diastereoisomeric salts formed by means of crystallisation with chiral acids, for example (+)-tartaric acid, (−)-tartaric acid or (+)-10-camphorsulfonic acid.

It has been shown that the substances according to the invention are B1 receptor antagonists. The compounds are therefore suitable for the treatment of acute, visceral, chronic or neuropathic pain and inflammatory pain, but also for the treatment of respiratory diseases, diabetes, respiratory diseases, inflammatory intestinal diseases, neurological diseases, inflammations of the skin, rheumatic diseases, septic shock, reperfusion syndrome, obesity and as an angiogenesis inhibitor.

The substances according to the invention are suitable as pharmaceutical active ingredients in medicaments. The invention accordingly further provides medicaments comprising at least one substituted sulfonamide derivative according to the invention as well as, optionally, suitable additives and/or auxiliary substances and/or optionally further active ingredients.

The medicaments according to the invention optionally comprise, in addition to at least one substituted sulfonamide derivative according to the invention, suitable additives and/or auxiliary substances, that is to say also carriers, fillers, solvents, diluents, colourings and/or binders, and can be administered as liquid medicament forms in the form of injection solutions, drops or juices, or as semi-solid medicament forms in the form of granules, tablets, pellets, patches, capsules, plasters or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or into the eyes. Formulations in the form of tablets, coated tablets, capsules, granules, drops, juices and syrups are suitable for oral administration, and solutions, suspensions, readily reconstitutable dry formulations and sprays are suitable for parenteral, topical and inhalatory administration. Substituted sulfonamide derivatives according to the invention in a depot, in dissolved form or in a plaster, optionally with the addition of agents which promote penetration through the skin, are suitable formulations for percutaneous administration. Forms of preparation which can be used orally or percutaneously can release the substituted sulfonamide derivatives according to the invention in a delayed manner. In principle, other further active ingredients known to the person skilled in the art can be added to the medicaments according to the invention.

The amount of active ingredient to be administered to the patient varies according to the weight of the patient, the mode of administration, the indication and the severity of the disease. From 0.005 to 20 mg/kg, preferably from 0.05 to 5 mg/kg, of at least one substituted sulfonamide derivative according to the invention are conventionally administered.

The medicament can comprise a substituted sulfonamide derivative according to the invention as a pure diastereoisomer and/or enantiomer, as a racemate or as a non-equimolar or equimolar mixture of the diastereoisomers and/or enantiomers.

The invention also provides the use of a substituted sulfonamide derivative according to the invention in the preparation of a medicament for the treatment of pain, in particular of acute, visceral, chronic or neuropathic pain and inflammatory pain.

The invention further provides the use of a substituted sulfonamide derivative according to the invention in the preparation of a medicament for the treatment of respiratory diseases.

The substituted sulfonamide derivatives of the general formula I are also suitable for the treatment of depression, urinary incontinence, diarrhoea, pruritus, alcohol and drug abuse, lack of drive, migraine, diabetes, inflammatory intestinal diseases, neurological diseases, inflammations of the skin, rheumatic diseases, septic shock, reperfusion syndrome, obesity, as an angiogenesis inhibitor and for anxiolysis.

The invention accordingly also provides the use of a substituted sulfonamide derivative of the general formula I in the preparation of a medicament for the treatment of depression, urinary incontinence, diarrhoea, pruritus, alcohol and drug abuse, lack of drive, migraine, diabetes, inflammatory intestinal diseases, neurological diseases, inflammations of the skin, rheumatic diseases, septic shock, reperfusion syndrome, obesity, as an angiogenesis inhibitor and for anxiolysis.

EXAMPLES

The following examples which follow are intended to explain the invention but do not limit the invention. The yields of the compounds prepared have not been optimized. All the temperatures are uncorrected.

The term "RT" means room temperature, "conc." means concentrated, "d" means days, "min" means minutes, "h" means hours, "M" is a concentration in mol/l, "MeOH" means methanol, "THF" means tetrahydrofuran, "aq." means aqueous, "sat." means saturated, "EtOAc" means ethyl acetate, "NaHCO$_3$ solution" means sodium hydrogen carbonate solution, "DCM" means dichloromethane, "CHCl$_3$" means chloroform, "DMF" means N,N-dimethylformamide, "Et$_2$O" means diethyl ether, "Et$_3$N" means triethylamine, "Na$_2$SO$_4$" means sodium sulfate, "NH$_4$Cl solution" means sat. aq. ammonium chloride solution.

The chemicals and solvents employed were obtained commercially from the conventional suppliers (Acros, Avocado, Aldrich, Bachem, Fluka, Lancaster, Maybridge, Merck, Sigma, TCI, etc.) or were synthesised by methods known in the literature. Silica gel 60 (0.040-0.063 mm) from E. Merck, Darmstadt was employed as the stationary phase for the column chromatography.

Abbreviations
TBTU=O-(benzotriazol-1-yl)-N,N,N',N'-tetramethyluronium tetrafluoroborate
CDI=1,1'-carbonyldiimidazole
DCC=dicyclohexylcarbodiimide
EDCI=1-ethyl-3-(3-dimethylaminopropyl)carbodiimide
HOAt=1-hydroxy-7-azabenzotriazole
DIPEA=N,N-diisopropylamine
HOBt=1-hydroxybenzotriazole
EDCI=N-(3-dimethylaminopropyl)-N'-ethylcarbodiimide hydrochloride
PyBOP=benzotriazol-1-yl-oxy-tris-pyrrolidino-phosphonium hexafluorophosphate
PFPTFA=pentafluorophenyltrifluoroacetyl
OPFP=O-pentafluorophenyl
DBU=1,8-diazabicyclo[5.4.0]undec-7-ene
AcOH=acetic acid
DIBAL-H=diisobutylaluminium hydride
EtOH=ethanol
HBt=1H-benzotriazole
KtOBu=potassium tert-butoxide
LAH=lithium aluminium hydride
PG=protecting group
TEA=triethylamine
TFA=trifluoroacetic acid
p-TosOH=p-toluenesulfonic acid The thin-layer chromatography investigations were carried out using HPTLC precoated plates, silica gel 60 F 254 from E. Merck, Darmstadt. The mixing ratios of solvents, mobile phases or for chromatography investigations are always stated in volume/volume.

| Amine structural units used | |
|---|---|
| No. | Name |
| A1 | 4-(dimethylamino-phenyl-methyl)-cyclohexylamine |
| A2 | 4-[dimethylamino-(4-fluorophenyl)-methyl]-cyclohexylamine |
| A3 | 4-[dimethylamino-(3-fluorophenyl)-methyl]-cyclohexylamine |
| A4 | 4-(dimethylamino-thiophen-2-yl-methyl)-cyclohexylamine |
| A5 | 4-(1-dimethylamino-3-phenyl-propyl)-cyclohexylamine |
| A6 | 4-(1-morpholin-4-yl-3-phenyl-propyl)-cyclohexylamine |
| A7 | 4-(3-phenyl-1-piperidin-1-yl-propyl)-cyclohexylamine |
| A8 | 4-[(4-methyl-piperazin-1-yl)-phenyl-methyl]-cyclohexylamine |
| A9 | 4-(phenyl-pyrrolidin-1-yl-methyl)-cyclohexylamine |
| A10 | 4-(phenyl-piperidin-1-yl-methyl)-cyclohexylamine |
| A11 | 4-(morpholin-4-yl-phenyl-methyl)-cyclohexylamine |
| A12 | [(4-aminomethyl-cyclohexyl)-phenyl-methyl]-dimethylamine |
| A13 | [(4-aminomethyl-cyclohexyl)-(4-fluorophenyl)-methyl]-dimethylamine |
| A14 | [(4-aminomethyl-cyclohexyl)-(3-fluorophenyl)-methyl]-dimethylamine |
| A15 | [(4-aminomethyl-cyclohexyl)-(4-chlorophenyl)-methyl]-dimethylamine |
| A16 | [(4-aminomethyl-cyclohexyl)-thiophen-2-yl-methyl]-dimethylamine |
| A17 | [1-(4-aminomethyl-cyclohexyl)-3-phenyl-propyl]-dimethylamine |
| A18 | C-[4-(morpholin-4-yl-phenyl-methyl)-cyclohexyl]-methylamine |
| A19 | C-[4-(1-morpholin-4-yl-3-phenyl-propyl)-cyclohexyl]-methylamine |
| A20 | C-[4-(phenyl-pyrrolidin-1-yl-methyl)-cyclohexyl]-methylamine |
| A21 | C-[4-(3-phenyl-1-pyrrolidin-1-yl-propyl)-cyclohexyl]-methylamine |
| A22 | 2-[4-(dimethylamino-phenyl-methyl)-cyclohexyl]-ethylamine |
| A23 | 2-{4-[dimethylamino-(4-fluorophenyl)-methyl]-cyclohexyl}-ethylamine |
| A24 | 2-{4-[dimethylamino-(3-fluorophenyl)-methyl]-cyclohexyl}-ethylamine |
| A25 | 2-{4-[(4-chlorophenyl)-dimethylamino-methyl]-cyclohexyl}-ethylamine |
| A26 | 2-[4-(dimethylamino-thiophen-2-yl-methyl)-cyclohexyl]-ethylamine |
| A27 | {1-[4-(2-amino-ethyl)-cyclohexyl]-3-phenyl-propyl}-dimethylamine |
| A28 | N,N-dimethyl-1-phenyl-1-(piperidin-4-yl)methanamine |
| A29 | 4-(phenyl-piperidin-4-yl-methyl)-morpholine |
| A30 | 4-(2-phenyl-1-piperidin-4-yl-ethyl)-morpholine |
| A31 | 1-((3-fluorophenyl)(piperidin-4-yl)methyl)-4-methylpiperazine |
| A32 | 1-((4-fluorophenyl)(piperidin-4-yl)methyl)-4-methylpiperazine |
| A33 | 1-methyl-4-(phenyl(piperidin-4-yl)methyl)piperazine |
| A34 | 1-methyl-4-(2-phenyl-1-(piperidin-4-yl)ethyl)piperazine |
| A35 | 1-methyl-4-(3-phenyl-1-(piperidin-4-yl)propyl)piperazine |

Synthesis of the Amine Structural Units
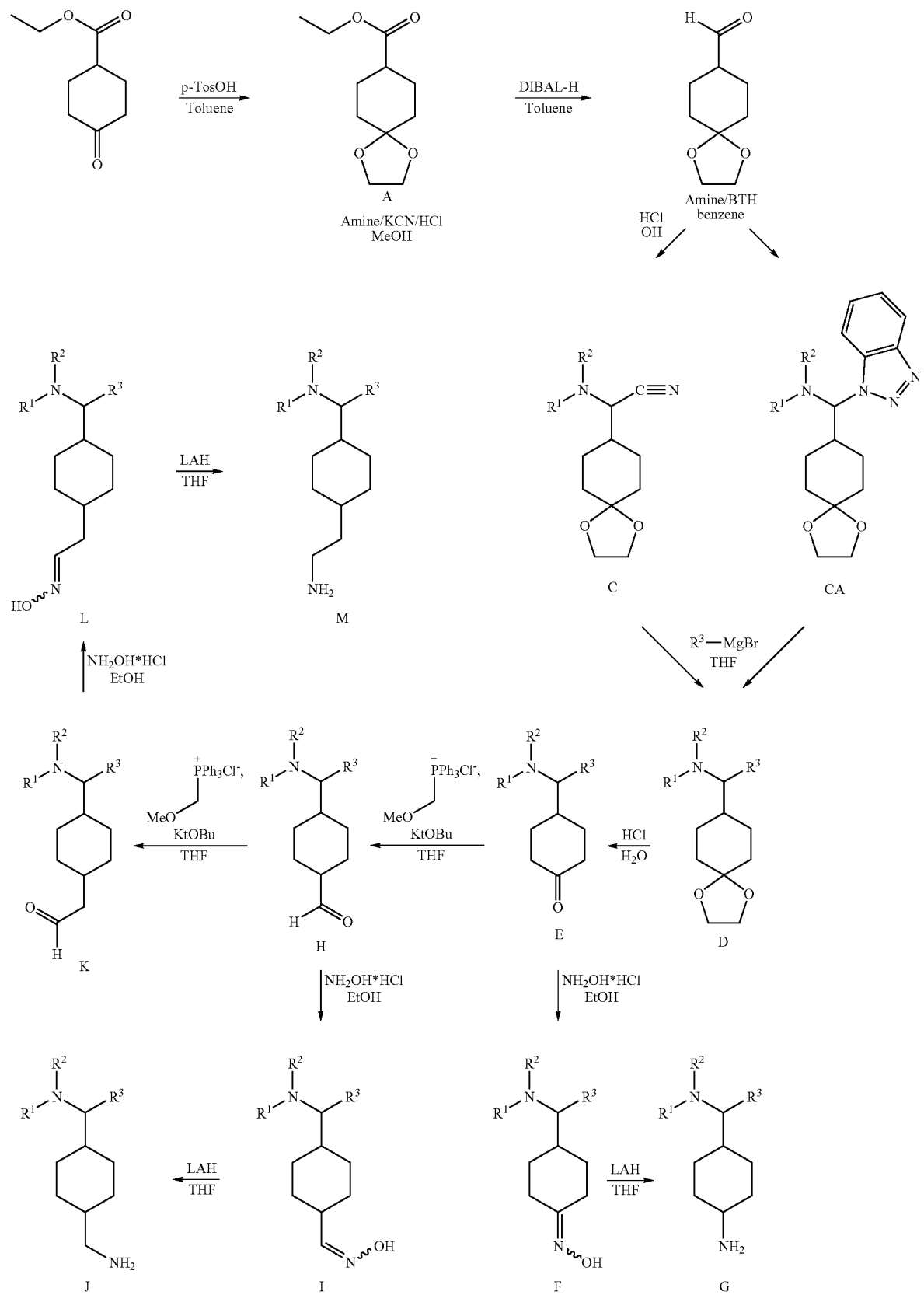

a) Synthesis of the Cyclohexanones Used

The ketones were obtained from commercially available 4-oxo-cyclohexanecarboxylic acid ethyl ester in a multi-stage synthesis. The yields of the prepared compounds are not optimised. All temperatures are uncorrected.

1,4-Dioxa-spiro[4.5]decane-8-carboxylic acid ethyl ester

4-Oxo-cyclohexanecarboxylic acid ethyl ester (52.8 g, 0.31 mol, Merck, order no. 814249), ethylene glycol (67.4 g, 1.08 mol) and p-toluenesulfonic acid (0.7 g) in toluene (160 ml) were stirred for 20 h at RT and the reaction solution was poured into diethyl ether (300 ml) and washed with water, sodium hydrogen carbonate solution and sodium chloride solution. The solution was dried (sodium sulfate) and concentrated in vacuo, and the colourless liquid that remained was processed further without being purified.

Yield: 66.5 g (100%)

$^1$H-NMR (CDCl$_3$): 1.24 (t, 3H); 1.53 (m, 2H); 1.76 (m, 4H); 1.92 (m, 2H); 2.31 (m, 1H); 3.91 (s, 4H); 4.11 (q, 2H).

$^{13}$C-NMR (CDCl$_3$): 14.28 (q); 26.32 (t); 33.76 (t); 41.59 (d); 60.14 (t); 64.21 (t); 107.90 (d); 174.77 (s).

1,4-Dioxa-spiro[4.5]decane-8-carbaldehyde

Diisobutylaluminium hydride (1.5 M solution in toluene, 102 ml, 153 mmol) was added dropwise at −70 to −65° C., under argon, to a solution of 1,4-dioxa-spiro-[4.5]decane-8-carboxylic acid ethyl ester (32.13 g, 150 mmol) in abs. toluene (160 ml), and stirring was carried out for 30 min. The mixture was then quenched at −70 to −60° C. by addition of methanol (80 ml). The reaction solution was heated to RT, saturated sodium chloride solution (100 ml) was added, and the reaction solution was filtered off with suction over kieselguhr. Kieselguhr was washed twice with ethyl acetate, and the aqueous solution was separated and extracted twice with ethyl acetate. The combined organic extracts were washed with saturated sodium chloride solution, dried over sodium sulfate and concentrated in vacuo.

Yield: 24.01 g (94%), yellow oil $^1$H-NMR (CDCl$_3$): 1.54 (m, 2H); 1.74 (m, 4H); 1.91 (m, 2H); 2.21 (m, 1H); 3.91 (s, 4H); 9.60 (s, 1H).

$^{13}$C-NMR (CDCl$_3$): 23.35 (t); 33.37 (t); 48.18 (d); 64.30 (t); 107.89 (d); 203.51 (s).

Amino-(1,4-dioxa-spiro[4.5]dec-8-yl)-acetonitrile

Dimethylamino-(1,4-dioxa-spiro[4.5]dec-8-yl)-acetonitrile (R$^1$=Me, R$^2$=Me)

40% aqueous dimethylamine solution (85 ml, 0.67 mol), 1,4-dioxa-spiro-[4.5]decane-8-carbaldehyde (240 g, 0.141 mol) and potassium cyanide (22.05 g, 0.338 mol) were added, while cooling with ice, to a mixture of 4 N hydrochloric acid (37 ml) and methanol (22 ml). The mixture was stirred for 4 d at room temperature; water (80 ml) was added and then the mixture was extracted with diethyl ether (4×100 ml). The organic phase was dried over sodium sulfate and concentrated in vacuo, and the product was obtained in the form of a white solid.

Yield: 25.2 g (81%); melting point: 48-51° C.

$^1$H-NMR (CDCl$_3$): 1.23-2.03 (m, 9H); 2.28 (s, 6H); 3.16 (d, 1H); 3.93 (m, 4H).

$^{13}$C-NMR (CDCl$_3$): 26.67 (t); 27.93 (t); 33.87 (t); 36.94 (d); 41.90 (q); 64.30 (t); 64.36 (t); 108.33 (d); 115.94 (s).

Morpholino-(1,4-dioxa-spiro[4.5]dec-8-yl)-acetonitrile (NR$^1$R$^2$=morpholine)

KCN (0.17 mol) and morpholine (14.7 g, 0.17 mol) were added to a solution of 1,4-dioxa-spiro[4.5]decane-8-carboxaldehyde (0.141 mol) in a mixture of ethanol (141 ml) and water (70 ml), and stirring was carried out for 72 h at 25° C. After addition of ethyl acetate (700 ml), the organic phase was separated off and washed in succession with water (4×150 ml) and aqueous FeSO$_4$ solution (4×150 ml). The organic phase was separated off and dried over Na$_2$SO$_4$ and then filtered off. The solvent was removed in vacuo, and the product was used in the next stage without being purified further.

Pyrrolidino-(1,4-dioxa-spiro[4.5]dec-8-yl)-acetonitrile (NR$^1$R$^2$=pyrrolidine)

KCN (0.17 mol) and pyrrolidine (12.07 g, 0.17 mol) were added to a solution of 1,4-dioxa-spiro[4.5]decane-8-carboxaldehyde (0.141 mol) in a mixture of ethanol (141 ml) and water (70 ml), and stirring was carried out for 72 h at 25° C. After addition of ethyl acetate (700 ml), the organic phase was separated off and washed in succession with water (4×150 ml) and aqueous FeSO$_4$ solution (4×150 ml). The organic phase was separated off and dried over Na$_2$SO$_4$ and then filtered off. The solvent was removed in vacuo, and the product was used in the next stage without being purified further.

Piperidino-(1,4-dioxa-spiro[4.5]dec-8-yl)-acetonitrile (NR$^1$R$^2$=piperidine)

KCN (0.17 mol) and piperidine (14.45 g, 0.17 mol) were added to a solution of 1,4-dioxa-spiro[4.5]decane-8-carboxaldehyde (0.141 mol) in a mixture of ethanol (141 ml) and water (70 ml), and stirring was carried out for 72 h at 25° C. After addition of ethyl acetate (700 ml), the organic phase was separated off and washed in succession with water (4×150 ml) and aqueous FeSO$_4$ solution (4×150 ml). The organic phase was separated off and dried over Na$_2$SO$_4$ and then filtered off. The solvent was removed in vacuo, and the product was used in the next stage without being purified further.

[(1,4-Dioxa-spiro[4.5]dec-8-yl)-phenyl-methyl]-dimethyl-amine (R$^1$=Me, R$^2$=Me, R$^3$=phenyl)

A solution of the aminonitrile (23.56 g, 105 mmol) in abs. THF (100 ml) was added dropwise, under argon and while cooling with ice, to a 25% solution of phenylmagnesium chloride (144 ml, 262.5 mmol) in THF, and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried (sodium sulfate) and concentrated.

Yield: 28.9 g (100%).

$^{13}$C-NMR (CDCl$_3$): 27.05; 28.13; 34.48; 34.57; 36.94 (C$_8$); 41.64 (N(CH$_3$)$_2$); 64.15; 74.33 (CH); 109.02 (C$_5$); 126.70 (C$_{arom}$); 127.49 (C$_{arom}$); 129.12 (C$_{arom}$); 136.57 (C$_{arom}$).

[(1,4-Dioxa-spiro[4.5]dec-8-yl)-4-fluorophenyl-methyl]-dimethylamine (R$^1$=Me, R$^2$=Me, R$^3$=4-fluorophenyl)

A solution of the aminonitrile (19.89 g, 88 mmol) in abs. THF (160 ml) was added dropwise, under argon and while cooling with ice, to a 1 M solution of 4-fluorophenylmagnesium bromide in THF (220 ml, 220 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried (sodium sulfate) and concentrated.

Yield: 31 g (>100%)

$^{13}$C-NMR (CDCl$_3$): 26.68 (t); 28.11 (t); 34.43 (t); 34.55 (t); 37.37 (d); 41.68 (q); 64.12 (t); 73.65 (d); 108.88 (d); 114.23 (d); 114.44 (d); 130.27; 130.35; 132.43; 160.36 (s); 162.78 (s).

[(1,4-Dioxa-spiro[4.5]dec-8-yl)-3-fluorophenyl-methyl]-dimethyl-amine (R$^1$=Me, R$^2$=Me, R$^3$=3-fluorophenyl)

A solution of the aminonitrile (23.45 g, 104 mmol) in abs. THF (100 ml) was added dropwise, under argon and while cooling with ice, to a 1 M solution of 3-fluorophenylmagnesium bromide in THF (208 ml, 208 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried and concentrated.

Yield: 30.33 g (99%).

$^1$H-NMR (CDCl$_3$): 1.12 (m, 1H); 1.26 (m, 1H); 1.46-1.81 (m, 7H); 2.10 (s, 6H); 3.10 (d, 1H); 3.90 (m, 4H); 6.85 (m, 3H); 7.27 (m, 1H).

$^{13}$C-NMR (CDCl$_3$): 26.80 (t); 28.08 (t); 34.48 (t); 34.45 (t); 34.59 (t); 37.26 (d); 41.71 (q); 64.19 (t); 74.04 (t); 108.91 (d); 113.51 (d); 113.71 (d); 115.52 (d); 115.72 (d); 124.83 (d); 128.82 (d); 128.90 (d); 139.66 (s); 161.15 (s); 163.58 (s).

[(4-Chlorophenyl)-(1,4-dioxa-spiro[4.5]dec-8-yl)-methyl]-dimethyl-amine (R$^1$=Me, R$^2$=Me, R$^3$=4-chlorophenyl)

A solution of the aminonitrile (22.43 g, 100 mmol) in abs. diethyl ether (100 ml) was added dropwise, under argon and while cooling with ice, to a 1 M solution of 4-chlorophenylmagnesium bromide in diethyl ether (200 ml, 200 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried and concentrated.

Yield: 30.9 g (100%)

$^{13}$C-NMR (CDCl$_3$): 26.65 (t); 28.11 (t); 34.46 (t); 34.60 (t); 37.28 (d); 41.76 (q); 64.17 (t); 73.80 (d); 108.88 (s); 127.72 (d); 129.53 (d); 132.39 (d); 135.33 (d).

[(1,4-Dioxa-spiro[4.5]dec-8-yl)-thiophen-2-yl-methyl]-dimethylamine (R$^1$=Me, R$^2$=Me, R$^3$=2-thienyl)

A solution of the aminonitrile (2.24 g, 10 mmol) in abs. THF (10 ml) was added dropwise, under argon and while cooling with ice, to a 1 M solution of thiophen-2-yl-magnesium bromide in THF (20 ml, 20 mmol), and stirring was carried out for 20 h at RT. For working up the reaction mixture, saturated ammonium chloride solution (10 ml) and water (10 ml) were added, while cooling with ice, and extraction with diethyl ether (3×10 ml) was carried out. The organic phase was washed with water and saturated sodium chloride solution, dried and concentrated.

Yield: 2.8 g (100%)

$^{13}$C-NMR (CDCl$_3$): 27.72 (t); 27.88 (t); 34.27 (t); 39.28 (d); 41.10 (q); 64.11 (t); 68.89 (d); 108.88 (s); 123.55 (d); 125.88 (d); 127.53 (d); 139.50 (s).

[1-(1,4-Dioxa-spiro[4.5]dec-8-yl)-3-phenyl-propyl]-dimethylamine (R$^1$=Me, R$^2$=Me, R$^3$=phenethyl)

A solution of the aminonitrile (21.93 g, 97 mmol) in abs. THF (180 ml) was added dropwise, under argon and while cooling with ice, to a 1 M solution of phenylethyl-magnesium chloride in THF (242 ml, 242 mmol), and stirring was carried out for 20 h at RT. For working up the reaction mixture, saturated ammonium chloride solution (100 ml) and water (100 ml) were added, while cooling with ice, and extraction with diethyl ether (3×100 ml) was carried out. The organic phase was washed with water and saturated sodium chloride solution, dried and concentrated.

Yield: 34 g (>100%).

$^{13}$C-NMR (CDCl$_3$): 27.43 (t); 28.95 (t); 29.42 (t); 34.82 (t); 35.40 (t); 38.76 (d); 41.16 (q); 64.17 (t); 67.41 (d); 108.86 (s); 125.41 (d); 127.66 (d); 128.11 (d); 142.69 (s).

[(1,4-Dioxa-spiro[4.5]dec-8-yl)-phenyl-methyl]-morpholine (NR$^1$R$^2$=morpholine, R$^3$=phenyl)

A 25% solution of phenylmagnesium chloride (144 ml, 262.5 mmol) in THF was added dropwise at 0° C., under argon, to a solution of the aminonitrile (105 mmol) in THF (100 ml), and then stirring was carried out for a further 20 h at 25° C. After addition of a saturated aqueous NH$_4$Cl solution (200 ml), the reaction mixture was extracted with ethyl acetate (3×100 ml). The combined organic phases were then washed with water and with saturated aqueous NaCl solution. The organic phase was separated off and dried over Na$_2$SO$_4$ and filtered off. The solvent was removed in vacuo, and the product was purified by column chromatography (2-5% methanol/dichloromethane).

[1-(1,4-Dioxa-spiro[4.5]dec-8-yl)-3-phenyl-propyl]-morpholine (NR$^1$R$^2$=morpholine, R$^3$=phenethyl)

A 1 M solution of phenylethylmagnesium chloride in THF (262 ml, 262 mmol) was added dropwise at 0° C., under argon, to a solution of the aminonitrile (105 mmol) in THF (100 ml), and then stirring was carried out for a further 20 h at 25° C. After addition of a saturated aqueous NH$_4$Cl solution (200 ml), the reaction mixture was extracted with ethyl acetate (3×100 ml). The combined organic phases were then washed with water and with saturated aqueous NaCl solution. The organic phase was separated off and dried over Na$_2$SO$_4$ and filtered off. The solvent was removed in vacuo, and the product was purified by column chromatography (2-5% methanol/dichloromethane).

[(1,4-Dioxa-spiro[4.5]dec-8-yl)-phenyl-methyl]-pyrrolidine (NR$^1$R$^2$=pyrrolidine, R$^3$=phenyl)

A 25% solution of phenylmagnesium chloride (144 ml, 262.5 mmol) in THF was added dropwise at 0° C., under argon, to a solution of the aminonitrile (105 mmol) in THF (100 ml), and then stirring was carried out for a further 20 h at 25° C. After addition of a saturated aqueous NH$_4$Cl solution (200 ml), the reaction mixture was extracted with ethyl acetate (3×100 ml). The combined organic phases were then washed with water and with saturated aqueous NaCl solution. The organic phase was separated off and dried over Na$_2$SO$_4$ and filtered off. The solvent was removed in vacuo, and the product was purified by column chromatography (2-5% methanol/dichloromethane).

[1-(1,4-Dioxa-spiro[4.5]dec-8-yl)-3-phenyl-propyl]-pyrrolidine (NR$^1$R$^2$=pyrrolidine, R$^3$=phenethyl)

A 1 M solution of phenylethylmagnesium chloride in THF (262 ml, 262 mmol) in THF was added dropwise at 0° C., under argon, to a solution of the aminonitrile (105 mmol) in THF (100 ml), and then stirring was carried out for a further 20 h at 25° C. After addition of a saturated aqueous NH$_4$Cl solution (200 ml), the reaction mixture was extracted with ethyl acetate (3×100 ml). The combined organic phases were then washed with water and with saturated aqueous NaCl solution. The organic phase was separated off and dried over Na$_2$SO$_4$ and filtered off. The solvent was removed in vacuo, and the product was purified by column chromatography (2-5% methanol/dichloromethane).

[1-(1,4-Dioxa-spiro[4.5]dec-8-yl)-3-phenyl-propyl]-piperidine (NR$^1$R$^2$=piperidine, R$^3$=phenethyl)

A 1 M solution of phenylethylmagnesium chloride in THF (262 ml, 262 mmol) in THF was added dropwise at 0° C., under argon, to a solution of the aminonitrile (105 mmol) in THF (100 ml), and then stirring was carried out for a further 20 h at 25° C. After addition of a saturated aqueous NH$_4$Cl solution (200 ml), the reaction mixture was extracted with ethyl acetate (3×100 ml). The combined organic phases were then washed with water and with saturated aqueous NaCl solution. The organic phase was separated off and dried over Na$_2$SO$_4$ and filtered. The solvent was removed in vacuo, and the product was purified by column chromatography (2-5% methanol/dichloromethane).

1-[1,4-Dioxaspiro[4.5]dec-8-yl)phenylmethyl]piperidine (NR$^1$R$^2$=piperidine, R$^3$=phenyl)

A solution of piperidino-(1,4-dioxa-spiro[4.5]dec-8-yl)-acetonitrile (2.8 g, 10.6 mmol) in absolute tetrahydrofuran (10 ml) was added dropwise, under argon and while cooling with ice, to a 2 M solution of phenylmagnesium chloride in tetrahydrofuran (13 ml, 26.4 mmol), and stirring was carried out for 20 h at room temperature. Saturated ammonium chloride solution (10 ml) and water (10 ml) were then added dropwise to the reaction mixture, while cooling with ice, and the solution was extracted with diethyl ether (3×30 ml). The combined organic phases were washed with water (30 ml) and saturated ammonium chloride solution (30 ml), dried over sodium sulfate and concentrated in vacuo.
Yield: 3.20 g (96%), yellow, tacky solid
Melting point: could not be determined
$^1$H-NMR (DMSO-d$_6$): 0.08-2.30 (m, 19H); 3.12 (d, 1H, J=9.9 Hz); 3.81 (s, 4H); 7.00-7.80 (m, 5H).

4-(Dimethylamino-phenyl-methyl)-cyclohexanone (R$^1$=Me, R$^2$=Me, R$^3$=phenyl)

The ketal (28.9 g, 0.105 mol) was dissolved in water (44 ml); conc. hydrochloric acid (64 ml) was added thereto, and stirring was carried out for 20 h at RT. The reaction mixture was extracted by shaking with diethyl ether (2×100 ml), and the aqueous phase was rendered alkaline with 5N NaOH, while cooling with ice, extracted with DCM (3×100 ml), dried and concentrated. The ketone was isolated in the form of a colourless oil.
Yield: 18.2 g (75%)

$^1$H-NMR (CDCl$_3$): 1.20 (1H, m); 1.33 (1H, m); 1.74 (1H, m); 2.17 (6H, s, N(CH$_3$)$_2$); 2.70 (6H, m); 3.10 (1H, d, C$_8$—H); 7.07 (2H, m, C$_{arom}$—H); 7.23 (3H, m, C$_{arom}$—H).
$^{13}$C-NMR (CDCl$_3$): 29.13; 30.56; 36.90 (C$_4$); 40.61; 40.82; 41.89 (N(CH$_3$)$_2$); 73.79 (CH); 127.05 (C$_{arom}$); 127.67 (C$_{arom}$); 129.00 (C$_{arom}$); 136.13 (C$_{arom}$); 211.79 (C=O).

4-[Dimethylamino-(4-fluorophenyl)-methyl]-cyclohexanone (R$^1$=Me, R$^2$=Me, R$^3$=4-fluorophenyl)

The crude product of the ketal (26 g, 88 mmol) was dissolved in water (40 ml); conc. hydrochloric acid (59 ml) was added thereto, and stirring was carried out for 20 h at RT. The reaction mixture was extracted with diethyl ether (2×100 ml), and the aqueous phase was rendered alkaline with 5N NaOH, while cooling with ice, extracted with DCM (3×100 ml), dried and concentrated.
Yield: 21.36 g (98%)
$^{13}$C-NMR (CDCl$_3$): 28.90 (t); 30.48 (t); 37.00 (t); 40.49 (t); 40.72 (t); 41.79 (q); 72.98 (d); 114.42 (d); 114.62 (d); 130.20 (d); 130.28 (d); 131.88 (s); 160.50 (s); 162.93 (s); 211.44 (s).

4-[Dimethylamino-(3-fluorophenyl)-methyl]-cyclohexanone (R$^1$=Me, R$^2$=Me, R$^3$=3-fluorophenyl)

The ketal (30.3 g, 103 mmol) was dissolved in water (44 ml); conc. hydrochloric acid (64 ml) was added thereto, and stirring was carried out for 20 h at RT. The reaction mixture was extracted by shaking with diethyl ether (2×100 ml), and the aqueous phase was rendered alkaline with 5N NaOH, while cooling with ice, extracted with DCM (3×100 ml), dried and concentrated. The ketone was isolated in the form of a colourless oil.
Yield: 22.4 g (87%); melting point: 72-75° C.
$^{13}$C-NMR (CDCl$_3$): 28.97 (t); 30.44 (t); 36.90 (t); 40.52 (t); 40.75 (t); 41.82 (q); 73.37 (d); 113.84; 114.06; 115.42; 115.62; 124.71; 129.03; 129.11; 139.00; 139.06; 161.16; 163.60; 211.40 (s).

4-[(4-Chloro-phenyl)-dimethylamino-methyl]-cyclohexanone (R$^3$=4-chloro-phenyl)

The ketal (30.98 g, 100 mmol) was dissolved in water (44 ml); conc. hydrochloric acid (64 ml) was added thereto, and stirring was carried out for 20 h at RT. The reaction mixture was extracted by shaking with diethyl ether (2×100 ml), and the aqueous phase was rendered alkaline with 5N NaOH, while cooling with ice, extracted with DCM (3×100 ml), dried and concentrated. The ketone was isolated in the form of an oil.
Yield: 21.9 g (82%)
$^{13}$C-NMR (CDCl$_3$): 28.88 (t); 30.45 (t); 36.89 (t); 40.49 (t); 40.74 (t); 41.83 (q); 73.12 (d); 127.87 (d); 130.16 (d); 132.75 (d); 13470 (s); 211.35 (s).

4-(Dimethylamino-thiophen-2-yl-methyl)-cyclohexanone (R$^1$=Me, R$^2$=Me, R$^3$=2-thienyl)

The ketal (2.80 g, 10 mmol) was dissolved in water (4.4 ml); conc. hydrochloric acid (6.4 ml) was added thereto, and stirring was carried out for 20 h at RT. The reaction mixture was extracted by shaking with diethyl ether (2×10 ml), and the aqueous phase was rendered alkaline with 5N NaOH, while cooling with ice, extracted with DCM (3×10 ml), dried and concentrated. The ketone was isolated in the form of an oil.
Yield: 1.79 g (75%)

$^{13}$C-NMR (CDCl$_3$): 30.02 (t); 30.18 (t); 38.84 (t); 40.29 (t); 39.28 (d); 41.17 (q); 68.24 (d); 123.88 (d); 126.01 (d); 126.34 (d); 138.77 (d); 211.49 (s).

4-(1-Dimethylamino-3-phenyl-propyl)-cyclohexanone (R$^1$=Me, R$^2$=Me, R$^3$=phenethyl)

The crude product of the ketal (29.6 g, 97 mmol) was dissolved in water (44 ml); conc. hydrochloric acid (64 ml) was added thereto, and stirring was carried out for 20 h at RT. The reaction mixture was extracted by shaking with diethyl ether (2×100 ml), and the aqueous phase was rendered alkaline with 5N NaOH, while cooling with ice, extracted with DCM (3×100 ml), dried and concentrated. The ketone was isolated in the form of a colorless oil.
Yield: 16.9 g (58%)
$^{13}$C-NMR (CDCl$_3$): 29.40 (t); 30.02 (t); 30.97 (t); 35.34 (t); 38.71 (t); 40.79 (t); 41.01 (t); 41.23 (q); 66.65 (d); 125.66 (d); 128.12 (d); 128.19 (d); 142.27 (s); 211.70 (s).

4-(Morpholino(phenyl)methyl)cyclohexanone (NR$^1$R$^2$=morpholine, R$^3$=phenyl)

Conc. HCl and water (1:1, 88 ml) were slowly added at 0° C. to the Grignard adduct (105 mmol), and stirring was carried out for 20 h at 25° C. The reaction solution was then extracted with ethyl acetate (2×100 ml). After addition of 5N sodium hydroxide solution to establish a basic pH value, extraction with dichloromethane (3×100 ml) was carried out. The combined organic phases were dried over Na$_2$SO$_4$ and filtered off. The solvent was removed in vacuo and the product was used in the next stage without being purified further.

4-(1-Morpholino-3-phenylpropyl)cyclohexanone (NR$^1$R$^2$=morpholine, R$^3$=phenethyl)

Conc. HCl and water (1:1, 88 ml) were slowly added at 0° C. to the Grignard adduct (105 mmol), and stirring was carried out for 20 h at 25° C. The reaction solution was then extracted with ethyl acetate (2×100 ml). After addition of 5N sodium hydroxide solution to establish a basic pH value, extraction with dichloromethane (3×100 ml) was carried out. The combined organic phases were dried over Na$_2$SO$_4$ and filtered off. The solvent was removed in vacuo and the product was used in the next stage without being purified further.

4-(Phenyl(pyrrolidin-1-yl)methyl)cyclohexanone (NR$^1$R$^2$=pyrrolidine, R$^3$=phenyl)

Conc. HCl and water (1:1, 88 ml) were slowly added at 0° C. to the Grignard adduct (105 mmol), and stirring was carried out for 20 h at 25° C. The reaction solution was then extracted with ethyl acetate (2×100 ml). After addition of 5N sodium hydroxide solution to establish a basic pH value, extraction with dichloromethane (3×100 ml) was carried out. The combined organic phases were dried over Na$_2$SO$_4$ and filtered off. The solvent was removed in vacuo and the product was used in the next stage without being purified further.

4-(3-Phenyl-1-(pyrrolidin-1-yl)propyl)cyclohexanone (NR$^1$R$^2$=pyrrolidine, R$^3$=phenethyl)

Conc. HCl and water (1:1, 88 ml) were slowly added at 0° C. to the Grignard adduct (105 mmol), and stirring was carried out for 20 h at 25° C. The reaction solution was then extracted with ethyl acetate (2×100 ml). After addition of 5N sodium hydroxide solution to establish a basic pH value, extraction with dichloromethane (3×100 ml) was carried out. The combined organic phases were dried over Na$_2$SO$_4$ and filtered off. The solvent was removed in vacuo and the product was used in the next stage without being purified further.

4-(3-Phenyl-1-(piperidin-1-yl)propyl)cyclohexanone (NR$^1$R$^2$=piperidine, R$^3$=phenethyl)

Conc. HCl and water (1:1, 88 ml) were slowly added at 0° C. to the Grignard adduct (105 mmol), and stirring was carried out for 20 h at 25° C. The reaction solution was then extracted with ethyl acetate (2×100 ml). After addition of 5N sodium hydroxide solution to establish a basic pH value, extraction with dichloromethane (3×100 ml) was carried out. The combined organic phases were dried over Na$_2$SO$_4$ and filtered off. The solvent was removed in vacuo and the product was used in the next stage without being purified further.

4-(Phenylpiperidin-1-yl-methyl)cyclohexanone (NR$^1$R$^2$=piperidine, R$^3$=phenyl)

A solution of 1-[1,4-dioxaspiro[4.5]dec-8-yl)phenylmethyl]piperidine (3.10 g, 9.8 mmol) in water (8 ml) and concentrated hydrochloric acid (12 ml) was stirred for 20 h at room temperature. The reaction mixture was washed with diethyl ether (2×20 ml), and the aqueous phase was adjusted to pH 12 with 5N sodium hydroxide solution, while cooling with ice, and extracted with dichloromethane (3×40 ml). The combined organic phases were dried over sodium sulfate and concentrated in vacuo.
Yield: 2.00 g (76%), yellowish solid
Melting point: 88-90° C.
$^1$H-NMR (DMSO-d$_6$): 1.00-1.56 (m, 10H); 2.02-2.50 (m, 9H); 3.28 (d, 1H, J=10.7 Hz); 7.14-7.37 (m, 5H).
$^{13}$C-NMR (DMSO-d$_6$): 24.4; 26.09; 29.5; 29.7; 34.5; 49.9 (2C); 72.7; 126.7; 127.6 (2C); 128.8 (2C); 136.4; 211.3. 2C signals are superimposed with the DMSO signal.

Synthesis of the amino-, aminomethyl- and aminoethyl-cyclohexyls

The corresponding amines were obtained from the cyclohexanone derivatives.

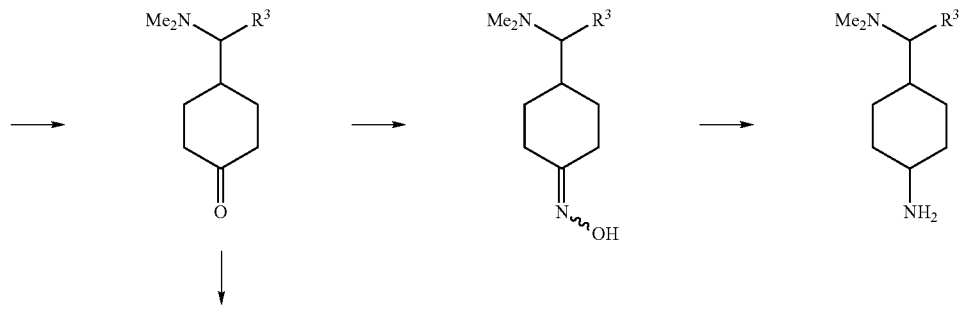

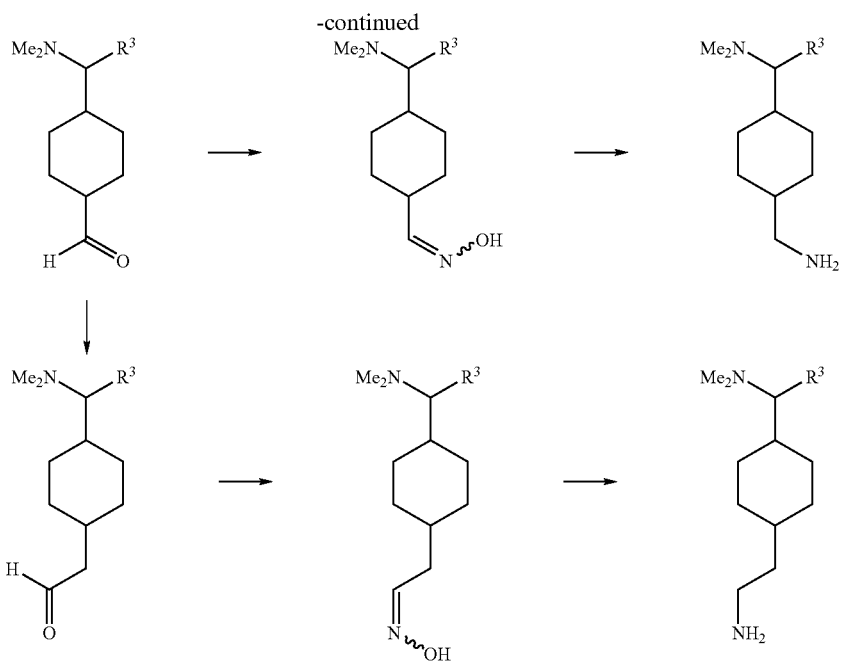

Synthesis of the aminocyclohexanes

The aminocyclohexanes were prepared by two-stage reactions from the appropriately substituted cyclohexanones with hydroxylamine hydrochloride and subsequent cleavage with lithium aluminium hydride.

Synthesis of 4-(dimethylamino-phenyl-methyl)-cyclohexylamine ($R^1$=Me, $R^2$=Me, $R^3$=phenyl) A1

4-(Dimethylamino-phenyl-methyl)-cyclohexanrone oxime ($R^1$=Me, $R^2$=Me, $R^3$=phenyl)

The ketone (9.25 g, 40 mmol) and hydroxylamine hydrochloride (4.17 g, 60 mmol) were dissolved in abs. ethanol (150 ml); basic ion exchanger Amberlyst A21 (28 g) was added thereto, and stirring was carried out overnight at RT. The ion exchanger was filtered off and washed with ethanol (2×50 ml). The solution was concentrated and the residue was adjusted to pH 11 with 5N NaOH. The aqueous phase was extracted with ethyl acetate (3×50 ml), and the organic phase was dried over sodium sulfate and concentrated in vacuo.

Yield: 9.54 g (97%); melting point: 110-115° C. (colourless crystals)

$^{13}$C-NMR (CDCl$_3$): 23.53; 23.70; 27.87; 29.04; 29.48; 30.70; 31.26; 31.40; 37.89 (C$_4$); 42.02 (N(CH$_3$)$_2$); 74.36 (CH); 126.87 (C$_{arom}$); 127.56 (C$_{arom}$); 129.09 (C$_{arom}$); 136.57 (C$_{arom}$); 160.12 (C=N—O).

4-(Dimethylamino-phenyl-methyl)-cyclohexylamine ($R^1$=Me, $R^2$=Me, $R^3$=phenyl) A1

LiAlH$_4$ (2.92 g, 77 mmol) was added, under argon, to absolute THF (400 ml), the mixture was heated to 60° C., and the oxime (9.5 g, 38.5 mmol), dissolved in THF (90 ml), was added dropwise. After 4 hours' stirring at 60° C., water (100 ml) was added dropwise, while cooling with an ice bath (10° C.), and the solution was filtered off over kieselguhr. The filter residue was washed with THF. The THF was removed in vacuo, and the residue was adjusted to pH 11 with 5N NaOH and extracted with ethyl acetate (4×40 ml). The organic phase was dried over sodium sulfate and concentrated by evaporation, and the residue was purified over a silica gel column (300 g) with acetonitrile/methanol/0.5 M NH$_4$Cl (9:1:1).

The individual fractions were dissolved in water and DCM and rendered alkaline with ammonia, and the aqueous phase was extracted (twice) with DCM.

Overall yield: 6.33 g (71%), oil $^{13}$C-NMR (CDCl$_3$): 24.22; 24.80; 28.24; 29.96; 32.39; 32.45; 36.03; 36.58; 36.79; 37.93 (C$_4$); 41.33; 41.89 (N(CH$_3$)$_2$); 47.42; 50.85; 71.95; 75.22 (CH); 126.52 (C$_{arom}$); 127.29 (C$_{arom}$); 127.33 (C$_{arom}$); 129.04 (C$_{arom}$); 129.11 (C$_{arom}$); 136.22 (C$_{arom}$); 137.03 (C$_{arom}$).

Synthesis of 4-[dimethylamino-(4-fluorophenyl)-methyl]-cyclohexylamine ($R^1$=Me, $R^2$=Me $R^3$=4-fluorophenyl) A2

4-[Dimethylamino-(4-fluorophenyl)-methyl]-cyclohexanone oxime ($R^1$=Me, $R^2$=Me, $R^3$=4-fluorophenyl)

The ketone (10.68 g, 43 mmol) and hydroxylamine hydrochloride (4.52 g, 65 mmol) were dissolved in abs. ethanol (160 ml); basic ion exchanger Amberlyst A21 (30 g) was added thereto, and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.

Yield: 10.49 g (93%)

$^{13}$C-NMR (CDCl$_3$): 23.76; 23.66; 27.69; 28.87; 29.50; 30.73; 31.22; 31.38; 38.06 (C$_4$); 42.01 (N(CH$_3$)$_2$); 73.66 (CH); 114.36 (C$_{arom}$); 114.57 (C$_{arom}$); 130.32 (C$_{arom}$); 130.40 (C$_{arom}$); 132.40 (C$_{arom}$); 160.03 (C=N—O); 160.49 (C$_{arom}$); 162.93 (C$_{arom}$).

4-[Dimethylamino-(4-fluorophenyl)-methyl]-cyclohexylamine ($R^1$=Me, $R^2$=Me, $R^3$=4-fluorophenyl) A2

LiAlH$_4$ (3.04 g, 82 mmol) was added, under argon, to absolute THF (435 ml), the mixture was heated to 60° C., and the oxime (10.49 g, 40 mmol), dissolved in THF (90 ml), was added dropwise. After 4 hours' stirring at 60° C., water (100 ml) was added dropwise, while cooling with an ice bath (10° C.), and the solution was filtered off over kieselguhr. The filter residue was washed with THF. The THF was removed in vacuo, and the residue was adjusted to pH 11 with 5N NaOH and extracted with ethyl acetate (4×50 ml). The organic phase was dried over sodium sulfate and concentrated by evaporation, and the residue was purified by flash chromatography with acetonitrile/methanol/0.5M NH$_4$Cl (9:1:1).

The individual fractions were dissolved in water and DCM and rendered alkaline with ammonia, and the aqueous phase was extracted twice with DCM.

Yield: 6.95 g (70%), oil $^{13}$C-NMR (CDCl$_3$): 24.01; 24.76; 27.99; 29.92; 32.32; 36.26; 36.51; 36.73; 38.07; 41.26 (C$_4$); 41.85 (N(CH$_3$)$_2$); 47.31; 50.81; 71.25; 74.44 (CH); 114.01 (C$_{arom}$); 114.08 (C$_{arom}$); 130.20 (C$_{arom}$); 130.27 (C$_{arom}$); 132.02 (C$_{arom}$); 132.85 (C$_{arom}$); 160.22 (C$_{arom}$); 162.64 (C$_{arom}$).

Synthesis of 4-[dimethylamino-(3-fluorophenyl)-methyl]-cyclohexylamine ($R^1$=Me, $R^2$=Me, $R^3$=3-fluorophenyl) A3

4-[Dimethylamino-(3-fluorophenyl)-methyl]-cyclohexanone oxime ($R^1$=Me, $R^2$=Me, $R^3$=3-fluorophenyl)

The ketone (10 g, 40 mmol) and hydroxylamine hydrochloride (4.17 g, 60 mmol) were dissolved in abs. ethanol (150 ml); basic ion exchanger Amberlyst A21 (28 g) was added thereto, and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.

Yield: 10.05 g (95%)

$^{13}$C-NMR (CDCl$_3$): 23.48; 23.66; 27.69; 28.87; 29.39; 30.61; 31.18; 31.33; 37.91 (C$_4$); 41.99 (N(CH$_3$)$_2$); 74.00 (CH); 113.70 (C$_{arom}$); 113.90 (C$_{arom}$); 115.51 (C$_{arom}$); 124.80 (C$_{arom}$); 128.90 (C$_{arom}$); 128.98 (C$_{arom}$); 139.48 (C$_{arom}$); 139.54 (C$_{arom}$); 159.89 (C=N—O); 161.13 (C$_{arom}$); 163.57 (C$_{arom}$).

4-[Dimethylamino-(3-fluorophenyl)-methyl]-cyclohexylamine ($R^1$=Me, $R^2$=Me, $R^3$=3-fluorophenyl) A3

LiAlH$_4$ (2.83 g, 75 mmol) was added, under argon, to absolute THF (400 ml), the mixture was heated to 60° C., and the oxime (9.86 g, 37.3 mmol), dissolved in THF (90 ml), was added dropwise. After 4 hours' stirring at 60° C., water (100 ml) was added dropwise, while cooling with an ice bath (10° C.), and the solution was filtered off over kieselguhr. The filter residue was washed with THF. The THF was removed in vacuo, and the residue was adjusted to pH 11 with 5N NaOH and extracted with ethyl acetate (4×40 ml). The organic phase was dried over sodium sulfate and concentrated by evaporation, and the residue was purified over a silica gel column (300 g) with acetonitrile/methanol/0.5M NH$_4$Cl (9:1:1).

The individual fractions were dissolved in water and DCM and rendered alkaline with ammonia, and the aqueous phase was extracted twice with DCM.

Yield: 6.81 g (73%), oil $^{13}$C-NMR (CDCl$_3$): 24.08; 24.69; 28.05; 29.84; 32.33; 32.37; 36.10; 36.48; 36.69; 37.95; 41.27 (C$_4$); 41.85 (N(CH$_3$)$_2$); 47.32; 50.81; 71.63; 74.81 (CH); 113.29 (C$_{arom}$); 115.43 (C$_{arom}$); 124.74 (C$_{arom}$); 128.58 (C$_{arom}$); 139.19 (C$_{arom}$); 139.99 (C$_{arom}$); 160.97 (C$_{arom}$); 163.41 (C$_{arom}$).

Synthesis of 4-(dimethylamino-thiophen-2-yl-methyl)-cyclohexylamine ($R^1$=Me, $R^2$=Me, $R^3$=2-thiophene) A4

4-(Dimethylamino-thiophen-2-yl-methyl)-cyclohexanone oxime ($R^1$=Me, $R^2$=Me, $R^3$=2-thiophene)

The ketone (9.49 g, 40 mmol) and hydroxylamine hydrochloride (4.17 g, 60 mmol) were dissolved in abs. ethanol (150 ml); basic ion exchanger Amberlyst A21 (28 g) was added thereto, and stirring was carried out overnight at RT. The ion exchanger was filtered off and washed with ethanol (2×50 ml). The solution was concentrated, the residue was adjusted to pH 11 with 5N NaOH. The aqueous phase was extracted with ethyl acetate (3×50 ml), and the organic phase was dried over sodium sulfate and concentrated in vacuo.

Yield: 9.21 g (91%)

Melting point: 118-121° C., yellow crystals

4-(Dimethylamino-thiophen-2-yl-methyl)-cyclohexylamine ($R^1$=Me, $R^2$=Me, $R^3$=2-thiophene) A4

LiAlH$_4$ (2.73 g, 72 mmol) was added, under argon, to absolute THF (300 ml), the mixture was heated to 60° C., and the oxime (9.08 g, 35.9 mmol), dissolved in THF (80 ml), was added dropwise. After 4 hours' stirring at 60° C., water (80 ml) was added dropwise, while cooling with an ice bath (10° C.), and the solution was filtered off over kieselguhr. The filter residue was washed with THF. The THF was removed in vacuo, and the residue was adjusted to pH 11 with 5N NaOH and extracted with ethyl acetate (3×50 ml). The organic phase was dried over sodium sulfate and concentrated by evaporation, and the residue was purified over a silica gel column (300 g) with acetonitrile/methanol/0.5M NH$_4$Cl (8:2:1).

The individual fractions were dissolved in water and DCM and rendered alkaline with ammonia, and the aqueous phase was extracted twice with DCM.

Overall yield: 5.66 g (66%), oil $^{13}$C-NMR (CDCl$_3$): 24.81; 24.96; 29.26; 29.76; 32.18; 32.22; 36.46; 36.58; 38.10; 39.99; 40.86; 41.20 (N(CH$_3$)$_2$); 47.66; 50.80; 64.27; 69.82; 123.43; 125.71; 125.75; 125.95; 126.07; 139.34; 139.79.

Synthesis of 4-(1-dimethylamino-3-phenyl-propyl)-cyclohexylamine ($R^1$=Me, $R^2$=Me, $R^3$=phenethyl) A5

4-(1-Dimethylamino-3-phenyl-propyl)-cyclohexanone oxime ($R^1$=Me, $R^2$=Me, $R^3$=phenethyl)

The ketone (10.2 g, 40 mmol) and hydroxylamine hydrochloride (4.17 g, 60 mmol) were dissolved in abs. ethanol (150 ml); basic ion exchanger Amberlyst A21 (28 g) was added thereto, and stirring was carried out overnight at RT. The ion exchanger was filtered off and washed with ethanol (2×50 ml), the solution was concentrated, and the residue was adjusted to pH 11 with 5N NaOH. The aqueous phase was extracted with ethyl acetate (3×50 ml), and the organic phase was dried over sodium sulfate and concentrated in vacuo.

Yield: 10.8 g (100%), oil $^{13}$C-NMR (CDCl$_3$): 23.80; 23.96; 28.80; 29.27; 30.00; 31.21; 31.49; 31.58; 35.89 (C$_4$); 39.29; 41.26 (N(CH$_3$)$_2$); 67.24 (CH); 125.58 (C$_{arom}$); 128.13 (C$_{arom}$); 142.40 (C$_{arom}$); 159.99; 160.04 (C=N—O).

4-(1-Dimethylamino-3-phenyl-propyl)-cyclohexylamine (R$^1$=Me, R$^2$=Me, R$^3$=phenethyl) A5

LiAlH$_4$ (3.04 g, 82 mmol) was added, under argon, to absolute THF (435 ml), the mixture was heated to 60° C., and the oxime (11.14 g, 40 mmol), dissolved in THF (90 ml), was added dropwise. After 4 hours' stirring at 60° C., water (100 ml) was added dropwise, while cooling with an ice bath (10° C.), and the solution was filtered off over kieselguhr. The filter residue was washed with THF. The THF was removed in vacuo, and the residue was adjusted to pH 11 with 5N NaOH and extracted with ethyl acetate (4×50 ml). The organic phase was dried over sodium sulfate and concentrated by evaporation, and the residue was purified over a silica gel column (300 g) with acetonitrile/methanol/0.5M NH$_4$Cl (9:1:1) and (9:4:1).

The individual fractions were dissolved in water and DCM and rendered alkaline with ammonia, and the aqueous phase was extracted twice with DCM.

Yield: 5.02 g (50%), oil $^{13}$C-NMR (CDCl$_3$): 24.70; 25.36; 29.22; 29.35; 30.42; 32.98; 35.46; 35.72; 36.95; 37.07; 38.89 (C$_4$); 39.32; 41.04; 41.26 (N(CH$_3$)$_2$); 46.98; 50.85; 66.01; 68.05 (CH); 125.49 (C$_{arom}$); 128.11 (C$_{arom}$); 128.14 (C$_{arom}$); 142.75 (C$_{arom}$).

Synthesis of 4-(1-morpholin-4-yl-3-phenyl-propyl)-cyclohexylamine (NR$^1$R$^2$=morpholine, R$^3$=phenethyl) A6

4-(1-Morpholino-3-phenylpropyl)cyclohexanone oxime (NR$^1$R$^2$=morpholine, R$^3$=phenethyl)

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

4-(1-Morpholin-4-yl-3-phenyl-propyl)-cyclohexylamine (NR$^1$R$^2$=morpholine, R$^3$ phenethyl) A6

The oxime (38.5 mmol) in THF (90 ml) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

Synthesis of 4-(3-phenyl-1-piperidin-1-yl-propyl)-cyclohexylamine (NR$^1$R$^2$=piperidine, R$^3$=phenethyl) A7

4-(3-Phenyl-1-(piperidin-1-yl)propyl)cyclohexanone oxime (NR$^1$R$^2$=piperidine, R$^3$=phenethyl)

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

4-(3-Phenyl-1-piperidin-1-yl-propyl)-cyclohexylamine (NR$^1$R$^2$=piperidine, R$^3$=phenethyl) A7

The oxime (38.5 mmol) in THF (90 ml) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

Synthesis of 4-(phenylpyrrolidin-1-yl-methyl)cyclohexylamine (NR$^1$R$^2$=pyrrolidine, R$^3$=phenyl) A9

4-(Phenylpyrrolidin-1-yl-methyl)cyclohexanone oxime (NR$^1$R$^2$=pyrrolidine, R$^3$=phenyl)

Basic ion exchanger Amberlyst A21 (4 g) was added to a solution of 4-(phenyl-pyrrolidin-1-yl-methyl)cyclohexanone (1.55 g, 5.7 mmol) and hydroxylamine hydrochloride (594 mg, 8.55 mmol) in anhydrous ethanol (30 ml), and stirring was carried out for 3 d at room temperature. The ion exchanger was filtered off and washed with ethanol (2×5 ml). The filtrate was concentrated in vacuo, water (5 ml) was added to the residue, the pH was adjusted to 11 with 5 N sodium hydroxide solution, and extraction with ethyl acetate (3×15 ml) was carried out. The combined organic phases were dried over sodium sulfate and concentrated in vacuo.

Yield: 1.45 g (93%), white solid; melting point: 49-54° C.

$^1$H-NMR (DMSO-d$_6$): 0.50-0.90 (m, 2H); 1.54-2.48 (m, 14H); 3.02-3.18 (m, 1H); 7.10-7.37 (m, 5H); 10.07 (s, 1H).

4-(Phenylpyrrolidin-1-yl-methyl)cyclohexylamine (NR$^1$R$^2$=pyrrolidine, R$^3$=phenyl) A9

A solution of (phenylpyrrolidin-1-yl-methyl)cyclohexanone oxime (1.43 g, 5.25 mmol) in absolute tetrahydrofuran (14 ml) was added dropwise at 60° C., under argon, to a suspension of lithium aluminium hydride (398 mg, 10.5 mmol) in absolute tetrahydrofuran (50 ml), and stirring was carried out for 4.5 h at that temperature. After cooling, water (2 ml) and 4 N sodium hydroxide solution (500 µl) were added dropwise. The suspension was filtered, and the filtrate was dried over sodium sulfate and concentrated in vacuo.

Yield: 1.19 g (88%), yellow oil $^1$H-NMR (DMSO-d$_6$): 0.40-3.25 (m, 21H); 7.10-7.30 (m, 5H).

$^{13}$C-NMR (DMSO-d$_6$): 21.7; 22.6; 22.7; 24.4; 25.7; 29.6; 32.3; 32.5; 36.2; 36.4; 45.9; 49.9; 50.7; 50.8; 126.4; 126.5; 127.3; 127.4; 128.9; 129.0; 138.7; 139.4.

The product is a cis/trans isomer mixture.

Synthesis of 4-(phenylpiperidin-1-yl-methyl)cyclohexylamine (NR$^1$R$^2$=piperidine, R$^3$=phenyl) A10

4-(Phenylpiperidin-1-yl-methyl)cyclohexanone oxime (NR$^1$R$^2$=piperidine, R$^3$=phenyl)

Basic ion exchanger Amberlyst A21 (4.80 g) was added to a solution of 4-(phenyl-piperidin-1-yl-methyl)cyclohexanone (1.85 g, 6.8 mmol) and hydroxylamine hydrochloride (709 mg, 10.2 mmol) in anhydrous ethanol (40 ml), and stirring was carried out for 3 d at room temperature. The ion exchanger was filtered off and washed with ethanol (2×10 ml). The filtrate was concentrated in vacuo, water (15 ml) was added to the residue, the pH was adjusted to 11 with 5 N sodium hydroxide solution, and extraction with ethyl acetate (3×25 ml) was carried out. The combined organic phases were dried over sodium sulfate and concentrated in vacuo.

Yield: 1.70 g (87%), white solid; melting point: 131-137° C.

$^1$H-NMR (DMSO-$d_6$): 0.70-2.40 (m, 18H); 2.82-3.17 (m, 1H); 3.18 (d, 1H, J=9.8 Hz); 7.10-7.37 (m, 5H); 10.08 and 10.11 (2 s, 1H).

The product is an E/Z isomer mixture.

4-(Phenylpiperidin-1-yl-methyl)cyclohexylamine (NR$^1$R$^2$=piperidine, R$^3$=phenyl) A10

A solution of 4-(phenylpiperidin-1-yl-methyl)cyclohexanone oxime (1.60 g, 5.6 mmol) in absolute tetrahydrofuran (20 ml) was added dropwise at 60° C., under argon, to a suspension of lithium aluminium hydride (425 mg, 11.2 mmol) in absolute tetrahydrofuran (50 ml), and stirring was carried out for 4 h at that temperature. After cooling, water (2 ml) and 4 N sodium hydroxide solution (0.5 ml) were added dropwise. The suspension was filtered, and the filtrate was dried over sodium sulfate and concentrated in vacuo.

Yield: 1.50 g (98%), yellowish oil $^1$H-NMR (DMSO-$d_6$): 0.60-2.23 (m, 20H); 2.23-2.42 (m, 0.5H); 2.73-2.84 (m, 0.5H); 3.05 (d, 0.5H, J=10.7 Hz); 3.35 (d, 0.5H, J=10.7 Hz); 3.56-3.63 (m, 1H) 7.00-7.40 (m, 5H).

The product is a cis/trans isomer mixture.

Synthesis of 4-(morpholin-4-yl-phenylmethyl)cyclohexylamine (NR$^1$R$^2$=morpholine, R$^3$=phenyl) A11

4-(Morpholin-4-yl-phenylmethyl)cyclohexanone oxime (NR$^1$R$^2$=morpholine, R$^3$=phenyl)

Basic ion exchanger Amberlyst A21 (3.1 g) was added to a solution of 4-(morpholin-4-yl-phenylmethyl)cyclohexanone (1.20 g, 4.4 mmol) and hydroxylamine hydrochloride (459 mg, 6.6 mmol) in anhydrous ethanol (30 ml), and stirring was carried out for 20 h at room temperature. The ion exchanger was filtered off and washed with ethanol. The filtrate was concentrated in vacuo, water (10 ml) was added to the residue, the pH was adjusted to 11 with 5 N sodium hydroxide solution, and extraction with ethyl acetate (3×20 ml) was carried out. The combined organic phases were dried over sodium sulfate and concentrated in vacuo.

Yield: 1.20 g (95%), white solid
Melting point: 82-87° C.

$^1$H-NMR (DMSO-$d_6$): 0.66-2.50 (m, 12H); 2.90-3.14 (m, 1H); 3.18-3.48 (m, 1H); 3.48-3.66 (m, 4H); 7.15-7.38 (m, 5H); 10.09 and 10.11 (2 s, 1H).

The product is an E/Z isomer mixture.

4-(Morpholin-4-yl-phenylmethyl)cyclohexylamine (NR$^1$R$^2$=morpholine, R$^3$ phenyl) A11

A solution of 4-(morpholin-4-yl-phenylmethyl)cyclohexanone oxime (1.20 g, 4.16 mmol) in absolute tetrahydrofuran (12 ml) was added dropwise at 60° C., under argon, to a suspension of lithium aluminium hydride (316 mg, 8.32 mmol) in absolute tetrahydrofuran (40 ml), and stirring was carried out for 4 h at that temperature. After cooling, water (1.5 ml) and 4 N sodium hydroxide solution (0.4 ml) were added dropwise. The suspension was filtered, and the filtrate was dried over sodium sulfate and concentrated in vacuo.

Yield: 1.12 g (98%), yellowish oil $^1$H-NMR (DMSO-$d_6$): 0.60-3.65 (m, 21H); 7.10-7.40 (m, 5H).

The product is a cis/trans isomer mixture.

The 4-methylpiperazine derivative was prepared via the benzotriazole aminal by the following synthesis route:

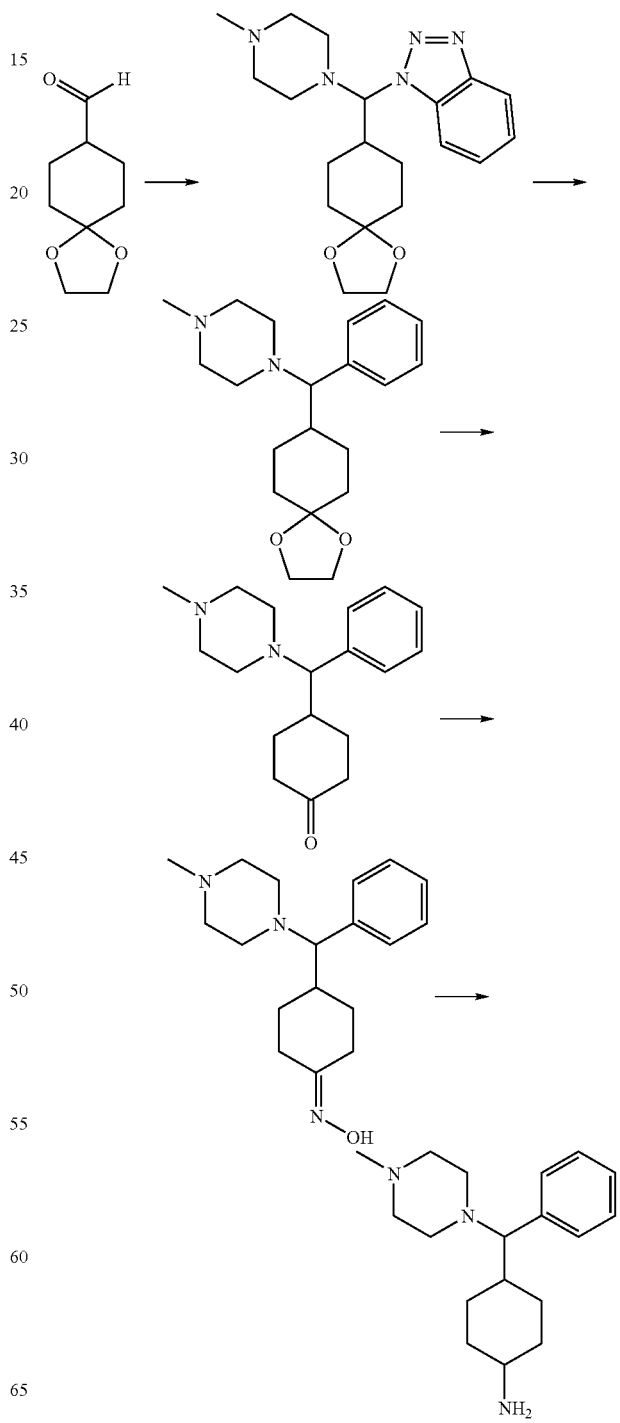

11-(1-(1,4-Dioxa-spiro[4.5]dec-8-yl)(4-methylpiper-azin-1-yl)methyl)-1H-benzo[d][1,2,3]triazole The aldehyde (23.4 mmol), N-methylpiperazine (23.4 mmol) and 1H-benzotriazole (23.4 mmol) were heated for 16 h under reflux in benzene (60 ml), and the resulting water of reaction was removed by means of a water separator. The benzene was removed in vacuo, and the residue was used directly in the next stage.

4-Methyl-[1-(1,4-dioxa-spiro[4.5]dec-8-yl)-3-phenyl-propyl]-piperazine

A solution of the benzotriazole adduct (23.5 mmol) in THF was added dropwise to a solution of phenylmagnesium chloride (47.1 mmol) in THF, and stirring was carried out for 16 h at 25° C. The reaction solution was cooled to 0° C., saturated aqueous $NH_4Cl$ solution was added, and extraction with ethyl acetate (2×300 ml) was then carried out. The organic phase was washed with water and saturated aqueous NaCl solution. After drying the organic phase over $Na_2SO_4$ and filtration, the solvent was removed in vacuo. The product was purified by column chromatography (2-5% methanol/dichloromethane).

4-((4-Methylpiperazin-1-yl)(phenyl)methyl)cyclohexanone

Conc. HCl and water (1:1, 88 ml) were added slowly at 0° C. to the Grignard adduct (105 mmol), and stirring was carried out for 20 h at 25° C. The reaction solution was then extracted with ethyl acetate (2×100 ml). After addition of 5N sodium hydroxide solution to establish a basic pH value, extraction with dichloromethane (3×100 ml) was carried out. The combined organic phases were dried over $Na_2SO_4$ and filtered off. The solvent was removed in vacuo, and the product was used in the next stage without being purified further.

4-((4-Methylpiperazin-1-yl)(phenyl)methyl)cyclohexanone oxime

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

4-[(4-Methyl-piperazin-1-yl)-phenyl-methyl]-cyclohexylamine A8

The oxime (38.5 mmol) in THF (90 ml) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

Synthesis of the aminomethylcyclohexanes

The aminomethylcyclohexanes were prepared from the appropriately substituted cyclohexanones by three-stage reactions via the cyclohexylaldehyde stage by reaction with hydroxylamine hydrochloride and subsequent cleavage with lithium aluminium hydride.

4-(Dimethylamino-phenyl-methyl)-cyclohexane-carbaldehyde ($R^1$=Me, $R^2$=Me, $R^3$=phenyl)

(Methoxymethyl)triphenylphosphonium chloride (31.5 g, 0.092 mol) was suspended in abs. THF (150 ml) under argon; potassium tert-butoxide (10.38 g, 0.092 mol), dissolved in abs. THF (100 ml), was added dropwise at 0° C., and stirring was then carried out for 15 min at 0° C.

The ketone (14.2 g, 0.061 mol), dissolved in abs. THF (100 ml), was then added dropwise at RT to the above solution, and stirring was carried out overnight at RT. Hydrolysis was carried out dropwise with water (50 ml) and 6N HCl (150 ml), while cooling with ice-water. After one hour's stirring at RT, extraction with diethyl ether (10×50 ml) was carried out, and the aqueous phase was adjusted to pH 11 with 5N NaOH, extracted by shaking with ethyl acetate (3×50 ml), dried over sodium sulfate and concentrated in vacuo. The crude product was purified over a silica gel column (300 g) with ethyl acetate/cyclohexane (1:1).

Yield: 12.2 g (82%)

$^{13}$C-NMR ($CDCl_3$): 24.01; 24.22; 25.90; 26.06; 26.40; 27.33; 28.21; 29.92; 37.00; 38.19 ($C_4$); 41.51; 41.98; ($N(CH_3)_2$); 47.45; 50.60; 73.37; 75.24 (CH); 126.72 ($C_{arom}$); 126.76 ($C_{arom}$); 127.48 ($C_{arom}$); 129.13 ($C_{arom}$); 136.14 ($C_{arom}$); 136.79 ($C_{arom}$); 204.22; 205.05 (CHO).

4-(Dimethylamino-phenyl-methyl)-cyclohexane-carbaldehyde oxime ($R^1$=Me, $R^2$=Me, $R^3$=phenyl)

The carbaldehyde (7.36 g, 30 mmol) and hydroxylamine hydrochloride (3.12 g, 45 mmol) were dissolved in abs. ethanol (100 ml); basic ion exchanger Amberlyst A21 (21 g) was added thereto, and stirring was carried out overnight at RT. The ion exchanger was filtered off and washed with ethanol (2×50 ml). The solution was concentrated, and the residue was adjusted to pH 11 with 5N NaOH. The aqueous phase was extracted with ethyl acetate (3×50 ml), and the organic phase was dried over sodium sulfate and concentrated in vacuo.

Yield: 7.81 g (100%)

$^{13}$C-NMR ($CDCl_3$): 25.83; 26.34; 27.10; 27.55; 28.25; 29.41; 30.12; 30.32; 34.20; 36.45; 36.74; 37.00; 38.19 ($C_4$); 41.37; 41.03; ($N(CH_3)_2$); 72.28; 75.59 (CH); 126.77 ($C_{arom}$); 127.50 ($C_{arom}$); 129.22 ($C_{arom}$); 136.14 ($C_{arom}$); 136.94 ($C_{arom}$); 137.05 ($C_{arom}$); 154.84; 155.55; 156.35.

[(4-Aminomethyl-cyclohexyl)-phenyl-methyl]-dimethylamine ($R^1$=Me, $R^2$=Me, $R^3$=phenyl) A12

$LiAlH_4$ (2.27 g, 60 mmol) was added, under argon, to absolute THF (300 ml); the mixture was heated to 60° C., and the oxime (7.81 g, 30 mmol), dissolved in THF (60 ml), was added dropwise. After 4 hours' stirring at 60° C., water (70 ml) was added dropwise, while cooling with an ice bath (10° C.), and the reaction solution was filtered off over kieselguhr. The filter residue was washed with THF. The combined organic phases were concentrated in vacuo, and the residue was adjusted to pH 11 with 5N NaOH and extracted with ethyl acetate (4×40 ml). The organic phase was dried over sodium sulfate and concentrated.

Yield: 6.4 g (87%), oil $^{13}$C-NMR ($CDCl_3$): 25.53; 26.03; 26.64; 26.68; 29.06; 30.37; 30.51; 30.67; 30.74; 36.01; 38.83; 38.93; ($C_4$); 41.50; 41.94; ($N(CH_3)_2$); 72.28; 75.59 (CH); 126.77 ($C_{arom}$); 127.50 ($C_{arom}$); 129.22 ($C_{arom}$); 136.14 ($C_{arom}$); 136.94 ($C_{arom}$); 137.05 ($C_{arom}$); 154.84; 155.55; 156.35.

4-[Dimethylamino-(4-fluorophenyl)-methyl]-cyclohexane-carbaldehyde ($R^1$=Me, $R^2$=Me, $R^3$=4-fluorophenyl)

(Methoxymethyl)triphenylphosphonium chloride (25.7 g, 75 mmol) was suspended in abs. THF (100 ml) under argon; potassium tert-butoxide (8.42 g, 75 mmol), dissolved in abs. THF (70 ml), was added dropwise at 0° C., and stirring was then carried out for 15 min at 0° C.

The ketone (12.44 g, 50 mmol), dissolved in abs. THF (75 ml), was then added dropwise at RT to the above solution, and stirring was carried out overnight at RT. Hydrolysis was carried out dropwise with water (38 ml) and 6N HCl (112 ml), while cooling with ice-water. After one hour's stirring at RT, extraction with diethyl ether (10×50 ml) was carried out, and the aqueous phase was adjusted to pH 11 with 5N NaOH, extracted by shaking with ethyl acetate (3×50 ml), dried over sodium sulfate and concentrated in vacuo. The crude product was purified by flash chromatography with ethyl acetate/cyclohexane (1:1).

Yield: 9.13 g (70%).

$^1$H-NMR (DMSO, 600 MHz, selected signals): δ=1.97 (s, 3H, minor diastereoisomer); 1.99 (s, 3H, major diastereoisomer); 3.08 (d, 1H, J=9.06 Hz, major diastereoisomer); 3.14 (d, 1H, J=9.82 Hz, minor diastereoisomer); 9.53 (s, 1H, major diastereoisomer); 9.56 (s, 1H, minor diastereoisomer).

$^{13}$C-NMR (CDCl$_3$, both diastereoisomers): δ=23.97; 24.21; 25.85; 26.02; 26.17; 27.35; 28.00; 29.90; 37.26; 38.34; 41.50; 41.95; 47.36; 50.55; 72.75; 75.84; 114.25; 114.45; 130.33; 130.40; 132.61; 160.41; 162.83; 204.10; 204.93.

4-[Dimethylamino-(4-fluorophenyl)-methyl]-cyclohexanecarbaldehyde oxime ($R^1$=Me, $R^2$=Me, $R^3$=4-fluorophenyl)

The aldehyde (6.50 g, 25 mmol) and hydroxylamine hydrochloride (2.6 g, 37.5 mmol) were dissolved in abs. ethanol (80 ml); basic ion exchanger Amberlyst A21 (16.5 g) was added thereto, and stirring was carried out overnight at RT. The ion exchanger was filtered off and washed with ethanol (2×50 ml). The solution was concentrated, and the residue was adjusted to pH 11 with 5N NaOH. The aqueous phase was extracted with ethyl acetate (3×50 ml), and the organic phase was dried over sodium sulfate and concentrated in vacuo.

Yield: 6.9 g (99%)

[(4-Aminomethyl-cyclohexyl)-(4-fluorophenyl)-methyl]-dimethylamine ($R^1$=Me, $R^2$=Me, $R^3$=4-fluorophenyl) A13

LiAlH$_4$ (1.9 g, 50 mmol) was added, under argon, to absolute THF (360 ml); the mixture was heated to 60° C., and the oxime (6.9 g, 25 mmol), dissolved in THF (60 ml), was added dropwise. After 4 hours' stirring at 60° C., water (93 ml) was added dropwise, while cooling with an ice bath (10° C.), and the reaction solution was filtered off over kieselguhr. The filter residue was washed with THF. The combined organic phases were concentrated in vacuo, and the residue was adjusted to pH 11 with 5N NaOH and extracted three times with ethyl acetate (100 ml each time). The organic phase was dried over sodium sulfate and concentrated.

Yield: 5.4 g (82%), oil $^{13}$C-NMR (CDCl$_3$): 25.25; 25.93; 26.60; 28.75; 30.30; 30.40; 30.67; 36.20; 38.78; 38.93; (C$_4$); 41.24; 41.43 (N(CH$_3$)$_2$); 48.71; 70.62; 74.69 (CH); 113.97 (C$_{arom}$); 114.04 (C$_{arom}$); 130.24 (C$_{arom}$); 130.31 (C$_{arom}$); 132.94 (C$_{arom}$); 160.19; 162.62; (C$_{arom}$).

4-[Dimethylamino-(3-fluorophenyl)-methyl]-cyclohexane-carbaldehyde ($R^1$=Me, $R^2$=Me, $R^3$=3-fluorophenyl)

(Methoxymethyl)triphenylphosphonium chloride (15.42 g, 45 mmol) was suspended in abs. THF (50 ml) under argon; potassium tert-butoxide (5.05 g, 45 mmol), dissolved in abs. THF (50 ml), was added dropwise at 0° C., and stirring was then carried out for 15 min at 0° C.

The ketone (7.48 g, 0.30 mmol), dissolved in abs. THF (50 ml), was then added dropwise at RT to the above solution, and stirring was carried out overnight at RT. Hydrolysis was carried out dropwise with water (25 ml) and 6N HCl (75 ml), while cooling with ice-water. After one hour's stirring at RT, extraction with diethyl ether (10×50 ml) was carried out, and the aqueous phase was adjusted to pH 11 with 5N NaOH, extracted with ethyl acetate (3×50 ml), dried over sodium sulfate and concentrated in vacuo. The crude product was purified by flash chromatography with ethyl acetate/cyclohexane (1:1). Yield: 6.55 g (83%); melting point: 40-43° C.

$^1$H-NMR (DMSO, 600 MHz, selected signals): δ=1.99 (s, 3H); 2.01 (s, 3H); 3.10 (d, 1H, J=9.06 Hz); 3.18 (d, 1H, J=9.82 Hz); 9.54 (s, 1H); 9.56 (s, 1H).

$^{13}$C-NMR (CDCl$_3$): 23.93; 24.12; 25.79; 25.95; 26.19; 27.19; 27.99; 29.77; 37.05; 38.16; 41.45; 41.91; 47.30; 50.49; 71.50; 74.78; 113.50; 115.37; 124.78; 128.24; 130.59; 131.24; 131.67; 139.14; 139.76; 160.06; 163.50; 204.01; 204.85.

4-[Dimethylamino-(3-fluorophenyl)-methyl]-cyclohexane-carbaldehyde oxime ($R^1$=Me, $R^2$=Me, $R^3$=3-fluorophenyl)

The carbaldehyde (6.32 g, 24 mmol) and hydroxylamine hydrochloride (2.5 g, 36 mmol) were dissolved in abs. ethanol (90 ml); basic ion exchanger Amberlyst A21 (17 g) was added thereto, and stirring was carried out for 3.5 h at RT. The ion exchanger was filtered off and washed with ethanol (2×50 ml). The solution was concentrated, and the residue was adjusted to pH 11 with 5N NaOH. The aqueous phase was extracted with ethyl acetate (3×50 ml), and the organic phase was dried over sodium sulfate and concentrated in vacuo.

Yield: 6.68 g (100%)

$^{13}$C-NMR (CDCl$_3$): 25.59; 26.21; 27.38; 28.02; 28.36; 29.27; 29.45; 30.00; 34.14; 35.58; 36.56; 38.19 (C$_4$); 41.33; 41.99; (N(CH$_3$)$_2$); 72.02; 75.05; 75.19 (CH); 113.55 (C$_{arom}$); 115.62 (C$_{arom}$); 124.88 (C$_{arom}$); 128.78 (C$_{arom}$); 128.86 (C$_{arom}$); 139.84 (C$_{arom}$); 139.90 (C$_{arom}$); 154.38; 155.13; 161.10 (C$_{arom}$); 163.54 (C$_{arom}$).

[(4-Aminomethyl-cyclohexyl)-(3-fluorophenyl)-methyl]-dimethylamine ($R^1$=Me, $R^2$=Me, $R^3$=3-fluorophenyl) A14

LiAlH$_4$ (1.82 g, 48 mmol) was added, under argon, to absolute THF (300 ml); the mixture was heated to 60° C., and the oxime (6.68 g, 24 mmol), dissolved in THF (60 ml), was added dropwise. After 4 hours' stirring at 60° C., water (70 ml) was added dropwise, while cooling with an ice bath (10° C.), and the reaction solution was filtered over kieselguhr. The filter residue was washed with THF, the organic phases were combined, the THF was removed in vacuo, and the residue was adjusted to pH 11 with 5N NaOH and extracted with ethyl acetate (4×40 ml). The organic phase was dried over sodium sulfate and concentrated.

Yield: 5.7 g (90%), oil $^{13}$C-NMR (CDCl$_3$): 25.38; 25.93; 26.44; 28.89; 30.36; 30.45; 30.65; 36.10; 38.87; (C$_4$); 41.33; 41.49; 41.93 (N(CH$_3$)$_2$); 71.05; 75.11 (CH); 113.94 (C$_{arom}$); 115.53 (C$_{arom}$); 124.86 (C$_{arom}$); 128.59 (C$_{arom}$); 128.67 (C$_{arom}$); 140.14 (C$_{arom}$); 141.21 (C$_{arom}$); 161.03 (C$_{arom}$); 163.46 (C$_{arom}$).

4-[(4-Chloro-phenyl)-dimethylamino-methyl]-cyclohexanecarbaldehyde (R$^1$=Me, R$^2$=Me, R$^3$=4-chlorophenyl)

(Methoxymethyl)triphenylphosphonium chloride (68.55 g, 200 mmol) was suspended in abs. THF (200 ml) under argon; potassium tert-butoxide (22.44 g, 200 mmol), dissolved in abs. THF (300 ml), was added dropwise at 0° C., and stirring was then carried out for 15 min at 0° C.

The ketone (38 g, 143 mmol), dissolved in abs. THF (200 ml), was then added dropwise at RT to the above solution, and stirring was carried out overnight at RT. Hydrolysis was carried out dropwise with water (150 ml) and 6N HCl (450 ml), while cooling with ice-water. After one hour's stirring at RT, extraction with diethyl ether (10×100 ml) was carried out, and the aqueous phase was adjusted to pH 11 with 5N NaOH, extracted by shaking with ethyl acetate (3×100 ml), dried over sodium sulfate and concentrated in vacuo. The crude product was purified over two silica gel columns (400 g) with ethyl acetate/cyclohexane (1:1).

Yield: 32.17 g (80%).

$^1$H-NMR (DMSO, 600 MHz, selected signals): δ=1.97 (s, 3H); 1.99 (s, 3H); 3.07 (d, 1H, J=9.07 Hz); 3.14 (d, 1H, J=9.82 Hz); 9.53 (s, 1H, 9.55 (s, 1H). $^{13}$C-NMR (CDCl$_3$): δ=23.92; 24.16; 25.80; 25.97; 26.13; 27.25; 27.90; 29.81; 37.08; 38.19; 41.47; 41.96; 47.29; 50.48; 72.81; 74.54; 127.65; 130.28; 132.40; 134.78; 135.43; 203.98; 204.82.

4-[(4-Chlorophenyl)-dimethylamino-methyl]-cyclohexanecarbaldehyde oxime (R$^1$=Me, R$^2$=Me, R$^3$=4-chlorophenyl)

The carbaldehyde (7.55 g, 27 mmol) and hydroxylamine hydrochloride (2.81 g, 40 mmol) were dissolved in abs. ethanol (100 ml); basic ion exchanger Amberlyst A21 (19 g) was added thereto, and stirring was carried out for 3.5 h at RT. The ion exchanger was filtered off and washed with ethanol (2×50 ml). The solution was concentrated, and the residue was adjusted to pH 11 with 5N NaOH. The aqueous phase was extracted with ethyl acetate (3×50 ml), and the organic phase was dried over sodium sulfate and concentrated in vacuo.

Yield: 7.57 g (96%)

[(4-Aminomethyl-cyclohexyl)-(4-chlorophenyl)-methyl]-dimethylamine (R$^1$=Me, R$^2$=Me, R$^3$=4-chlorophenyl) A15

LiAlH$_4$ (1.89 g, 50 mmol) was added, under argon, to absolute THF (300 ml); the mixture was heated to 60° C., and the oxime (7.5 g, 25 mmol), dissolved in THF (60 ml), was added dropwise. After 4 hours' stirring at 60° C., water (70 ml) was added dropwise, while cooling with an ice bath (10° C.), and the reaction solution was filtered over kieselguhr. The filter residue was washed with THF, the organic phases were combined, the THF was removed in vacuo, and the residue was adjusted to pH 11 with 5N NaOH and extracted with ethyl acetate (4×40 ml). The organic phase was dried over sodium sulfate and concentrated.

Yield: 6.3 g (90%), oil $^{13}$C-NMR (CDCl$_3$): 25.22; 25.87; 26.58; 28.70; 30.36; 30.53; 30.59; 36.02; 38.76 (C$_4$); 41.29; 41.39; 41.91 (N(CH$_3$)$_2$); 45.64; 48.72; 70.72; 74.77 (CH); 127.46 (C$_{arom}$); 127.52 (C$_{arom}$); 130.27 (C$_{arom}$); 132.11 (C$_{arom}$); 132.15 (C$_{arom}$); 134.80 (C$_{arom}$); 135.72 (C$_{arom}$).

4-(Dimethylamino-thiophen-2-yl-methyl)-cyclohexanecarbaldehyde (R$^1$=Me, R$^2$=Me, R$^3$=2-thienyl)

(Methoxymethyl)triphenylphosphonium chloride (20.56 g, 60 mmol) was suspended in abs. THF (70 ml) under argon; potassium tert-butoxide (6.73 g, 60 mmol), dissolved in abs. THF (70 ml), was added dropwise at 0° C., and stirring was then carried out for 15 min at 0° C. The ketone (9.4 g, 40 mmol), dissolved in abs. THF (70 ml), was then added dropwise at RT to the above solution, and stirring was carried out overnight at RT. Hydrolysis was carried out dropwise with water (60 ml) and 6N HCl (180 ml), while cooling with ice-water. After one hour's stirring at RT, extraction with diethyl ether (5×50 ml) was carried out, and the aqueous phase was adjusted to pH 11 with 5N NaOH, extracted by shaking with ethyl acetate (3×50 ml), dried over sodium sulfate and concentrated in vacuo. The crude product was purified by flash chromatography with ethyl acetate/cyclohexane (1:1).

Yield: 7.66 g (77%).

$^1$H-NMR (DMSO, 600 MHz, selected signals): δ=2.03 (s, 3H); 2.05 (s, 3H); 3.44 (d, 1H, J=9.82 Hz); 3.52 (d, 1H, J=10.58 Hz); 9.54 (s, 1H); 9.58 (s, 1H).

$^{13}$C-NMR (CDCl$_3$): δ=23.74; 23.83; 25.80; 25.84; 26.98; 27.09; 29.15; 29.68; 39.13; 40.20; 40.98; 41.29 (N(CH$_3$)$_2$); 47.48; 50.49; 67.81; 69.79; 123.61; 123.70; 125.89; 126.20; 126.24; 139.14; 139.48; 204.07; 204.82.

4-(Dimethylamino-thiophen-2-yl-methyl)-cyclohexanecarbaldehyde oxime (R$^1$=Me, R$^2$=Me, R$^3$=2-thiophene)

The carbaldehyde (7.54 g, 30 mmol) and hydroxylamine hydrochloride (3.12 g, 45 mmol) were dissolved in abs. ethanol (100 ml); basic ion exchanger Amberlyst A21 (21 g) was added thereto, and stirring was carried out overnight at RT. The ion exchanger was filtered out and washed with ethanol (2×50 ml). The solution was concentrated, and the residue was adjusted to pH 11 with 5N NaOH. The aqueous phase was extracted with ethyl acetate (3×50 ml), and the organic phase was dried over sodium sulfate and concentrated in vacuo.

Yield: 7.99 g (100%)

[(4-Aminomethyl-cyclohexyl)-thiophen-2-yl-methyl]-dimethylamine (R$^1$=Me, R$^2$=Me, R$^3$=2-thiophene) A16

LiAlH$_4$ (2.27 g, 60 mmol) was added, under argon, to absolute THF (300 ml); the mixture was heated to 60° C., and the oxime (7.99 g, 30 mmol), dissolved in THF (60 ml), was added dropwise. After 4 hours' stirring at 60° C., water (70 ml) was added dropwise, while cooling with an ice bath (10° C.), and the reaction solution was filtered over kieselguhr. The filter residue was washed with THF, the organic phases were combined, the THF was removed in vacuo, and the residue was adjusted to pH 11 with 5N NaOH and extracted with ethyl acetate (3×50 ml). The organic phase was dried over sodium sulfate and concentrated.

Yield: 6.72 g (89%), oil $^{13}$C-NMR (CDCl$_3$): 25.93; 26.11; 26.24; 26.30; 29.97; 30.34; 30.42; 38.03; 40.65; 40.82; 41.18; 41.34 (N(CH$_3$)$_2$); 46.19; 48.67; 65.58; 70.06; 123.61; 125.88; 126.23; 140.08.

4-(1-Dimethylamino-3-phenyl-propyl)-cyclohexane-carbaldehyde (R$^1$=Me, R$^2$=Me, R$^3$=phenethyl)

(Methoxymethyl)triphenylphosphonium chloride (20.56 g, 60 mmol) was suspended in abs. THF (85 ml) under argon; potassium tert-butoxide (6.73 g, 60 mmol), dissolved in abs. THF (70 ml), was added dropwise at 0° C., and stirring was then carried out for 15 min at 0° C.

The ketone (10.2 g, 40 mmol), dissolved in abs. THF (60 ml), was then added dropwise at RT to the above solution, and stirring was carried out overnight at RT. Hydrolysis was carried out dropwise with water (35 ml) and 6N HCl (90 ml), while cooling with ice-water. After one hour's stirring at RT, extraction with diethyl ether (10×50 ml) was carried out, and the aqueous phase was adjusted to pH 11 with 5N NaOH, extracted with ethyl acetate (3×50 ml), dried over sodium sulfate and concentrated in vacuo. The crude product was purified by flash chromatography with ethyl acetate/cyclohexane (1:1).

Yield: 6.73 g (63%).

$^1$H-NMR (DMSO, 600 MHz, selected signals): δ=2.18 (s, 3H); 2.20 (s, 3H); 9.54 (s, 1H); 9.61 (s, 1H).

$^{13}$C-NMR (CDCl$_3$): δ=24.35; 24.49; 26.00; 26.09; 26.85; 27.79; 29.07; 29.13; 35.27; 39.02; 40.98; 41.19; 46.99; 50.33; 66.85; 67.85; 70.54; 71.42; 125.40; 125.44; 128.02; 128.13; 131.15; 131.17; 142.45; 204.10; 205.01.

4-(1-Dimethylamino-3-phenyl-propyl)-cyclohexanecarbaldehyde oxime (R$^1$=Me, R$^2$=Me, R$^3$=phenethyl)

The aldehyde (6.55 g, 24 mmol) and hydroxylamine hydrochloride (2.5 g, 36 mmol) were dissolved in abs. ethanol (90 ml); basic ion exchanger Amberlyst A21 (15.6 g) was added thereto, and stirring was carried out overnight at RT. The ion exchanger was filtered off and washed twice with ethanol (50 ml each time). The solution was concentrated, and residue was adjusted to pH 11 with 5N NaOH. The aqueous phase was extracted three times with ethyl acetate (50 ml each time), and the organic phase was dried over sodium sulfate and concentrated in vacuo.

Yield: 6.90 g (100%)

[1-(4-Aminomethyl-cyclohexyl)-3-phenyl-propyl]-dimethylamine (R$^1$=Me, R$^2$=Me, R$^3$=phenethyl) A17

LiAlH$_4$ (1.82 g, 48 mmol) was added, under argon, to absolute THF (360 ml); the mixture was heated to 60° C., and the oxime (6.90 g, 24 mmol), dissolved in THF (60 ml), was added dropwise. After 4 hours' stirring at 60° C., water (90 ml) was added dropwise, while cooling with an ice bath (10° C.), and the reaction solution was filtered over kieselguhr. The filter residue was washed with THF, the organic phases were combined, the THF was removed in vacuo, and the residue was adjusted to pH 11 with 5N NaOH and extracted with ethyl acetate (4×40 ml). The organic phase was dried over sodium sulfate and concentrated.

Yield: 5.6 g (85%), oil $^{13}$C-NMR (CDCl$_3$): 25.93; 26.58; 27.09; 29.21; 29.90; 30.32; 30.73; 30.77; 35.38; 35.66; 38.73; (C$_4$); 40.06; 40.90; 41.19 (N(CH$_3$)$_2$); 48.78; 65.15; 68.22 (CH); 125.36; 127.99; 128.05; 142.69.

4-(Morpholino(phenyl)methyl)cyclohexanecarbaldehyde (NR$^1$R$^2$=morpholine, R$^3$=phenyl)

A solution of potassium tert-butoxide (0.1 mol) in THF (100 ml) was added dropwise at 0° C., under argon, to a suspension of (methoxytriphenyl)phosphonium chloride (0.1 mol) in absolute THF (150 ml), and stirring was carried out for 15 min. The ketone (0.06 mol) in absolute THF (100 ml) was then added dropwise at 25° C., and stirring was carried out for 16 h. After addition of 6N HCl at 0-5° C. and stirring for one hour, extraction with ethyl acetate (10×50 ml) was carried out. The aqueous phase was then adjusted to pH 11 with 5N sodium hydroxide solution and extracted with ethyl acetate (3×100 ml). The combined organic phases were dried over Na$_2$SO$_4$ and filtered off. The solvent was removed in vacuo, and the product was used in the next stage without being purified further.

4-(Morpholino(phenyl)methyl)cyclohexanecarbaldehyde oxime (NR$^1$R$^2$=morpholine, R$^3$=phenyl)

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

C-[4-(Morpholin-4-yl-phenyl-methyl)-cyclohexyl]-methylamine (NR$^1$R$^2$=morpholine, R$^3$=phenyl) A18

The oxime (38.5 mmol) in THF (90 mol) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

4-(1-Morpholino-3-phenylpropyl)cyclohexancarbaldehyde (NR$^1$R$^2$=morpholine, R$^3$=phenethyl)

A solution of potassium tert-butoxide (0.1 mol) in THF (100 ml) was added dropwise at 0° C., under argon, to a suspension of (methoxytriphenyl)phosphonium chloride (0.1 mol) in absolute THF (150 ml), and stirring was carried out for 15 min. The ketone (0.06 mol) in absolute THF (100 ml) was then added dropwise at 25° C., and stirring was carried out for 16 h. After addition of 6N HCl at 0-5° C. and stirring for one hour, extraction with ethyl acetate (10×50 ml) was carried out. The aqueous phase was then adjusted to pH 11 with 5N sodium hydroxide solution and extracted with ethyl acetate (3×100 ml). The combined organic phases were dried over Na$_2$SO$_4$ and filtered off. The solvent was removed in vacuo, and the product was used in the next stage without being purified further.

4-(1-Morpholino-3-phenylpropyl)cyclohexanecarbaldehyde oxime (NR$^1$R$^2$=morpholine, R$^3$=phenethyl)

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

C-[4-(1-Morpholin-4-yl-3-phenyl-propyl)-cyclohexyl]-methylamine ($NR^1R^2$=morpholine, $R^3$=phenethyl) A19

The oxime (38.5 mmol) in THF (90 ml) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

4-(Phenyl(pyrrolidin-1-yl)methyl)cyclohexanecarbaldehyde ($NR^1R^2$=pyrrolidine, $R^3$=phenethyl)

A solution of potassium tert-butoxide (0.1 mol) in THF (100 ml) was added dropwise at 0° C., under argon, to a suspension of (methoxytriphenyl)phosphonium chloride (0.1 mol) in absolute THF (150 ml), and stirring was carried out for 15 min. The ketone (0.06 mol) in absolute THF (100 ml) was then added dropwise at 25° C., and stirring was carried out for 16 h. After addition of 6N HCl at 0-5° C. and stirring for one hour, extraction with ethyl acetate (10×50 ml) was carried out. The aqueous phase was then adjusted to pH 11 with 5N sodium hydroxide solution and extracted with ethyl acetate (3×100 ml). The combined organic phases were dried over $Na_2SO_4$ and filtered off. The solvent was removed in vacuo, and the product was used in the next stage without being purified further.

4-(Phenyl(pyrrolidin-1-yl)methyl)cyclohexanecarbaldehyde oxime ($NR^1R^2$=pyrrolidine, $R^3$=phenethyl)

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

C-[4-(Phenyl-pyrrolidin-1-yl-methyl)-cyclohexyl]-methylamine ($NR^1R^2$=pyrrolidine, $R^3$=phenethyl) A20

The oxime (38.5 mmol) in THF (90 ml) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

4-(3-Phenyl-1-(pyrrolidin-1-yl)propyl)cyclohexanecarbaldehyde ($NR^1R^2$=pyrrolidine, $R^3$=phenyl)

A solution of potassium tert-butoxide (0.1 mol) in THF (100 ml) was added dropwise at 0° C., under argon, to a suspension of (methoxytriphenyl)phosphonium chloride (0.1 mol) in absolute THF (150 ml), and stirring was carried out for 15 min. The ketone (0.06 mol) in absolute THF (100 ml) was then added dropwise at 25° C., and stirring was carried out for 16 h. After addition of 6N HCl at 0-5° C. and stirring for one hour, extraction with ethyl acetate (10×50 ml) was carried out. The aqueous phase was then adjusted to pH 11 with 5N sodium hydroxide solution and extracted with ethyl acetate (3×100 ml). The combined organic phases were dried over $Na_2SO_4$ and filtered off. The solvent was removed in vacuo, and the product was used in the next stage without being purified further.

4-(3-Phenyl-1-(pyrrolidin-1-yl)propyl)cyclohexanecarbaldehyde oxime ($NR^1R^2$=pyrrolidine, $R^3$=phenyl)

Amberlyst A21 (40 g) was added to a solution of the ketone (40 mmol) and hydroxylamine hydrochloride (4.17 g, 60 mmol) in absolute ethanol (200 ml), and stirring was carried out for 20 h at 25° C. After filtration and washing with ethanol (2×200 ml), the solvent was removed in vacuo. The product was used in the next stage without being purified further.

C-[4-(3-Phenyl-1-pyrrolidin-1-yl-propyl)-cyclohexyl]-methylamine ($NR^1R^2$=pyrrolidine, $R^3$=phenyl) A21

The oxime (38.5 mmol) in THF (90 ml) was added dropwise at 60° C. to a reaction mixture of lithium aluminium hydride (77 mmol) in absolute THF (400 ml), and stirring was carried out for 4 h at 60° C. Water (100 ml) was then added slowly at 10° C., and the reaction mixture was filtered off over silica. The filter residue was washed with ethyl acetate, and the solvent of the combined organic phases was removed in vacuo. The product was purified by column chromatography (5-10% methanol/dichloromethane).

Synthesis of the aminoethylcyclohexanes

The aminoethylcyclohexanes were prepared from the appropriately substituted cyclohexylaldehydes by three-stage reactions by chain extension (Wittig) and reaction with hydroxylamine hydrochloride and subsequent cleavage with lithium aluminium hydride.

[4-(Dimethylamino-phenyl-methyl)-cyclohexyl]-acetaldehyde ($R^3$=phenyl)

(Methoxymethyl)triphenylphosphonium chloride (38.39 g, 0.112 mol) was suspended in abs. THF (150 ml) under argon; potassium tert-butoxide (12.56 g, 0.112 mol), dissolved in abs. THF (120 ml) was added dropwise at 0° C., and stirring was then carried out for 15 min at 0° C. (the solution turned a deep-orange colour). The aldehyde (18.4 g, 0.075 mol), dissolved in abs. THF (120 ml), was then added dropwise at RT, and stirring was carried out overnight at RT. Hydrolysis was carried out dropwise with water (50 ml) and 6N HCl (150 ml), while cooling with ice-water. After one hour's stirring at RT, extraction with diethyl ether (10×100 ml) was carried out. The aqueous phase was adjusted to pH 11 with 5N NaOH, extracted by shaking with ethyl acetate (3×80 ml), dried over sodium sulfate and concentrated in vacuo. The crude product was purified by flash chromatography with ethyl acetate/cyclohexane (1:1).

Yield: 16.31 g (84%), oil $^{13}$C-NMR (CDCl$_3$): 25.30; 25.92; 29.04; 29.19; 29.74; 30.86; 32.99; 33.02; 35.98; 38.31 (C$_4$); 41.42; 42.06; (N(CH$_3$)$_2$); 48.04; 51.24; 71.82; 75.47 (CH); 126.64 (C$_{arom}$); 126.68 (C$_{arom}$); 127.39 (C$_{arom}$); 127.46 (C$_{arom}$); 129.15 (C$_{arom}$); 136.20 (C$_{arom}$); 137.11 (C$_{arom}$); 202.27; 202.37 (CHO).

[4-(Dimethylamino-phenyl-methyl)-cyclohexyl]-acetaldehyde oxime (R$^3$=phenyl)

The carbaldehyde (11.04 g, 42.5 mmol) and hydroxylamine hydrochloride (4.44 g, 64 mmol) were dissolved in abs. ethanol (150 ml); basic ion exchanger Amberlyst A21 (30 g) was added thereto, and stirring was carried out for 4 h at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.
Yield: 11.66 (100%)
$^{13}$C-NMR (CDCl$_3$): 25.41; 25.57; 28.87; 29.11; 30.92; 30.97; 32.33; 32.99; 33.67; 35.99; 36.10; 38.59 (C$_4$); 41.31; 41.40; 42.11; 42.14 (N(CH$_3$)$_2$); 71.74; 75.63 (CH); 126.71 (C$_{arom}$); 127.46 (C$_{arom}$); 129.26 (C$_{arom}$); 137.26 (C$_{arom}$); 150.95; 151.37; 151.56 (C=N—O).

2-[4-Dimethylamino-phenyl-methyl)-cyclohexyl]-ethylamine (R$^3$=phenyl) A22

LiAlH$_4$ (3.22 g, 85 mmol) was added, under argon, to absolute THF (400 ml); the mixture was heated to 60° C., and the oxime (11.66 g, 42.5 mmol), dissolved in THF (80 ml), was added dropwise. After 4 hours' stirring at 60° C., water (100 ml) was added dropwise, while cooling with an ice bath (10° C.), and the reaction solution was filtered off over kieselguhr and the kieselguhr was washed with THF. The combined THF solutions were concentrated in vacuo, and the residue was adjusted to pH 11 with 5N NaOH and extracted with ethyl acetate (4×50 ml). The organic phase was dried over sodium sulfate and concentrated by evaporation.
Yield: 9.15 g (83%), oil
$^{13}$C-NMR (CDCl$_3$): 25.58; 26.08; 29.16; 29.21; 30.39; 31.10; 32.49; 33.16; 33.33; 35.54; 36.22; 38.80 (C$_4$); 40.32; 41.36; 41.50; 42.11; (N(CH$_3$)$_2$); 71.77; 75.66 (CH); 126.52 (C$_{arom}$); 127.31 (C$_{arom}$); 127.38 (C$_{arom}$); 129.18 (C$_{arom}$); 139.39 (C$_{arom}$); 137.41 (C$_{arom}$).

{4-[Dimethylamino-(4-fluorophenyl)-methyl]-cyclohexyl}-acetaldehyde (R$^3$=4-fluorophenyl)

(Methoxymethyl)triphenylphosphonium chloride (43.53 g, 127 mmol) was suspended in abs. THF (200 ml) under argon; potassium tert-butoxide (14.25 g, 127 mmol), dissolved in abs. THF (130 ml), was added dropwise at 0° C., and stirring was then carried out for 15 min at 0° C.
The aldehyde (22.3 g, 85 mmol), dissolved in abs. THF (130 ml), was then added dropwise at RT, and stirring was carried out overnight at RT. Hydrolysis was carried out dropwise with water (80 ml) and 6N HCl (200 ml), while cooling with ice-water. After one hour's stirring at RT, extraction was carried out ten times with diethyl ether (100 ml each time). The aqueous phase was adjusted to pH 11 with 5N NaOH, extracted by shaking three times with ethyl acetate (100 ml each time), dried over sodium sulfate and concentrated in vacuo. The crude product was purified by flash chromatography with ethyl acetate/cyclohexane (1:1). Yield: 15.8 g (67%)
$^{13}$C-NMR (CDCl$_3$): δ=25.08; 25.87; 28.80; 29.10; 29.13; 29.62; 30.82; 32.90; 33.08; 36.19; 38.43; 41.36; 42.01; 47.94; 51.17; 71.11; 74.69; 114.11; 114.20; 114.32; 130.32; 130.40; 132.00; 132.92; 160.31; 162.74; 202.15; 202.23.

{4-[Dimethylamino-(4-fluorophenyl)-methyl]-cyclohexyl}-acetaldehyde oxime (R$^3$=4-fluorophenyl)

The carbaldehyde (5.30 g, 20.0 mmol) and hydroxylamine hydrochloride (2.08 g, 30 mmol) were dissolved in abs. ethanol (90 ml); basic ion exchanger Amberlyst A21 (14.8 g) was added thereto, and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×100 ml), and the organic phase was dried over sodium sulfate and concentrated in vacuo. The residue was purified by flash chromatography with EE/cyclohexane (2:1).
Yield: 3.50 (60%)

2-{(4-[Dimethylamino-(4-fluorophenyl)-methyl]-cyclohexyl}-ethylamine A23 (R$^3$=4-fluorophenyl)

LiAlH$_4$ (2.35 g, 62 mmol) was added, under argon, to absolute THF (450 ml); the mixture was heated to 60° C., and the oxime (9.10 g, 31.0 mmol), dissolved in THF (75 ml), was added dropwise. After 4 hours' stirring at 60° C., water (116 ml) was added dropwise, while cooling with an ice bath (10° C.), and the reaction solution was filtered off over kieselguhr and the kieselguhr was washed with THF. The combined THF solutions were concentrated in vacuo, and the residue was adjusted to pH 11 with 5N NaOH and extracted with ethyl acetate (4×50 ml). The organic phase was dried over sodium sulfate and concentrated in vacuo.
Yield: 6.80 g (79%), oil
$^{13}$C-NMR (CDCl$_3$): 25.32; 26.03; 28.94; 29.08; 30.37; 31.06; 32.39; 32.90; 33.07; 33.26; 35.50; 37.81; 38.80 39.78 (C$_4$); 41.33; 41.42; 42.09 (N(CH$_3$)$_2$); 71.11; 74.89 (CH); 114.03; 114.11; 130.32; 130.40; 132.19; 133.18; 133.21; 160.27; 162.69.

{4-[Dimethylamino-(3-fluorophenyl)-methyl]-cyclohexyl}-acetaldehyde (R$^3$=3-fluorophenyl)

(Methoxymethyl)triphenylphosphonium chloride (26.73 g, 78 mmol) was suspended in abs. THF (90 ml) under argon; potassium tert-butoxide (8.75 g, 78 mmol), dissolved in abs. THF (90 ml), was added dropwise at 0° C., and stirring was then carried out for 15 min at 0° C.
The aldehyde (13.69 g, 52 mmol), dissolved in abs. THF (90 ml), was then added dropwise at RT, and stirring was carried out overnight at RT. Hydrolysis was carried out dropwise with water (50 ml) and 6N HCl (150 ml), while cooling with ice-water. After one hour's stirring at RT, extraction was carried out ten times with diethyl ether (50 ml each time). The aqueous phase was adjusted to pH 11 with 5N NaOH, extracted by shaking three times with ethyl acetate (100 ml each time), dried over sodium sulfate and concentrated in vacuo. The crude product was purified by flash chromatography with ethyl acetate/cyclohexane (1:1).
Yield: 12.61 g (87%)
$^{13}$C-NMR (CDCl$_3$): δ=25.19; 25.83; 28.90; 29.06; 29.14; 29.68; 30.77; 32.92; 32.98; 33.10; 36.05; 38.36; 41.39; 42.04; 48.02; 51.20; 71.48; 75.07; 113.43; 113.49; 113.64; 113.69;

115.55; 115.76; 124.89; 128.70; 128.78; 128.88; 139.24; 140.08; 140.14; 161.09; 163.52; 202.19; 202.27.

{4-[Dimethylamino-(3-fluorophenyl)-methyl]-cyclohexyl}-acetaldehyde oxime ($R^3$=3-fluorophenyl)

The carbaldehyde (7.18 g, 25.8 mmol) and hydroxylamine hydrochloride (2.71 g, 39 mmol) were dissolved in abs. ethanol (90 ml); basic ion exchanger Amberlyst A21 (20 g) was added thereto, and stirring was carried out for 20 h at RT. The ion exchanger was filtered out and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.

Yield: 7.54 (100%)

2-{4-[Dimethylamino-(3-fluorophenyl)-methyl]-cyclohexyl}-ethylamine ($R^3$=3-fluorophenyl) A24

LiAlH$_4$ (1.97 g, 52 mmol) was added, under argon, to absolute THF (300 ml); the mixture was heated to 60° C., and the oxime (7.54 g, 25.8 mmol), dissolved in THF (70 ml), was added dropwise. After 4 hours' stirring at 60° C., water (100 ml) was added dropwise, while cooling with an ice bath (10° C.), and the reaction solution was filtered off over kieselguhr and the kieselguhr was washed with THF. The combined THF solutions were concentrated in vacuo, and the residue was adjusted to pH 11 with 5N NaOH and extracted with ethyl acetate (3×50 ml). The organic phase was dried over sodium sulfate and concentrated in vacuo.

Yield: 6.3 g (88%), oil $^{13}$C-NMR (CDCl$_3$): 25.28; 25.84; 28.87; 28.98; 30.28; 32.30; 32.93; 33.13; 35.38; 36.16; 37.81; 38.69 (C$_4$); 39.69; 41.20; 41.37; 41.94 (N(CH$_3$)$_2$); 71.29; 75.11 (CH); 113.14; 113.18; 113.38; 115.41; 115.62; 124.73; 128.44; 128.53; 139.25; 140.27; 140.33; 160.91; 163.34.

{4-[(4-Chlorophenyl)-dimethylamino-methyl]-cyclohexyl}-acetaldehyde ($R^3$=4-chlorophenyl)

(Methoxymethyl)triphenylphosphonium chloride (25.02 g, 73 mmol) was suspended in abs. THF (90 ml) under argon; potassium tert-butoxide (8.19 g, 73 mmol), dissolved in abs. THF (90 ml), was added dropwise at 0° C., and stirring was then carried out for 15 min at 0° C.

The aldehyde (13.86 g, 49 mmol), dissolved in abs. THF (90 ml), was then added dropwise at RT, and stirring was carried out overnight at RT. Hydrolysis was carried out dropwise with water (50 ml) and 6N HCl (150 ml), while cooling with ice-water. After one hour's stirring at RT, extraction was carried out ten times with diethyl ether (50 ml each time). The aqueous phase was adjusted to pH 11 with 5N NaOH, extracted by shaking three times with ethyl acetate (100 ml each time), dried over sodium sulfate and concentrated in vacuo. The crude product was purified by flash chromatography with ethyl acetate/cyclohexane (1:1). Yield: 12.07 g (84%).

$^{13}$C-NMR (CDCl$_3$): δ=25.06; 25.82; 28.74; 29.00; 29.13; 29.60; 30.77; 32.87; 32.94; 33.07; 36.06; 38.32; 41.38; 42.05; 47.95; 51.17; 71.23; 74.80; 127.58; 127.66; 130.31; 132.28; 132.34; 134.81; 135.77; 202.12; 202.20.

{4-[Dimethylamino-(4-chlorophenyl)-methyl]-cyclohexyl}-acetaldehyde oxime ($R^3$=4-chlorophenyl)

The carbaldehyde (6.72 g, 22.8 mmol) and hydroxylamine hydrochloride (2.36 g, 34 mmol) were dissolved in abs. ethanol (90 ml); basic ion exchanger Amberlyst A21 (16 g) was added thereto, and stirring was carried out for 20 h at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.

Yield: 7.04 (100%)

2-{4-[Dimethylamino-(4-chlorophenyl)-methyl]-cyclohexyl}-ethylamine ($R^3$=4-chlorophenyl) A25

LiAlH$_4$ (1.73 g, 45.6 mmol) was added, under argon, to absolute THF (300 ml); the mixture was heated to 60° C., and the oxime (7.04 g, 22.8 mmol), dissolved in THF (60 ml), was added dropwise. After 4 hours' stirring at 60° C., water (100 ml) was added dropwise, while cooling with an ice bath (10° C.), and the reaction solution was filtered off over kieselguhr and the kieselguhr was washed with THF. The combined THF solutions were concentrated in vacuo, and the residue was adjusted to pH 11 with 5N NaOH and extracted with ethyl acetate (3×50 ml). The organic phase was dried over sodium sulfate and concentrated in vacuo.

Yield: 5.76 g (86%), oil $^{13}$C-NMR (CDCl$_3$): 25.67; 26.35; 29.23; 29.44; 30.74; 31.39; 33.41; 33.61; 35.86; 36.71; 38.20; 39.18; 40.17; 40.67; 41.72; 41.81; 42.50 (N(CH$_3$)$_2$); 71.59; 75.37; 127.86; 127.95; 130.70; 132.52; 135.38; 136.45.

{4-[Dimethylamino-thiophen-2-yl-methyl]-cyclohexyl}-acetaldehyde ($R^3$=2-thienyl)

(Methoxymethyl)triphenylphosphonium chloride (28.79 g, 84 mmol) was suspended in abs. THF (100 ml) under argon; potassium tert-butoxide (9.42 g, 84 mmol), dissolved in abs. THF (100 ml), was added dropwise at 0° C., and stirring was then carried out for 15 min at 0° C.

The aldehyde (14.08 g, 56 mmol), dissolved in abs. THF (100 ml), was then added dropwise at RT, and stirring was carried out overnight at RT. Hydrolysis was carried out dropwise with water (50 ml) and 6N HCl (150 ml), while cooling with ice-water. After one hour's stirring at RT, extraction was carried out ten times with diethyl ether (50 ml each time). The aqueous phase was adjusted to pH 11 with 5N NaOH, extracted by shaking three times with ethyl acetate (100 ml each time), dried over sodium sulfate and concentrated in vacuo. The crude product was purified by flash chromatography with ethyl acetate/cyclohexane (1:2). Yield: 11.48 g (77%).

$^{13}$C-NMR (CDCl$_3$): δ=25.80; 25.88; 28.73; 29.95; 30.49; 32.23; 32.76; 37.89; 40.21; 40.88; 41.23; 48.36; 51.09; 66.02; 69.97; 123.19; 123.72; 125.95; 126.31; 139.42; 139.91; 202.61.

[4-(Dimethylamino-thiophen-2-yl-methyl)-cyclohexyl]-acetaldehyde oxime ($R^3$=2-thiophene)

The carbaldehyde (6.3 g, 23.7 mmol) and hydroxylamine hydrochloride (2.5 g, 36 mmol) were dissolved in abs. ethanol (90 ml); basic ion exchanger Amberlyst A21 (20 g) was added thereto, and stirring was carried out for 20 h at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.

Yield: 6.64 (100%)

2-[4-(Dimethylamino-thiophen-2-yl-methyl)-cyclohexyl]-ethylamine (R³=2-thiophene) A26

LiAlH₄ (1.78 g, 47 mmol) was added, under argon, to absolute THF (250 ml); the mixture was heated to 60° C., and the oxime (6.64 g, 23.7 mmol), dissolved in THF (60 ml), was added dropwise. After 4 hours' stirring at 60° C., water (100 ml) was added dropwise, while cooling with an ice bath (10° C.), and the reaction solution was filtered off over kieselguhr and the kieselguhr was washed with THF. The combined THF solutions were concentrated in vacuo, and the residue was adjusted to pH 11 with 5N NaOH and extracted with ethyl acetate (3×50 ml). The organic phase was dried over sodium sulfate and concentrated in vacuo.

Yield: 5.62 g (89%), oil $^{13}$C-NMR (CDCl₃): 25.97; 26.13; 28.72; 28.79; 30.15; 30.23; 30.74; 32.61; 32.90; 35.32; 38.22; 39.70; 40.09; 40.69; 40.84; 41.26 (N(CH₃)₂); 70.14; 123.56; 123.60; 125.86; 126.21; 126.23; 139.70; 140.24.

[4-(1-Dimethylamino-3-phenyl-propyl)-cyclohexyl]-acetaldehyde (R³=phenethyl)

(Methoxymethyl)triphenylphosphonium chloride (50.3 g, 147 mmol) was suspended in abs. THF (150 ml) under argon; potassium tert-butoxide (16.5 g, 147 mmol), dissolved in abs. THF (140 ml), was added dropwise at 0° C., and stirring was then carried out for 15 min at 0° C.

The aldehyde (27.0 g, 98 mmol), dissolved in abs. THF (150 ml), was then added dropwise at RT, and stirring was carried out overnight at RT. Hydrolysis was carried out dropwise with water (102 ml) and 6N HCl (240 ml), while cooling with ice-water. After one hour's stirring at RT, extraction was carried out five times with diethyl ether (200 ml each time). The aqueous phase was adjusted to pH 11 with 5N NaOH, extracted by shaking three times with ethyl acetate (200 ml each time), dried over sodium sulfate and concentrated in vacuo. The crude product was purified by flash chromatography with ethyl acetate/cyclohexane (1:1). Yield: 18.1 g (64%)

$^{13}$C-NMR (CDCl₃): δ=25.55; 26.19; 29.04; 29.15; 29.35; 29.85; 31.00; 32.87; 32.68; 33.04; 35.33; 38.49; 40.86; 41.13; 47.51; 51.15; 65.48; 68.09.

[4-(1-Dimethylamino-3-phenyl-propyl)-cyclohexyl]-acetaldehyde oxime (R³=phenethyl)

The carbaldehyde (12.6 g, 44.0 mmol) and hydroxylamine hydrochloride (4.60 g, 66.0 mmol) were dissolved in abs. ethanol (200 ml); basic ion exchanger Amberlyst A21 (32 g) was added thereto, and stirring was carried out overnight at RT. The ion exchanger was filtered off and washed with ethanol (2×50 ml). The solution was concentrated, the residue was adjusted to pH 11 with 5N NaOH, the aqueous phase was extracted with ethyl acetate (3×50 ml), and the organic phase was dried over sodium sulfate and concentrated in vacuo.

Yield: 13.3 (100%)

{1-[4-(2-Amino-ethyl)-cyclohexyl]-3-phenyl-propyl}-dimethylamine (R³=phenethyl) A27

LiAlH₄ (4.25 g, 112 mmol) was added, under argon, to absolute THF (600 ml); the mixture was heated to 60° C., and the oxime 71 (17.1 g, 56.0 mmol), dissolved in THF (150 ml), was added dropwise. After 4 hours' stirring at 60° C., water (360 ml) was added dropwise, while cooling with an ice bath (10° C.), and the reaction solution was filtered off over kieselguhr and the kieselguhr was washed with THF. The combined THF solutions were concentrated in vacuo, and the residue was adjusted to pH 11 with 5N NaOH and extracted with ethyl acetate (5×100 ml). The organic phase was dried over sodium sulfate and concentrated in vacuo.

Yield: 16.2 g (100%), oil $^{13}$C-NMR (CDCl₃): 25.67; 26.44; 29.07; 29.16; 30.05; 30.22; 31.32; 31.80; 33.30; 35.24; 35.37; 37.26; 39.77; 40.30; 40.85; 41.15; 41.40 (N(CH₃)₂); 65.61; 68.29; 125.53; 127.68; 128.16; 128.200; 142.91.

Synthesis of the Piperidine Derivatives

Commercially available isonipecotic acid methyl ester was used as starting material for the piperidine derivatives; it was first N-protected, in order subsequently to reduce the ester function to the aldehyde. The introduction of the N,N-dimethyl(aryl)methanamine radical was carried out analogously to the cyclohexylamine derivatives. Deprotection yielded the desired product.

Methyl 1-(4-methoxybenzyl)piperidine-4-carboxylate

4-Methoxybenzyl chloride (1.10 g, 6.98 mmol) was added dropwise to a solution of isonipecotic acid methyl ester (1.00 g, 6.98 mmol) and triethylamine (1.40 g, 14 mmol) in THF (30 ml), and stirring was carried out for 72 h at 60° C. 5% sodium hydrogen carbonate solution (50 ml) was then added to the reaction mixture, and extraction with ethyl acetate (3×50 ml) was carried out. The combined organic phases were dried over sodium sulfate and concentrated in vacuo. The residue was purified by flash chromatography with cyclohexane/ethyl acetate (2:1).

Yield: 1.23 g (67%) of methyl 1-(4-methoxybenzyl)piperidine-4-carboxylate $^{1}$H-NMR (DMSO-d₆): 1.53 (dq, 2H); 1.77 (dd, 2H); 1.93 (dt, 2H); 2.28 (tt, 1H); 2.71 (td, 2H); 3.35 (s, 2H); 3.58 (s, 3H); 3.72 (s, 3H); 6.86 (d, 2H); 7.17 (d, 2H).

1-(4-Methoxybenzyl)piperidine-4-carbaldehyde

A 1.5 M solution of diisobutylaluminium hydride in toluene (3.12 ml, 4.68 mmol) was added dropwise under argon at −78° C., in the course of 30 minutes, to a solution of methyl 1-(4-methoxybenzyl)piperidine-4-carboxylate (1.23 g, 4.68 mmol) in toluene (30 ml), and stirring was then carried out for 30 min at that temperature. Methanol (15 ml) was then added dropwise in such a manner that the internal temperature remained at −78° C., before the mixture was then slowly warmed to room temperature. Saturated sodium chloride solution (20 ml) was added to the reaction mixture, and the suspension was filtered through sea sand. The organic phase was dried over sodium sulfate and concentrated in vacuo. The residue was purified by flash chromatography with cyclohexane/ethyl acetate (1:3).

Yield: 750 mg (69%) of 1-(4-methoxybenzyl)piperidine-4-carbaldehyde $^{1}$H-NMR (DMSO-d₆): 1.47 (dtd, 2H); 1.78 (m, 2H); 2.00 (dt, 2H); 2.27 (m, 1H); 2.66 (td, 2H); 3.36 (s, 2H); 3.73 (s, 3H); 6.86 (d, 2H); 7.18 (d, 2H); 9.57 (s, 1H).

2-(Dimethylamino)-2-(1-(4-methoxybenzyl)piperidin-4-yl)acetonitrile (R¹, R²=methyl)

40% aqueous dimethylamine solution (2.66 ml, 21 mmol), 1-(4-methoxybenzyl)-piperidine-4-carbaldehyde (750 mg, 3.2 mmol) and potassium cyanide (688 mg, 10.6 mmol) were added, while cooling with ice, to a mixture of 4 N hydrochloric acid (1.2 ml) and methanol (5 ml). The reaction mixture was stirred for 5 d at room temperature, then water (50 ml) was added and extraction with ethyl acetate was carried out (3×50 ml). The combined organic phases were dried over sodium sulfate and concentrated in vacuo.

Yield: 875 mg (95%) of 2-(dimethylamino)-2-(1-(4-methoxybenzyl)piperidine-4-yl)acetonitrile $^1$H-NMR (DMSO-$d_6$): 1.22-1.29 (m, 2H); 1.57 (ddt, 1H); 1.76-1.97 (m, 4H); 2.18 (s, 6H); 2.73-2.88 (m, 3H); 3.36 (s, 3H); 3.73 (s, 2H); 6.85 (d, 2H); 7.16 (d, 2H).

(1-(4-Methoxybenzyl)piperidin-4-yl)-N,N-dimethyl (phenyl)methanamine ($R^1$, $R^2$=methyl, $R^3$=phenyl)

A 2 M phenylmagnesium chloride solution in THF (3.75 ml, 7.5 mmol) was added dropwise to an ice-cooled solution of 2-(dimethylamino)-2-(1-(4-methoxybenzyl)piperidin-4-yl)acetonitrile (875 mg, 3.0 mmol) in THF (20 ml), and then the reaction mixture was heated slowly to room temperature and stirred for 16 h. Saturated ammonium chloride solution (50 ml) was then added to the reaction solution, extraction with ethyl acetate (3×50 ml) was carried out, the combined organic phases were dried over sodium sulfate and concentrated in vacuo, and the residue was purified by flash chromatography with chloroform/methanol/triethylamine (9:1:0.1).

Yield: 832 mg (82%) of 1-(1-(4-methoxybenzyl)piperidin-4-yl)-N,N-dimethyl-1-phenylmethanamine $^1$H-NMR (DMSO-$d_6$): 0.84-1.18 (m, 3H); 1.74-1.89 (m, 4H); 1.99 (s, 6H); 2.68 (d, 1H); 2.80 (d, 1H); 3.07 (d, 1H, J=8.9 Hz); 3.32 (s, 2H); 3.71 (s, 3H); 6.84 (d, 2H); 7.15 (q, 4H); 7.21-7.33 (m, 3H).

Benzyl 4-((dimethylamino)(phenyl)methyl)piperidine-1-carboxylate ($R^1$, $R^2$=methyl, $R^3$=phenyl)

Chloroformic acid benzyl ester (1.50 g, 1.25 ml, 8.86 mmol) was added to a solution of 1-(1-(4-methoxybenzyl)piperidin-4-yl)-N,N-dimethyl-1-phenylmethanamine (3.00 g, 8.86 mmol) in DCM (50 ml), and stirring was carried out for 30 min at room temperature. Sodium hydrogen carbonate solution (40 ml) was then added to the reaction mixture, the phases were separated, and the aqueous phase was extracted with DCM (2×30 ml). The combined organic phases were dried over sodium sulfate and concentrated in vacuo, and the residue was purified by flash chromatography with chloroform/methanol/triethylamine (100:5:1).

Yield: 2.32 g (74%) of benzyl 4-((dimethylamino)(phenyl)methyl)piperidine-1-carboxylate $^1$H-NMR (DMSO-$d_6$): 0.82 (ddd, 2H); 0.97 (ddd, 2H); 1.27 (d, 1H); 2.00 (s, 6H); 2.69-2.84 (m, 2H); 3.11 (d, 1H); 3.89 (d, 1H); 4.03 (d, 1H); 5.03 (s, 2H); 7.14 (m, 2H); 7.20-7.35 (m, 8H).

N,N-Dimethyl-1-phenyl-1-(piperidin-4-yl)methanamine ($R^1$, $R^2$=methyl, $R^3$=phenyl) A28

33% hydrogen bromide in glacial acetic acid (20 ml) was added to a solution of benzyl 4-((dimethylamino)(phenyl)methyl)piperidine-1-carboxylate (2.32 g, 6.58 mmol) in glacial acetic acid (20 ml), and stirring was carried out for 1.5 h at room temperature. A solid was precipitated by addition of diethyl ether. The supernatant solution was decanted off; diethyl ether was added repeatedly to the residue, and the supernatant solution was decanted off again each time. The residue was dried in vacuo and dissolved in methanol (20 ml); strongly basic ion exchanger Dowex 1×2-200 was added thereto, and stirring was carried out for 1 h at room temperature. The mixture was then filtered, the filter residue was washed with methanol, and the filtrate was concentrated in vacuo.

Yield: 1.09 g (76%) of N,N-dimethyl-1-phenyl-1-(piperidin-4-yl)methanamine $^1$H-NMR (DMSO-$d_6$): 1.06 (ddd, 1H); 1.23 (td, 2H); 1.72 (br s, 1H); 1.99 (s, 6H); 2.20 (dd, 1H); 2.66 (dt, 1H); 2.77 (dt, 1H); 3.03 (d, 1H); 3.10 (d, 1H); 3.17 (d, 1H); 7.15 (d, 2H); 7.25 (m, 1H); 7.34 (m, 2H).

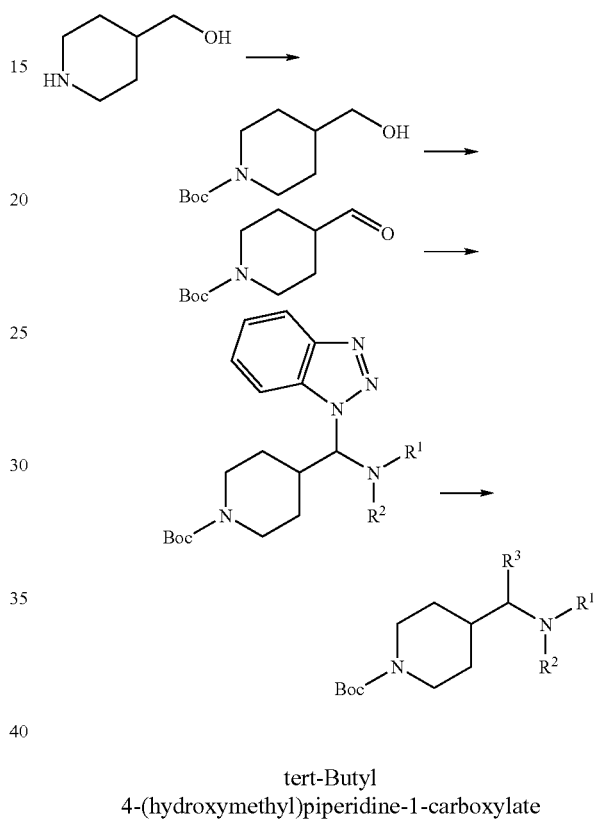

tert-Butyl 4-(hydroxymethyl)piperidine-1-carboxylate

Triethylamine (1.5 equivalents) and Boc anhydride (1.2 equivalents) were added at 0° C. to a solution of 4-hydroxymethylpiperidine in DMC, and stirring was carried out for 1 h at 25° C. After addition of DCM, the organic phase was separated off and washed with water and saturated aqueous NaCl solution. After drying the organic phase over $Na_2SO_4$ and filtration, the solvent was removed in vacuo. The product was purified by column chromatography (30% ethyl acetate/hexane).

tert-Butyl 4-formylpiperidine-1-carboxylate

DMSO (2.2 equivalents) was added at −78° C., under an inert gas atmosphere, to a solution of oxalyl chloride (1.1 equivalents) in dry $CH_2Cl_2$, and stirring was carried out for 1 h. A solution of N-Boc-4-piperidinemethanol (1 equivalent) in dry DCM was added dropwise to the reaction mixture at −70° C., and stirring was carried out for 2 h. After addition of triethylamine (2.5 equivalents), the reaction solution was allowed to warm to RT, and saturated aqueous $NH_4Cl$ solution and DCM were added thereto. The organic phase was separated and washed with water and saturated aqueous NaCl solution. After drying the organic phase over $Na_2SO_4$ and filtration, the solvent was removed in vacuo. The product was used in the next stage without being purified further.

tert-Butyl 4-((1H-benzo[d][1,2,3]triazol-1-yl)(morpholino)methyl)piperidine-1-carboxylate The aldehyde (23.4 mmol), morpholine (23.4 mmol) and 1H-benzotriazole (23.4 mmol) were heated for 16 h under reflux in benzene (60 ml), and the resulting water of reaction was removed by means of a water separator. The benzene was removed in vacuo and the residue was used directly in the next stage.

tert-Butyl 4-(morpholino(phenyl)methyl)piperidine-1-carboxylate (NR$^1$R$^2$=morpholine, R$^3$=phenyl) X1

A solution of the benzotriazole adduct (23.5 mmol) in THF was added dropwise to a solution of the Grignard reagent (47.1 mmol) in THF, and stirring was carried out for 16 h at 25° C. The reaction solution was cooled to 0° C.; saturated aqueous NH$_4$Cl solution was added thereto, and then extraction with ethyl acetate (2×300 ml) was carried out. The organic phase was washed with water and saturated aqueous NaCl solution. After drying the organic phase over Na$_2$SO$_4$ and filtration, the solvent was removed in vacuo. The product was purified by column chromatography (2-5% methanol/dichloromethane).

tert-Butyl 4-(morpholino(benzyl)methyl)piperidine-1-carboxylate carboxylate (NR$^1$R$^2$=morpholine, R$^3$=benzyl) X2

A solution of the benzotriazole adduct (23.5 mmol) in THF was added dropwise to a solution of the Grignard reagent (47.1 mmol) in THF, and stirring was carried out for 16 h at 25° C. The reaction solution was cooled to 0° C.; saturated aqueous NH$_4$Cl solution was added thereto, and then extraction with ethyl acetate (2×300 ml) was carried out. The organic phase was washed with water and saturated aqueous NaCl solution. After drying the organic phase over Na$_2$SO$_4$ and filtration, the solvent was removed in vacuo. The product was purified by column chromatography (2-5% methanol/dichloromethane).

The amines A29 and A30 were obtained from X1 and X2 by acid cleavage of the Boc group.

Synthesis of amine structural units A31-A35

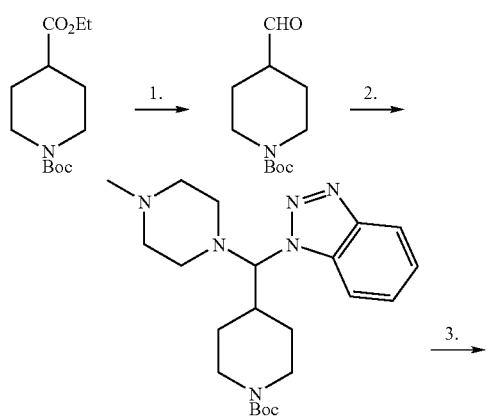

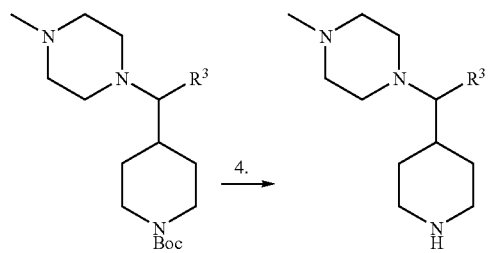

Stage 1. Diisobutylaluminium hydride (15.3 mmol, 1.5 M solution in toluene) was added dropwise at −70° C., under an argon atmosphere, to a solution of piperidine-1,4-dicarboxylic acid 1-tert-butyl ester 4-ethyl ester (15 mmol) in dry toluene (20 ml), and stirring was carried out for 2 hours at that temperature. When the reaction was complete (TLC monitoring), methanol (20 ml) was added at −70° C. and the reaction mixture was heated to RT. A saturated sodium chloride solution was added (30 ml), and the mixture was filtered over silica gel. Washing with ethyl acetate was then carried out, and the aqueous phase was separated off and extracted again with ethyl acetate. The combined organic phases were washed with saturated sodium chloride solution and then dried over sodium sulfate and concentrated. The crude product was used further without being purified further.

Stage 2. tert-Butyl 4-formylpiperidine-1-carboxylate (15 mmol), N-methylpiperazine (15 mmol) and benzotriazole (15 mmol) in benzene (60 ml) were heated under reflux in a Dean-Stark water separator. The solvent was then removed under reduced pressure. The resulting crude product was used further without being purified further.

Stage 3. tert-Butyl 4-((1H-benzo[d][1,2,3]triazol-1-yl)(4-methylpiperazin-1-yl)-methyl)piperidine-1-carboxylate (12 mmol) in THF was added dropwise at 0° C. to a solution of the corresponding Grignard reagent in THF (60 mmol). The reaction mixture was heated to 25° C. and stirred at that temperature for 16 h (TLC monitoring). The mixture was then cooled to 0° C., saturated ammonium chloride solution was added, and extraction with ethyl acetate was carried out. The organic phase was washed in succession with water and saturated sodium chloride solution and dried over sodium sulfate. The solvent was removed and the resulting crude product was purified by column chromatography (silica gel, DCM/methanol, 98:2→95:5).

Stage 4. TFA (20% in DCM, 5 ml/mmol) was added at 0° C. to the Boc-protected compound, and stirring was then carried out for 3 h at room temperature (TLC monitoring). The solvent was removed completely and the crude product (TFA salt) was used further without being purified further.

The following amine structural units were prepared according to the process described above:

| Name | | R$^3$ |
|---|---|---|
| A31 | 1-((3-fluorophenyl)(piperidin-4-yl)methyl)-4-methyl-piperazine | |

-continued

| Name | | R³ |
|---|---|---|
| A32 | 1-((4-fluorophenyl)(piperidin-4-yl)methyl)-4-methyl-piperazine | 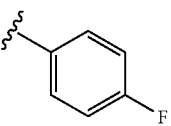 |
| A33 | 1-methyl-4-(phenyl(piperidin-4-yl)methyl)-piperazine | 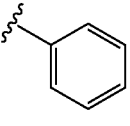 |
| A34 | 1-methyl-4-(2-phenyl-1-(piperidin-4-yl)ethyl)-piperazine | 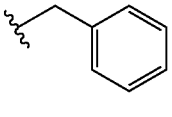 |
| A35 | 1-methyl-4-(3-phenyl-1-(piperidin-4-yl)propyl)-piperazine | 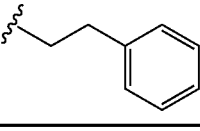 | b) Preparation of the Acid Structural Units

TABLE 2

Examples of acid structural units

| S1 | 2-(2-(3,4-dichlorophenylsulfonyl)-1,2,3,4-tetrahydroisoquinolin-1-yl)-acetic acid |
|---|---|
| S2 | 2-(2-(3,4-dichloro-N-methylphenylsulfonamido)phenyl)acetic acid |
| S3 | 3-((3,4-dichloro-N-methylphenylsulfonamido)methyl)benzoic acid |
| S4 | 2-(3,4-dichloro-N-methylphenylsulfonamido)benzoic acid |
| S5 | 2-(3,4-dichloro-N-methylphenylsulfonamido)-4,5,6,7-tetrahydrobenzo-[b]thiophene-3-carboxylic acid |
| S6 | 1-(3,4-dichlorophenylsulfonyl)indoline-2-carboxylic acid |
| S7 | 1-(4-methoxyphenylsulfonyl)indoline-2-carboxylic acid |
| S8 | 2-(1-(3-(trifluoromethyl)phenylsulfonyl)piperidin-2-yl)acetic acid |
| S9 | 1-(4-methoxy-N-methylphenylsulfonamido)cyclohexanecarboxylic acid |
| S10 | 5-(2,4,6-trichloro-N-methylphenylsulfonamido)pentanoic acid |
| S11 | 2-(1-(2,4-dichlorophenylsulfonyl)-3-oxopiperazin-2-yl)acetic acid |
| S12 | 2-(1-(3,4-dichlorophenylsulfonyl)-3-oxo-1,2,3,4-tetrahydroquinoxalin-2-yL)acetic acid |
| S13 | 2-(1-(3,4-dichlorophenylsulfonyl)pyrrolidin-2-yl)acetic acid |
| S14 | 2-(1-(3,4-dichlorophenylsulfonyl)piperidin-2-yl)acetic acid |
| S15 | 2-(2-(4-methoxyphenylsulfonyl)-1,2,3,4-tetrahydroisoquinolin-1-yl)acetic acid |
| S16 | 3-(naphthalene-2-sulfonamido)-3-phenylpropionic acid |
| S17 | 3-(1-(4-chloro-2,5-dimethylphenylsulfonyl)piperidin-2-yl)propionic acid |

Synthesis of 2-(2-(3,4-dichlorophenylsulfonyl)-1,2,3,4-tetrahydroisoquinolin-1-yl)-acetic acid S1

N-Bromosuccinimide (30.6 g, 172 mmol) was added in portions, over a period of 15 min, to a stirred solution of 1,2,3,4-tetrahydroisoquinoline (20.80 g, 156 mmol) in DCM (400 ml). The reaction solution was stirred until the starting material had reacted completely (TLC monitoring). NaOH (100 ml of a 30% aqueous solution) was then added, and stirring was carried out for 1 h at room temperature. The phases were separated and the organic phase was washed with water (200 ml). The product was extracted with HCl (10% aqueous solution, 2×200 ml), and the combined acidic aqueous solutions were washed with DCM. The mixture was then rendered basic (pH 9) with ammonia, and the oil that had separated off was extracted with DCM (3×200 ml). Drying over sodium sulfate and concentration yielded a yellowish oil.
Yield: (20.0 g, 98%)

2-(1,2,3,4-Tetrahydroisoquinolin-1-yl)acetic acid 3,4-Dihydroisoquinoline (20.0 g, 152 mmol) and malonic acid (15.9 g, 152 mmol) were mixed thoroughly at room temperature. The mixture was immersed in an oil bath preheated to 120° C., and was mixed further manually. After 30 min, no further evolution of gas was to be observed and the mixture was cooled to room temperature. The solid residue (29.0 g) was recrystallised directly from aqueous 2-propanol.
Yield: 16.2 g, 56%

2-(1,2,3,4-Tetrahydroisoquinolin-1-yl)acetic acid methyl ester 2-(1,2,3,4-Tetrahydroisoquinolin-1-yl)acetic acid (7.90 g, 41.3 mmol) was dissolved in methanol (200 ml), and $H_2SO_4$ (4.4 ml, 82.6 mmol) was added under a nitrogen atmosphere. The reaction solution was heated under reflux and, when the reaction was complete, was stirred overnight at room temperature. The methanol was removed in vacuo and the resulting residue was taken up in ethyl acetate (200 ml). The solution was washed with saturated $NaHCO_3$ solution (150 ml), dried (sodium sulfate) and concentrated.
Yield: 7.50 g (88%)

Methyl 2-(2-(3,4-dichlorophenylsulfonyl)-1,2,3,4-tetrahydroisoquinolin-1-yl)-acetate 2-(1,2,3,4-Tetrahydroisoquinolin-1-yl)acetic acid methyl ester (7.49 g, 36.5 mmol) was dissolved in DCM (200 ml), and triethylamine (11.7 ml, 83 mmol) was added thereto. The reaction solution was cooled to 0° C., and a solution of 3,4-dichlorobenzenesulfonyl chloride (8.14 g, 33.2 mmol) in DCM (100 ml) was added dropwise. After 3 h, 0.5 M HCl (100 ml) was added. After phase separation, the organic phase was washed with water, dried (sodium sulfate) and concentrated. Purification was carried out by column chromatography on silica gel (heptane/ethyl acetate 4:1).
Yield: 14.84 g 2-(2-(3,4-Dichlorophenylsulfonyl)-1,2,3,4-tetrahydroisoquinolin-1-yl)-acetic acid S1

To a mixture of methyl 2-(2-(3,4-dichlorophenylsulfonyl)-1,2,3,4-tetrahydroisoquinolin-1-yl)-acetate (14.84 g, 33.2 mmol), THF (200 ml) and water (120 ml) was a and stirred at room temperature. After 4 h, aqueous NaOH solution (6 M, 60 ml) was again added, and stirring was carried out overnight at room temperature. The reaction solution was concentrated under reduced pressure. 6 M HCl solution (125 ml) and DCM (400 ml) were added. After phase separation, the organic phase was washed with saturated NaCl solution, dried (sodium sulfate) and concentrated. For purification, the product was recrystallised from 2-propanol.
Yield: 11.30 g 2-(2-(3,4-Dichloro-N-methylphenylsulfonamido)phenyl)-acetic acid S2

Thionyl chloride (5.2 ml, 71.4 mmol) was added dropwise, with stirring and while cooling with ice, to a solution of 2-aminophenylacetic acid (7.2 g, 47.6 mmol) in methanol (150 ml). The reaction mixture was stirred overnight at room temperature. The reaction solution was concentrated, and thionyl chloride residues were removed by dragging out with toluene and DCM. 10.3 g (contaminated with starting material) of the were obtained in the form of a brown solid. The crude product was used further without being purified further.

2-(2-(3,4-Dichlorophenylsulfonamido)phenyl)acetic acid methyl ester

2-Aminophenylacetic acid methyl ester (10.2 g, 39.45 mmol) was dissolved in DCM (200 ml). There were then added first pyridine (12.4 ml, 151.71 mmol) and 3,4-dichlorobenzenesulfonyl chloride (11.8 ml, 75.87 mmol) in DCM (50 ml). The reaction solution was stirred overnight and then diluted with DCM and washed in succession with 0.5 M $KHSO_4$ solution, saturated $NaHCO_3$ solution and saturated NaCl solution, dried over sodium sulfate and concentrated. Purification was carried out by column chromatography on silica gel (DCM).
Yield: 14.3 g (96%)

2-(2-(3,4-Dichloro-N-methylphenylsulfonamido)phenyl)-acetic acid methyl ester 2-(2-(3,4-Dichlorophenylsulfonamido)phenyl)acetic acid methyl ester (14.3 g, 38.21 mmol) and methyl iodide (8.2 ml, 132.25 mmol) were dissolved in acetone (300 ml); $K_2CO_3$ (7.3 g, 52.90 mmol) was added thereto, and stirring was carried out overnight at 40° C. in a closed flask. The suspension was cooled and then filtered, concentrated, filtered over silica gel (eluant DCM) and concentrated.
Yield: 15.3 g

2-(2-(3,4-Dichloro-N-methylphenylsulfonamido)phenyl)-acetic acid S2

2-(2-(3,4-Dichloro-N-methylphenylsulfonamido)phenyl) acetic acid methyl ester (13.7 g, 34.26 mmol) was dissolved in a mixture of methanol/dioxane/4 M NaOH (15/4/1) (266 ml, 52.92 mmol NaOH), and then further 4 M NaOH (39.7 ml, 158.76 mmol) was added. The resulting clear solution was stirred overnight at room temperature and then concentrated in vacuo. The residue was taken up in ethyl acetate and washed with 0.5 M $KHSO_4$. The aqueous phase was then extracted several times with ethyl acetate. The combined organic phases were washed with saturated NaCl solution, dried over sodium sulfate and concentrated.
Yield: 13.0 g

Synthesis of 3-((3,4-dichloro-N-methylphenylsulfonamido)methyl)benzoic acid S3

3,4-Dichloro-N-methylbenzenesulfonamide

Methylamine hydrochloride (5.5 g, 81.46 mmol) was dissolved in DCM (300 ml), and $Et_3N$ (40 ml, 285.11 mmol) was added thereto. The reaction solution was then cooled to 0° C.; 3,4-dichlorobenzenesulfonyl chloride (20.00 g, 81.46 mmol) dissolved in DCM (50 ml) was then added dropwise, and stirring was carried out overnight at room temperature (TLC monitoring, silica gel, ethyl acetate). When the reaction was complete, 0.5 N HCl was added, the phases were separated, and the organic phase was washed with water and dried (sodium sulfate). The solvent was removed using a rotary evaporator. Purification was carried out by column chromatography on silica gel (gradient heptane/ethyl acetate 4:1 to 2:1).
Yield: 13.0 g (66%)

Methyl 3-((3,4-dichloro-N-methylphenylsulfonamido)methyl)-benzoate 3,4-Dichloro-N-methylbenzenesulfonamide (12.9 g, 53.72 mmol) was dissolved in acetone (200 ml), and $K_2CO_3$ (14.8 g, 107.44 mmol) was added thereto. Methyl (3-bromomethyl)benzoate (24.6 g, 107.44 mmol) was then added, and the suspension was heated overnight at 40° C. After cooling to room temperature, the solid material was filtered off and the filtrate was concentrated using a rotary evaporator. Purification was carried out by column chromatography on silica gel (heptane/ethyl acetate 4:1).
Yield: 19.9 g (95%)

3-((3,4-Dichloro-N-methylphenylsulfonamido)methyl)-benzoic acid S3

Methyl 3-((3,4-dichloro-N-methylphenylsulfonamido)methyl)benzoate (19.9 g, 51.25 mmol) was dissolved in a mixture of methanol/dioxane/4 M NaOH (15/4/1, 384 ml, 76.88 mmol NaOH, 1.5 eq.), and further 4 M NaOH (57.7 ml, 230.63 mmol, 4.5 eq.) was added thereto. After stirring overnight at room temperature, concentration was carried out using a rotary evaporator. Ethyl acetate (300 ml) was added to the residue, and washing with 0.5 M $KHSO_4$ was carried out. The aqueous phase was extracted again with ethyl acetate (200 ml). The combined organic phases were dried (sodium sulfate) and concentrated in vacuo.
Ethyl acetate was again added, and the suspension was filtered and concentrated.
Yield: 11.6 g (60%)

Synthesis of 2-(3,4-dichloro-N-methylphenylsulfonamido)benzoic acid S4

Methyl 2-(3,4-dichlorophenylsulfonamido)benzoate

Methyl 2-aminobenzoate (10 g, 66.2 mmol) was dissolved in DCM (100 ml), and pyridine (8.1 ml, 99.2 mmol, 1.5 eq.) was added thereto. A solution of 3,4-dichlorobenzenesulfonyl chloride (24.4 g, 99.2 mmol, 1.5 eq.) in DCM (150 ml) was then added dropwise at 0° C., and the reaction mixture was stirred overnight at room temperature. TLC monitoring (silica gel, DCM) showed complete conversion. When the reaction was complete, the reaction solution was diluted with DCM (250 ml) and washed with 0.5 M $KHSO_4$ (500 ml), saturated $NaHCO_3$ (500 ml) and saturated NaCl solution (500 ml). The organic phase was dried over sodium sulfate and concentrated in vacuo. For purification, filtration over a thin layer of silica gel was carried out (gradient: heptane/DCM (3:1) to DCM).
Yield: 21.9 g (91%)

Methyl 2-(3,4-dichloro-N-methylphenylsulfonamido)benzoate

Methyl 2-(3,4-dichlorophenylsulfonamido)benzoate (21.3 g, 59.1 mmol) was dissolved in acetone (300 ml), and $K_2CO_3$ (16.3 g, 118.3 mmol, 2 eq.) was added thereto. Methyl iodide (7.4 ml, 118.3 mmol, 2 eq.) was then added, and the suspension was heated overnight at 40° C. The solid materials were filtered off and the filtrate was concentrated using a rotary evaporator. Purification was carried out by filtration over silica gel (DCM).
Yield: 21.8 g (98%) The product was used further directly.

2-(3,4-Dichloro-N-methylphenylsulfonamido)benzoic acid S4

Methyl 2-(3,4-dichloro-N-methylphenylsulfonamido) benzoate (21.0 g, 56.1 mmol) was dissolved in a mixture of methanol/dioxane/4 M NaOH (15/4/1, 420 ml, 84 mmol NaOH, 1.5 eq.), and further 4 M NaOH (63 ml, 252 mmol, 4.5 eq.) was added. The solution was stirred overnight at room temperature and then concentrated using a rotary evaporator. Ethyl acetate (800 ml) was added to the residue, and the mixture was washed with 0.5 M KHSO$_4$ (1000 ml). The aqueous phase was then extracted three times with ethyl acetate (350 ml each time), and the combined organic phases were washed with saturated NaCl solution (500 ml). The organic phase was dried (sodium sulfate) and concentrated in vacuo.

The residue was washed with diisopropyl ether and dried overnight at 40° C. in a drying cabinet.

Yield: 18.83 g (90%)

Synthesis of 2-(3,4-dichloro-N-methylphenylsulfonamido)-4,5,6,7-tetrahydrobenzo[b]thiophene-3-carboxylic acid S5 tert-Butyl 2-amino-4,5,6,7-tetrahydrobenzo[b]thiophene-3-carboxylate

Morpholine (6.7 ml, 76 mmol) was added to a mixture of cyclohexanone (5.00 g, 50.9 mmol), tert-butyl cyanoacetate (7.91 g, 56.0 mmol) and sulfur (1.80 g, 56.0 mmol) in ethanol (abs., 150 ml). The reaction solution was stirred overnight at 50° C. and then cooled to room temperature. After filtration, the filtrate was concentrated and the residue was taken up in ethyl acetate (100 ml), washed with water (2×50 ml), saturated NaCl solution (2×50 ml), dried (sodium sulfate) and concentrated.

Purification was carried out by column chromatography on silica gel (heptane/ethyl acetate=10/1).

Yield: 12.73 g (99%)

tert-Butyl 2-(3,4-dichlorophenylsulfonamido)-4,5,6,7-tetrahydrobenzo[b]-thiophene-3-carboxylate tert-Butyl 2-amino-4,5,6,7-tetrahydrobenzo[b]thiophene-3-carboxylate (12.26 g, 48.4 mmol) was dissolved in DCM (150 ml), and pyridine (6.0 ml, 74 mmol) was added thereto. A solution of 3,4-dichlorobenzenesulfonyl chloride (8.4 ml, 54 mmol) was then added, and the mixture was heated for 17 h under reflux and then cooled to room temperature. Water was added (100 ml), and stirring was carried out overnight at room temperature. The phases were then separated (pH organic phase≈2), washed with saturated NaHCO$_3$ solution, dried (sodium sulfate) and concentrated in vacuo.

Yield: (21.64 g, 97%)

tert-Butyl 2-(3,4-dichloro-N-methylphenylsulfonamido)-4,5,6,7-tetrahydrobenzo-[b]thiophene-3-carboxylate tert-Butyl 2-(3,4-dichlorophenylsulfonamido)-4,5,6,7-tetrahydrobenzo[b]thiophene-3-carboxylate (21.64 g, 46.8 mmol) was dissolved in acetone (200 ml), and K$_2$CO$_3$ (12.9 g, 93.6 mmol) was added thereto. Methyl iodide (5.83 ml, 93.6 mmol) was then added, and the suspension was heated overnight at 40° C. After cooling to room temperature, water and saturated NaCl solution were added and the product was extracted with ethyl acetate. The organic phase was dried (sodium sulfate) and the product was purified by crystallization from methanol.

Yield: (16.47 g, 74%)

The mother liquor was concentrated and further product was obtained by crystallization from methanol.

Yield: 1.57 g, 7%
Overall yield: 18.04 g (81%)

2-(3,4-Dichloro-N-methylphenylsulfonamido)-4,5,6,7-tetrahydrobenzo[b]-thiophene-3-carboxylic acid S5

TFA (30 ml, 404 mmol) was added to a solution of tert-butyl 2-(3,4-dichloro-N-methylphenylsulfonamido)-4,5,6,7-tetrahydrobenzo[b]thiophene-3-carboxylate (8.00 g, 16.8 mmol) in DCM (100 ml), and stirring was carried out for 1 h at room temperature. The reaction mixture was concentrated, and the TFA that remained was removed with toluene, DCM and diethyl ether. The residue was washed twice with diisopropyl ether.

Yield: 6.49 g, 92%

Synthesis of 1-(3,4-dichlorophenylsulfonyl)indoline-2-carboxylic acid S6

Indoline-2-carboxylic acid methyl ester

Thionyl chloride (12.1 ml, 167.2 mmol) was added dropwise, with stirring and while cooling with ice, to a solution of indoline-2-carboxylic acid (24.8 g, 152.0 mmol) in methanol (500 ml). The reaction mixture was stirred overnight at 40° C. The reaction solution was concentrated and thionyl chloride residues were removed by dragging out with diethyl ether (3 times).

Yield: 33.5 g

Methyl 1-(3,4-dichlorophenylsulfonyl)indoline-2-carboxylate

Indoline-2-carboxylic acid methyl ester (33.0 g, 149.7 mmol) was dissolved in DCM (400 ml), and pyridine (37.8 ml, 463.2 mmol) was added thereto. A solution of 3,4-dichlorobenzenesulfonyl chloride (24.1 ml, 154.4 mmol) dissolved in DCM (100 ml) was then added, and the mixture was stirred overnight under reflux and then cooled to room temperature. The mixture was diluted with DCM and washed in succession with 0.5 M KHSO$_4$, saturated NaHCO$_3$ solution and saturated NaCl solution. The organic phase was dried (sodium sulfate) and concentrated in vacuo.

The residue was purified by column chromatography on silica gel (heptane/ethyl acetate=2:1).

Yield: 50.4 g (87%)

1-(3,4-Dichlorophenylsulfonyl)indoline-2-carboxylic acid S6

Methyl 1-(3,4-dichlorophenylsulfonyl)indoline-2-carboxylate (49.8 g, 128.92 mmol) was dissolved in a mixture of methanol/dioxane/4 M NaOH (15/4/1, 960 ml, 193.38 mmol NaOH, 1.5 eq.), and further 4 M NaOH (145 ml, 580.14 mmol, 4.5 eq.) was added thereto. The solution was stirred overnight at room temperature and then concentrated using a rotary evaporator. Ethyl acetate was added to the residue, and the mixture was washed with 0.5 M KHSO$_4$. The aqueous phase was then extracted three times with ethyl acetate, and the combined organic phases were washed with saturated NaCl solution (500 ml), dried (sodium sulfate) and concentrated in vacuo. The residue was washed with diethyl ether, filtered and dried.

Yield: 22.3 g (46%)

Synthesis of 1-(4-methoxyphenylsulfonyl)indoline-2-carboxylic acid S7

Methyl 1-(4-methoxyphenylsulfonyl)indoline-2-carboxylate

Indoline-2-carboxylic acid methyl ester (32.7 g, 151.8 mmol) was dissolved in DCM (400 ml), and pyridine (37.4 ml, 459.0 mmol) was added thereto. A solution of 4-methoxybenzenesulfonyl chloride (31.6 g, 153 mmol) dissolved in DCM (100 ml) was then added, and stirring was carried out overnight at room temperature. The mixture was diluted with DCM and washed in succession with 0.5 M $KHSO_4$, saturated $NaHCO_3$ solution and saturated NaCl solution. The organic phase was dried (sodium sulfate) and concentrated in vacuo. The residue was purified by column chromatography on silica gel (heptane/ethyl acetate 2:1).

Yield: 47.1 g (89%)

1-(4-Methoxyphenylsulfonyl)indoline-2-carboxylic acid S7

Methyl 1-(4-methoxyphenylsulfonyl)indoline-2-carboxylate (47.1 g, 135.6 mmol) was dissolved in a mixture of methanol/dioxane/4 M NaOH (15/4/1,1020 ml, 203.4 mmol NaOH, 1.5 eq.), and further 4 M NaOH (153 ml, 610.2 mmol, 4.5 eq.) was added thereto. The solution was stirred overnight at room temperature and then concentrated using a rotary evaporator. Ethyl acetate was added to the residue, and the mixture was washed with 0.5 M $KHSO_4$. The aqueous phase was extracted again with ethyl acetate, and the combined organic phases were washed with saturated NaCl solution, dried (sodium sulfate) and concentrated in vacuo. The residue was washed with diethyl ether, filtered and dried.

Yield: 38.1 g (84%)

Synthesis of 2-(1-(3-(trifluoromethyl)phenylsulfonyl)piperidin-2-yl)acetic acid S8

2-(Piperidin-2-yl)acetic acid

A solution of chromium trioxide (20 g, 200 mmol) in water (300 ml) and concentrated sulfuric acid (40 g, 73.6 ml) was added dropwise in the course of 1.5 h, while cooling with ice, to a solution of 2-piperidineethanol (10.0 g, 10.1 ml, 77.4 mmol) in water (10 ml). The reaction mixture was stirred for 3 h at room temperature. The solution was then rendered alkaline with saturated aqueous barium hydroxide solution. Carbon dioxide was then passed into the solution, and the resulting suspension was filtered through Celite. The filtrate was concentrated in vacuo.

Yield: 9.26 g (83%)

$^1$H-NMR ($D_2O$): 1.50-1.70 (m, 3H); 1.80-1.93 (m, 2H); 1.93-2.02 (m, 1H); 2.76 (d, 2H); 3.04 (dt, 1H); 3.38-3.45 (m, 1H); 3.45-3.57 (m, 1H).

2-(1-(3-(Trifluoromethyl)phenylsulfonyl)piperidin-2-yl)acetic acid S8

A solution of 3-trifluoromethylbenzenesulfonic acid chloride (2.70 g, 11 mmol) in 1,4-dioxane (10 ml) was added slowly, in the course of 1 h, to a solution of 2-(piperidin-2-yl)acetic acid (1.43 g, 10 mmol) in 1,4-dioxane (5 ml) and 1 N sodium hydroxide solution (22 ml). The mixture was then stirred for 4.5 h at room temperature, then acidified with 1 N hydrochloric acid and subsequently extracted with DCM (3×60 ml). The combined organic phases were dried over sodium sulfate and concentrated in vacuo.

Yield: 917 mg (26%)

$^1$H-NMR (DMSO-$d_6$): 1.05-1.55 (m, 6H); 2.25 (dd, 1H); 2.66 (dd, 1H); 2.99 (dt, 1H); 3.69 (br dd, 1H); 4.41 (1H, m); 7.87 (1H, t); 8.03-8.08 (m, 2H) 8.13 (d, 1H), 12.33 (br s, 1H).

Synthesis of 1-(4-methoxy-N-methylphenylsulfonamido)carboxylic acid S9

1-Amino-cyclohexanecarboxylic acid methyl ester hydrochloride

1-Amino-cyclohexanecarboxylic acid (49 g, 342 mmol) was added to a solution, cooled to 0° C., of thionyl chloride (49.6 ml, 684 mmol) in methanol (750 ml). The reaction mixture was stirred for 4 h under reflux and then overnight at room temperature. Then the mixture was heated again for 3 h under reflux and stirred overnight again at room temperature. The reaction solution was concentrated and the thionyl chloride residues were removed by dragging out with methanol and diethyl ether.

Yield: 66.64 g

Methyl 1-(4-methoxyphenylsulfonamido)-cyclohexanecarboxylate

1-Amino-cyclohexanecarboxylic acid methyl ester hydrochloride (32 g, 165 mmol) was suspended in DCM (1000 ml), and diisopropylethylamine (84.9 ml, 496 mmol) was added thereto. A solution of 4-methoxybenzenesulfonyl chloride (51.2 g, 248 mmol) dissolved in DCM (150 ml) was added dropwise at 0° C., and stirring was carried out overnight at room temperature. Aqueous 1 M HCl (150 ml) and water (50 ml) were added and the phases were separated. The organic phase was dried over sodium sulfate and concentrated to dryness. The product was purified by column chromatography on silica gel (DCM/methanol 99:1).

The mixed fractions were again purified by column chromatography on silica gel (gradient: DCM/heptane 5:1 to DCM/methanol 99:1).

Overall yield: 37.8 g (70%)

Methyl 1-(4-methoxy-N-methylphenylsulfonamido) cyclohexanecarboxylate

Methyl 1-(4-methoxyphenylsulfonamido)cyclohexanecarboxylate (27 g, 82.5 mmol) was dissolved in acetone (450 ml), and $K_2CO_3$ (22.8 g, 165 mmol) was added thereto. Methyl iodide (10.3 ml, 165 mmol) was then added, and the suspension was heated overnight at 40° C. in a closed flask. Because the reaction was not yet complete (TLC monitoring, heptane/ethyl acetate 2:1), methyl iodide (7.7 ml, 124 mmol) was again added and stirring was carried out over the weekend at room temperature. Methyl iodide (2.6 ml, 41.8 mmol) was again added, and stirring was carried out overnight at 40° C. After cooling, the solid materials were filtered off and the filtrate was concentrated to dryness. The crude product was used further without being purified further.

1-(4-Methoxy-N-methylphenylsulfonamido)carboxylic acid S9

Methyl 1-(4-methoxy-N-methylphenylsulfonamido)cyclohexanecarboxylate (28.2 g, 82.5 mmol) was dissolved in a mixture of methanol/dioxane/4 M NaOH (15/4/1, 620 ml, 124 mmol NaOH, 1.5 eq.), and further 4 M NaOH (93 ml, 372 mmol, 4.5 eq.) was added thereto. Because no reaction could be detected after stirring overnight at room temperature, the mixture was first heated for 8 h at 68° C., refluxed over the weekend at room temperature and again overnight. The mixture was then concentrated using a rotary evaporator. Ethyl acetate (500 ml) was added to the residue, and washing with 0.5 M KHSO$_4$ (500 ml) was carried out. The aqueous phase was extracted again with ethyl acetate (200 ml), dried (sodium sulfate) and concentrated in vacuo. The aqueous phase was acidified with HCl (2 M, 300 ml) and extracted three times with DCM (300 ml each time).

Overall yield: 26.5 g

Synthesis of 5-(2,4,6-trichloro-N-methylphenylsulfonamido)pentanoic acid S10

5-(2,4,6-Trichloro-phenylsulfonamido)pentanoic acid

A solution of 2,4,6-trichlorobenzenesulfonic acid chloride (3.00 g, 11 mmol) in 1,4-dioxane (50 ml) was added dropwise to a solution of 5-aminovaleric acid hydrochloride (1.50 g, 10 mmol) in 1 N sodium hydroxide solution (30 ml). The reaction mixture was stirred for 18 h at room temperature, and 1,4-dioxane was then distilled off in vacuo. The aqueous phase was extracted with ethyl acetate (3×50 ml) and then adjusted to pH 1 with concentrated hydrochloric acid. The acidic aqueous phase was extracted with ethyl acetate (3×60 ml). The combined organic phases were dried over sodium sulfate and concentrated in vacuo.

Yield: 2.28 g (64%)
$^1$H-NMR (DMSO-d$_6$): 1.33-1.57 (m, 4H); 2.12 (t, 2H); 2.87 (q, 2H); 4.00 (very br s, 1H); 7.85 (s, 1H); 8.22 (t, 1H).

Methyl 5-(2,4,6-trichloro-N-methylphenylsulfonamido)pentanoate

Cesium carbonate (449 mg, 1.38 mmol) and then methyl iodide (487 mg, 213 µl, 3.45 mmol) were added to a solution of 5-(2,4,6-trichlorophenylsulfon-amido)pentanoic acid (250 mg, 0.69 mmol) in a 1:1 mixture of N,N-dimethylformamide/acetone (10 ml), and stirring was carried out for 4 h at 50° C. The reaction mixture was then concentrated in vacuo; toluene was added repeatedly (3×) to the residue, concentration in vacuo was carried out again each time, and then the mixture was taken up in 5% sodium hydrogen carbonate solution and extracted with ethyl acetate (3×30 ml). The combined organic phases were dried over sodium sulfate and concentrated in vacuo.

Yield: 188 mg (69%)
$^1$H-NMR (DMSO-d$_6$): 1.40-1.60 (m, 4H); 2.30 (t, 2H); 2.82 (s, 3H); 3.32 (t, 2H); 3.57 (s, 3H); 7.89 (s, 2H).

5-(2,4,6-Trichloro-N-methylphenylsulfonamido) pentanoic acid S10

A solution of lithium hydroxide (18.2 mg, 0.76 mmol) in water (3 ml) was added to a solution of methyl 5-(2,4,6-trichloro-N-methylphenylsulfonamido)pentanoate (178 mg, 0.45 mmol) in THF (5 ml), and stirring was carried out for 18 h at room temperature. THF was then concentrated in vacuo, water was added to the residue, and extraction with DCM (2×20 ml) was carried out. The aqueous phase was adjusted to pH 1-2 with concentrated hydrochloric acid and extracted with ethyl acetate (3×20 ml). The combined organic extracts were dried over sodium sulfate and concentrated in vacuo.

Yield: 111 mg (64%)
$^1$H-NMR (DMSO-d$_6$): 1.40-1.58 (m, 4H); 2.21 (t, 2H); 2.83 (s, 3H); 3.24 (t, 2H); 7.89 (s, 2H); 12.0 (s, 1H).

Synthesis of 2-(1-(2,4-dichlorophenylsulfonyl)-3-oxopiperazin-2-yl)acetic acid S11

Ethyl 2-(3-oxopiperazin-2-yl)acetate

Ethylenediamine (1.17 ml, 17.42 mmol) and diethyl maleate (3 g, 17.42 mmol) were stirred for 16 h at 55° C. in propanol (30 ml). The solvent was removed in vacuo and the residue was dried in vacuo. The product was used in the next stage without being purified further.

Yield: 3.4 g (100%)

Ethyl 2-(1-(2,4-dichlorophenylsulfonyl)-3-oxopiperazin-2-yl)acetate

To a solution, cooled to 0° C., of the piperazine derivative (2.5 g, 13.4 mmol) in DCM (55 ml) and triethylamine (4.2 ml, 33.5 mmol) there was added dropwise at that temperature a 2,4-dichlorobenzenesulfonyl chloride (3 g, 13.4 mmol) in DCM (25 ml), and then a catalytic amount of DMAP was added thereto. The reaction solution was stirred for 16 h at room temperature and then diluted with DCM. The reaction mixture was washed first with 0.5 M HCl and then with water and saturated NaCl solution. The organic phase was dried over sodium sulfate and concentrated to dryness. The product was purified by column chromatography.

Yield: 2.85 g (58%)

2-(1-(2,4-Dichlorophenylsulfonyl)-3-oxopiperazin-2-yl)acetic acid S11

Lithium hydroxide (0.92 mg, 21.9 mmol) was added to a cooled solution of ethyl 2-(1-(2,4-dichlorophenylsulfonyl)-3-oxopiperazin-2-yl)acetate (2.7 g, 7.3 mmol) in methanol (25 ml) and water (6 ml), and stirring was carried out for 16 h at room temperature (TLC monitoring). The solvent was removed using a rotary evaporator and the residue was taken up in water. The aqueous phase was washed with diethyl ether and acidified with HCl, and the product was extracted with ethyl acetate. The organic phase was then washed with saturated NaCl solution. The organic phase was dried over sodium sulfate and concentrated to dryness.

Yield: 2.5 g (97%)

2-(1-(3,4-Dichlorophenylsulfonyl)-3-oxo-1,2,3,4-tetrahydroquinoxalin-2-yl)acetic acid S12

Methyl 2-(3-oxo-1,2,3,4-tetrahydroquinoxalin-2-yl)acetate

Orthophenylenediamine (10 g, 92.4 mmol) and diethyl maleate (45 g, 646.8 mmol) were refluxed for 75 h in propanol. The solvent was removed using a rotary evaporator and the residue was purified by column chromatography (ethyl acetate/hexane 1:1).

Yield: 4 g (18.5%)

Methyl 2-(1-(3,4-dichlorophenylsulfonyl)-3-oxo-1,2,3,4-tetrahydroquinoxalin-2-yl)acetate A solution of 3,4-dichlorobenzenesulfonyl chloride (4 ml, 25.6 mmol) in DCM (60 ml) was added dropwise to a solution (3 g, 12.8 mmol) in DCM (125 ml) and pyridine (5.17 ml, 64 mmol), and then a catalytic amount of DMAP was added thereto. The reaction solution was stirred for 16 h at room temperature and then diluted with DCM. The reaction mixture was washed with copper sulfate solution, 1 M HCl and sodium carbonate solution, water and saturated NaCl solution. The organic phase was dried over sodium sulfate and concentrated to dryness. The product was purified by column chromatography (ethyl acetate/hexane 4:6); yield: 3.12 g (55%).

2-(1-(3,4-Dichlorophenylsulfonyl)-3-oxo-1,2,3,4-tetrahydroquinoxalin-2-yl)acetic acid S12

Lithium hydroxide (0.041 g, 10.95 mmol) was added to a cooled solution of methyl 2-(1-(3,4-dichlorophenylsulfonyl)-3-oxo-1,2,3,4-tetrahydroquinoxalin-2-yl)acetate (2.7 g, 7.3 mmol) in THF (45 ml) and water (45 ml), and stirring was carried out for 48 h at room temperature (TLC monitoring). The solvent was removed using a rotary evaporator and the residue was taken up in water. The aqueous phase was extracted with ethyl acetate and then washed with saturated NaCl solution. The organic phase was dried over sodium sulfate and concentrated to dryness.
Yield: 0.6 g (23%)

2-(1-(3,4-Dichlorophenylsulfonyl)pyrrolidin-2-yl)acetic acid S13Pyrrolidin-2-ylacetic acid methyl ester Thionyl chloride (1.8 ml, 25.2 mmol) was added dropwise to a solution, cooled to 0° C., of pyrrolidin-2-ylacetic acid hydrochloride (1.4 g, 8.4 mmol) in methanol (35 ml), and the mixture was heated for 16 h at gentle boiling and then cooled to room temperature. The solvent was removed azeotropically in vacuo with benzene. Yield: 1.5 g (100%)

Methyl 2-(1-(3,4-dichlorophenylsulfonyl)pyrrolidin-2-yl)acetate

A solution of 3,4-dichlorobenzenesulfonyl chloride (1.88 g, 7.65 mmol) in DCM (15 ml) was added dropwise at 0° C. to a solution, cooled to 0° C., of pyrrolidin-2-ylacetic acid methyl ester (1.5 g, 8.4 mmol) in DCM (33 ml) and triethylamine was (2.66 ml, 21 mmol), and stirring was then carried out for 90 minutes at room temperature. 0.5 M HCl (20 ml) was then added, and stirring was carried out for a further 15 minutes. The organic phase was separated, washed with water and dried over sodium sulfate. The solvent was removed using a rotary evaporator and the product was used in the next stage without being purified further. Yield: 2.1 g (77%)

2-(1-(3,4-Dichlorophenylsulfonyl)pyrrolidin-2-yl)acetic acid S13

Lithium hydroxide (0.75 mg, 18 mmol) was added to a cooled solution of methyl 2-(1-(3,4-dichlorophenylsulfonyl)pyrrolidin-2-yl)acetate (2.1 g, 6 mmol) in methanol (20 ml) and water (20 ml), and stirring was carried out for 16 h at room temperature (TLC monitoring). The solvent was removed using a rotary evaporator and the residue was taken up in water. The aqueous phase was washed with ethyl acetate and acidified with 1 M HCl, and then the product was extracted with ethyl acetate and the organic phase was washed with saturated NaCl solution. The organic phase was dried over sodium sulfate and concentrated to dryness. Yield: 2.0 g (99%)

2-(1-(3,4-Dichlorophenylsulfonyl)piperidin-2-yl)acetic acid S14

Piperidin-2-ylacetic acid methyl ester hydrochloride

Thionyl chloride (1.8 ml, 25.2 mmol) was added dropwise to a solution, cooled to 0° C., of piperidin-2-ylacetic acid hydrochloride (1.5 g, 8.4 mmol) in methanol (35 ml), and the mixture was heated for 16 h at gentle boiling and then cooled to room temperature. The solvent was removed azeotropically in vacuo with benzene. Yield: 1.3 g (100%)

Methyl 2-(1-(3,4-dichlorophenylsulfonyl)piperidin-2-yl)acetate

A solution of 3,4-dichlorobenzenesulfonyl chloride (1.88 g, 7.65 mmol) in DCM (15 ml) was added at 0° C. to a solution, cooled to 0° C., of piperidin-2-ylacetic acid methyl ester hydrochloride (1.3 g, 8.4 mmol) in DCM (33 ml) and triethylamine (2.66 ml, 21 mmol), and stirring was then carried out for 90 minutes at room temperature. 0.5 M HCl (20 ml) was then added, and stirring was carried out for a further 15 minutes. The organic phase was separated off, washed with water and dried over sodium sulfate. The solvent was removed using a rotary evaporator and the product was used in the next stage without being purified further. Yield: 1.9 g (63%)

2-(1-(3,4-Dichlorophenylsulfonyl)piperidin-2-yl)acetic acid S14

Lithium hydroxide (0.75 mg, 18 mmol) was added to a cooled solution of methyl 2-(1-(3,4-dichlorophenylsulfonyl)piperidin-2-yl)acetate (2.1 g, 6 mmol) in methanol (20 ml) and water (20 ml), and stirring was carried out for 16 h at room temperature (TLC monitoring). The solvent was removed using a rotary evaporator and the residue was taken up in water. The aqueous phase was washed with ethyl acetate and then acidified with 1 M HCl, and the product was extracted with ethyl acetate, and the organic phase was then washed with saturated NaCl solution. The organic phase was dried over sodium sulfate and concentrated to dryness. Yield: 2.9 g (98%)

2-(2-(4-Methoxyphenylsulfonyl)-1,2,3,4-tetrahydroisoquinolin-1-yl)acetic acid S15

Methyl 2-(2-(4-methoxyphenylsulfonyl)-1,2,3,4-tetrahydroisoquinolin-1-yl)-acetate 2-(1,2,3,4-Tetrahydroisoquinolin-1-yl)acetic acid methyl ester (9.55 g, 46.5 mmol) was dissolved in DCM (150 ml), and triethylamine (14.9 ml, 106 mmol) was added thereto. The reaction mixture was cooled to 0° C., and a solution of methoxybenzenesulfonyl chloride (8.74 g, 42.3 mmol) in DCM (100 ml) was added dropwise thereto. The reaction mixture was stirred overnight at room temperature. For working up, 100 ml of a 0.5 M HCl solution were added and then the phases were separated. The organic phase was first washed with water and then dried over sodium sulfate. The crude product was purified by column chromatography on silica gel (mobile phase: DCM).
Yield: 15.22 g (96%)

2-(2-(4-Methoxyphenylsulfonyl)-1,2,3,4-tetrahydroisoquinolin-1-yl)acetic acid S15

A 6 M aqueous NaOH solution was added to a mixture of methyl 2-(2-(4-methoxyphenylsulfonyl)-1,2,3,4-tetrahydroisoquinolin-1-yl)acetate (15.22 g, 40.54 mmol) in THF (200 ml) and water (120 ml), and stirring was carried out overnight at room temperature. The solvent was then removed under reduced pressure, and a 6 M aqueous HCl solution (125 ml) and DCM (400 ml) were added. The phases were separated and then the organic phase was washed with concentrated NaCl solution, dried over sodium sulfate and concentrated. Yield: 14.65 g (100%)

3-(Naphthalene-2-sulfonamido)-3-phenylpropionic acid S16

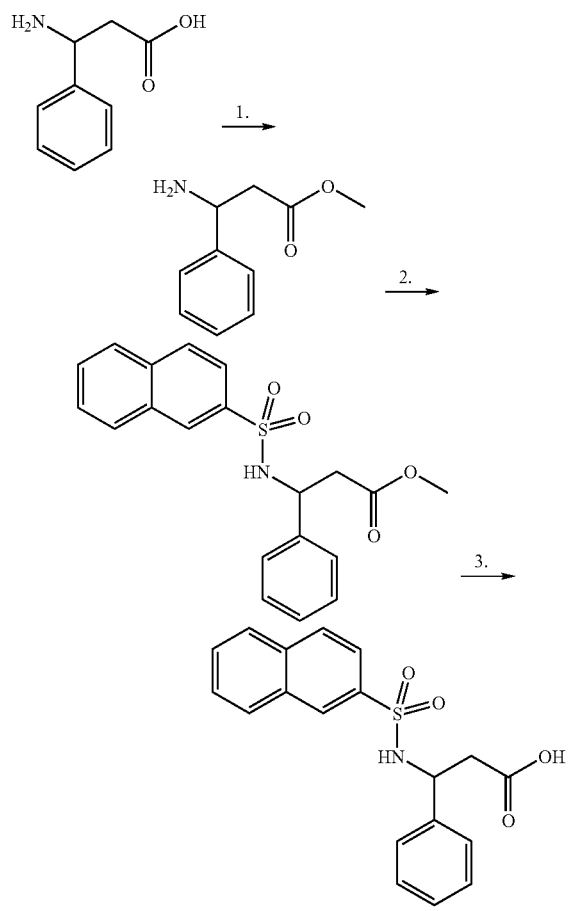

Stage 1. Thionyl chloride (19.1 g, 162 mmol) was added dropwise to a solution, cooled to 0° C., of 3-amino-3-phenylpropionic acid (8.9 g, 54 mmol) in methanol (150 ml). The reaction mixture was then heated for 12 h under reflux (TLC monitoring). The solvent was removed completely and the residue was dried in vacuo. The crude product was used in the next stage without being purified further.

Stage 2. The amino alcohol (1.1 eq.) was dissolved in DCM (4 ml/mmol), and triethylamine (2.2 eq.) was added thereto. The solution was cooled to 0° C., a solution of the corresponding sulfonic acid chloride (1 eq.) dissolved in DCM (2.3 ml/mmol) was added dropwise, and stirring was carried out for 1.5 h at RT. When the reaction was complete, HCl (0.5 M, 2.3 ml/mmol) was added and the phases were separated, washed with water, dried over $Na_2SO_4$ and concentrated. The crude product was purified by column chromatography (silica gel, ethyl acetate/hexane, 3:7).

Stage 3. $LiOH.H_2O$ (2 eq.) was added at a reaction temperature of 0° C. to a solution of the ester (1 eq.) in a methanol/water mixture (3:1, 10 ml/mmol). The reaction mixture was stirred for 16 h at RT. The solvent was removed under reduced pressure and the residue was taken up in water and washed with DCM. The aqueous phase was then carefully acidified with HCl (1 N) and extracted with ethyl acetate. The organic phase was washed with water and sat. NaCl solution and dried over $Na_2SO_4$. After removal of the solvent, the product was obtained in adequate purity.

3-(1-(4-Chloro-2,5-dimethylphenylsulfonyl)piperidin-2-yl)propionic acid S17

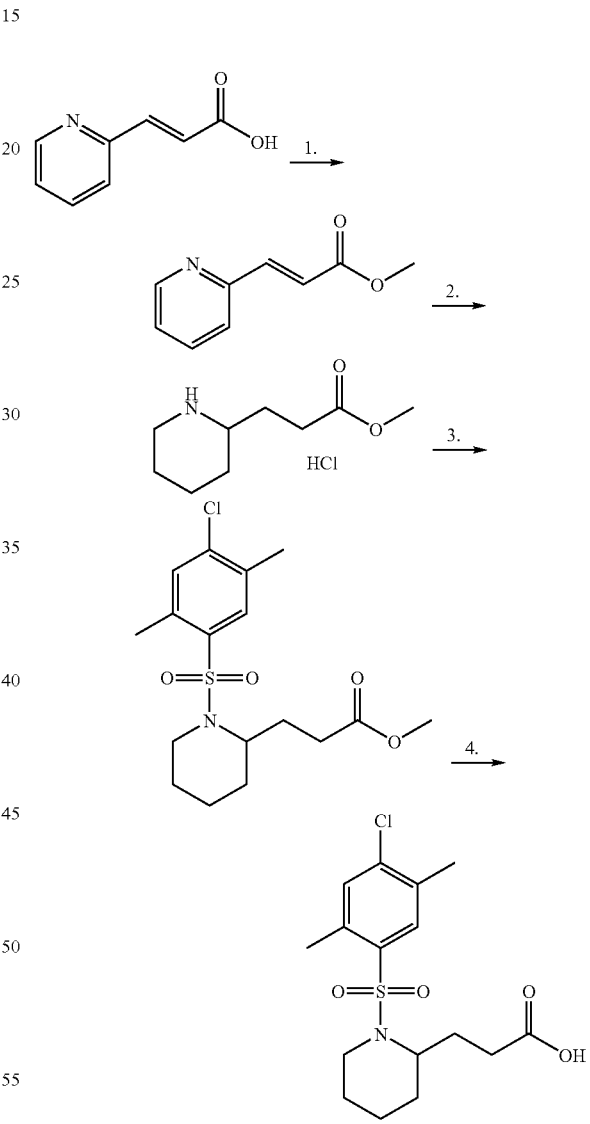

Stage 1. $H_2SO_4$ (12.8 ml, 240 mmol) was added to a solution of 3-(2-pyridyl)-acrylic acid (23.88 g, 160 mmol) in methanol (750 ml). The reaction mixture was heated overnight under reflux and, after cooling to RT, was poured into saturated aqueous $NaHCO_3$ solution (1000 ml). The methanol was removed using a rotary evaporator, and the aqueous phase was extracted twice with ethyl acetate (400 ml). The organic phase was washed with saturated NaCl solution (500 ml), dried over $Na_2SO_4$ and concentrated. The crude product of methyl 3-(pyridin-2-yl)acrylate was used in the next stage without being purified further.

Stage 2. Methyl 3-(pyridin-2-yl)acrylate (22.15 g, 136 mmol) was dissolved in THF (300 ml) and chloroform (10.9 ml), and $PtO_2$ (3.08 g, 13.6 mmol, 0.1 eq.) was added under a nitrogen atmosphere. The solution was first rinsed for 10 min. with nitrogen and then stirred overnight under a $H_2$ atmosphere (8 bar). After cooling, rinsing with nitrogen was first carried out again, the catalyst was removed by filtration over filtering earth and then rinsed with DCM, and the filtrate was concentrated to dryness in vacuo. The methyl 3-(piperidin-2-yl)propionate hydrochloride was used in the next stage without being purified further.

Stage 3. The amino alcohol (1.1 eq.) was dissolved in DCM (4 ml/mmol), and triethylamine (2.2 eq.) was added thereto. The solution was cooled to 0° C., a solution of the corresponding sulfonic acid chloride (1 eq.) dissolved in DCM (2.3 ml/mmol) was added dropwise, and stirring was carried out for 1.5 h at RT. When the reaction was complete, HCl (0.5 M, 2.3 ml/mmol) was added and the phases were separated, washed with water, dried over $Na_2SO_4$ and concentrated. The crude product was purified by column chromatography on silica gel (silica gel, hexane/ethyl acetate, 6:1→3:1).

Stage 4. Aqueous NaOH solution (6 M, 3 ml/mmol) was added to a solution of the ester (1 eq.) in THF (3 ml/mmol). After a reaction time of 1 h, the solvent was removed using a rotary evaporator and cooling to 0° C. was carried out. HCl (6 M, 3 ml/mmol) was added and extraction with ethyl acetate was carried out. The organic phase was dried over $Na_2SO_4$ and concentrated.

Synthesis of the carbamates

Synthesis of phenyl 3-(4-methoxy-N,2,3,6-tetramethylphenylsulfonamido)-propylcarbamate V1

N—(2-Cyanoethyl)-4-methoxy-N,2,3,6-tetramethylbenzenesulfonamide

4-Methoxy-2,3,6-trimethylbenzenesulfonyl chloride (5.00 g, 20 mmol) was added at room temperature to a solution of 3-methylaminopropionitrile (1.50 g, 18.3 mmol) and triethylamine (5.50 g, 55 mmol) in THF (30 ml), and stirring was carried out for 16 h. Ethyl acetate (50 ml) was then added to the reaction mixture, and washing with sodium hydrogen carbonate solution (3×50 ml) was carried out. The organic phase was dried over sodium sulfate and concentrated in vacuo.

Yield: 4.92 g (91%)
$^1$H-NMR (DMSO-$d_6$): 2.09 (s, 3H); 2.44 (s, 3H); 2.59 (s, 3H); 2.68 (s, 3H); 2.76 (t, 2H); 3.30 (t, 2H); 3.84 (s, 3H); 6.87 (s, 1H).

N-(3-Aminopropyl)-4-methoxy-N,2,3,6-tetramethylbenzenesulfonamide

Platinum(IV) oxide (400 mg) was added to a solution of N—(2-cyanoethyl)-4-methoxy-2,3,6—N-tetramethylbenzenesulfonamide (4.92 g, 16.6 mmol) and concentrated sulfuric acid (3.20 g, 33.2 mmol) in ethanol (100 ml), and stirring was carried out for 3 h at room temperature under a hydrogen atmosphere of 3 bar. Sodium hydrogen carbonate was then added to the solution, and the mixture was filtered and concentrated in vacuo. The residue was taken up in sodium hydrogen carbonate solution (50 ml) and extracted with DCM (3×50 ml). The combined organic phases were dried over sodium sulfate and concentrated in vacuo.

Yield: 4.65 g (93%)
$^1$H-NMR (DMSO-$d_6$): 1.53 (td, 2H); 2.09 (s, 3H); 2.43 (s, 3H); 2.50 (m, 2H); 2.58 (s, 3H); 2.61 (s, 3H); 3.06 (t, 2H); 3.21 (br s, 2H); 3.84 (s, 3H); 6.84 (s, 1H).

Phenyl 3-(4-methoxy-N,2,3,6-tetramethylphenylsulfonamido)-propylcarbamate V1

Chloroformic acid phenyl ester (2.29 g, 14.6 mmol) was added at room temperature to a solution of N—(3-aminopropyl)-4-methoxy-2,3,6—N-tetramethyl-benzenesulfonamide (3.99 g, 13.3 mmol) and triethylamine (4.0 g, 5.5 ml, 40 mmol) in THF (60 ml), and stirring was carried out for 16 h at that temperature. Saturated sodium hydrogen carbonate solution (30 ml) was then added to the solution, and extraction with ethyl acetate (2×30 ml) was carried out. The combined organic phases were dried over sodium sulfate and concentrated in vacuo, and the residue was purified by flash chromatography with cyclohexane/ethyl acetate (3:1).

Yield: 4.62 g (83%)
$^1$H-NMR (DMSO-$d_6$): 1.71 (td, 2H); 2.09 (s, 3H); 2.44 (s, 3H); 2.59 (s, 3H); 2.65 (s, 3H); 2.99 (dd, 2H); 3.08 (t, 2H); 3.83 (s, 3H); 6.85 (s, 1H); 7.06 (d, 2H); 7.19 (t, 1H); 7.37 (t, 2H); 7.70 (t, 1H).

The following ureas were prepared:

N—(3-{3-[4-(Dimethylaminophenylmethyl)cyclohexyl]ureido}propyl)-4-methoxy-2,3,6,N-tetramethylbenzenesulfonamide Example 1

A solution of 4-((dimethylamino)(phenyl)methyl)cyclohexanamine A1 (439 mg, 1.89 mmol) and phenyl 3-(4-methoxy-N,2,3,6-tetramethylphenylsulfonamido)-propylcarbamate V1 (794 mg, 1.89 mmol) in 1,4-dioxane (10 ml) was stirred for 1 d at 110° C. The solvent was then removed in vacuo and the residue was purified by flash chromatography with chloroform/methanol/triethylamine (100:5:1).

Yield: 700 mg (66%) 2 isomers
$^1$H-NMR (DMSO-$d_6$): 0.94 (m, 5H); 1.33 (m, 2H); 1.55 (m, 2H); 1.67 (d, 1H); 1.81 (d, 1H); 1.99 (s, 6H); 2.08 (s, 3H); 2.41 (s, 3H); 2.56 (s, 3H); 2.60 (s, 3H); 2.89 (m, 2H); 3.00 (m, 2H); 3.22 (d, 1H); 3.59 (m, 1H); 3.83 (s, 3H); 5.62 (m, 0.5H); 5.69 (m, 0.5H); 5.78 (d, 1H); 6.82 (s, 1H); 7.13 (d, 2H); 7.26 (dd, 1H); 7.33 (dt, 2H).

(N—(3-(3-((4-((dimethylamino)(phenyl)methyl) cyclohexyl)methyl)ureido)propyl)-4-methoxy-N,2,3, 6-tetramethylbenzenesulfonamide Example 2

A solution of 1-(4-(aminomethyl)cyclohexyl)-N,N-dimethyl-1-phenylmethanamine A12 (200 mg, 0.81 mmol) and phenyl 3-(4-methoxy-N,2,3,6-tetramethylphenylsulfonamido)-propylcarbamate V1 (366 mg, 0.81 mmol) in 1,4-dioxane (10 ml) was stirred for 1 d at 110° C. The solvent was then removed in vacuo and the residue was purified by flash chromatography with chloroform/methanol/triethylamine (100:5:1).

Yield: 351 mg (76%)
$^1$H-NMR (DMSO-$d_6$): 0.78 (m, 4H); 1.17 (t, 2H); 1.36 (d, 1H); 1.56 (td, 3H); 1.70 (d, 1H); 1.84 (d, 1H); 1.99 (s, 6H); 2.08 (s, 3H); 2.41 (s, 3H); 2.56 (s, 3H); 2.59 (s, 3H); 2.78 (t, 2H); 2.90 (dd, 2H); 3.02 (m, 2H); 3.37 (d, 1H); 3.83 (s, 3H); 5.70 (t, 1H); 5.78 (d, 1H); 6.82 (s, 1H); 7.13 (t, 2H); 7.24 (m, 1H); 7.31 (m, 2H).

4-Methoxy-2,3,6,N-tetramethyl-N—(3-{3-[4-(phenylpyrrolidin-1-ylmethyl)-cyclohexyl]-ureido}propyl)benzenesulfonamide

Example 3

A solution of 4-(phenyl(pyrrolidin-1-yl)methyl)cyclohexanamine A9 (268 mg, 1.03 mmol) and phenyl 3-(4-methoxy-N,2,3,6-tetramethylphenylsulfonamido) -propylcarbamate V1 (469 mg, 1.03 mmol) in 1,4-dioxane (10 ml) was stirred for 1 d at 110° C. The solvent was then removed in vacuo and the residue was purified by flash chromatography with chloroform/methanol/triethylamine (100:2:1→100:5:1).
Yield: 210 mg (35%)
$^1$H-NMR (DMSO-$d_6$): 0.61 (dd, 1H); 0.78 (m, 1H); 1.02 (m, 3H) 1.56 (m, 7H); 1.73 (d, 4H); 2.08 (s, 3H); 2.33 (m, 4H); 2.40 (s, 3H); 2.56 (s, 3H); 2.59 (s, 3H); 2.86 (dd, 2H); 2.99 (m, 2H); 3.09 (d, 1H); 3.83 (s, 3H); 5.59 (t, 1H); 5.64 (t, 1H); 6.81 (s, 1H); 7.16-7.19 (m, 2H); 7.22-7.25 (m, 1H); 7.29-7.31 (m, 2H).

4-(Dimethylaminophenylmethyl)piperidin-1-carboxylic acid {3-[(4-methoxy-2,3,6-trimethylbenzenesulfonyl)methylamino]propyl}amide

Example 4

A solution of N,N-dimethyl-1-phenyl-1-(piperidin-4-yl)methanamine A28 (300 mg, 1.37 mmol) and phenyl 3-(4-methoxy-N,2,3,6-tetramethylphenylsulfonamido)-propylcarbamate V1 (621 mg, 1.37 mmol) in 1,4-dioxane (10 ml) was stirred for 1 d at 110° C. The solvent was then removed in vacuo and the residue was purified by flash chromatography with chloroform/methanol/triethylamine (100:5:1). Yield: 425 mg (57%)
$^1$H-NMR (DMSO-$d_6$): 0.77 (ddd, 2H); 0.91 (ddd, 2H); 1.20 (d, 1H); 1.58 (m, 2H); 1.88 (d, 1H); 2.01 (s, 6H); 2.08 (s, 3H); 2.41 (s, 3H); 2.56 (s, 3H); 2.61 (s, 3H); 2.63 (d, 1H); 2.90 (dd, 2H); 2.97 (m, 2H); 3.08 (d, 1H); 3.75 (d, 1H); 3.83 (s, 3H); 3.89 (d, 1H); 6.24 (t, 1H); 6.82 (s, 1H); 7.14 (d, 2H); 7.25 (t, 1H); 7.33 (t, 2H).

Amides

The following examples were prepared in individual syntheses.

N—(4-((Dimethylamino)(phenyl)methyl)cyclohexyl)-5-(2,4,6-trichloro-N-methylphenylsulfonamido)pentanamide

Example 5

A solution of 5-(2,4,6-trichloro-N-methylphenylsulfonamido)pentanoic acid S10 (250 mg, 0.667 mmol), N-methylmorpholine (201 mg, 218 µl, 2.0 mmol) and 1-benzotriazolyloxy-tris(dimethylamino)phosphonium hexafluorophosphate (381 mg, 0.867 mmol) in anhydrous N,N-dimethylformamide (10 ml) was stirred for one hour, and then a solution of 4-((dimethylamino)(phenyl)methyl) cyclohexanamine A1 (174 mg, 1.0 mmol) was added thereto, and stirring was carried out for 18 h at room temperature. The reaction mixture was then concentrated in vacuo, and the residue was taken up in water and adjusted to pH 8 with 5% sodium hydrogen carbonate solution. The mixture was extracted with ethyl acetate (3×40 ml), and the combined organic phases were dried over sodium sulfate and concentrated in vacuo. The crude product was purified by flash chromatography with chloroform/methanol (95:5).
Yield: 122 mg (31%), yellowish oil
$^1$H-NMR (CDCl$_3$): 1.40-2.18 (m, 14H); 2.08 and 2.10 (2 s, 6H); 2.87 and 2.88 (2 s, 3H); 3.02 (d, 0.35); 3.22-3.35 (m, 3.65H); 3.94-4.04 (m, 1H); 5.58 (d, 0.35H); 5.80 (d, 0.65H); 7.06-7.14 (m, 2H); 7.20-7.35 (m, 3H); 7.45 and 7.46 (2 s, 2H).

N—(4-(Phenyl(piperidin-1-yl)methyl)cyclohexyl)-5-(2,4,6-trichloro-N-methylphenylsulfonamido)pentanamide

Example 6

A solution of 5-(2,4,6-trichloro-N-methylphenylsulfonamido)pentanoic acid S10 (374 mg, 1.0 mmol), N-methylmorpholine (302 mg, 328 µl, 2.9 mmol) and 1-benzotriazolyloxy-tris(dimethylamino)phosphonium hexafluorophosphate (571 mg, 1.3 mmol) in anhydrous N,N-dimethylformamide (10 ml) was stirred for one hour, and then a solution of 4-(phenyl (piperidin-1-yl)methyl)cyclohexanamine A10 (302 mg, 1.11 mmol) in anhydrous N,N-dimethylformamide (5 ml) was added thereto and stirring was carried out for 18 h at room temperature. The reaction mixture was then concentrated in vacuo, and the residue was taken up in water and adjusted to pH 8 with 5% sodium hydrogen carbonate solution. The mixture was extracted with ethyl acetate (3×40 ml), and the combined organic phases were dried over sodium sulfate and concentrated in vacuo. The crude product was purified by flash chromatography with chloroform/methanol (95:5).
Yield: 128 mg (21%)
$^1$H-NMR (DMSO-$d_6$): 1.00-2.30 (m, 26H); 2.84 (m, 3H); 3.19-3.26 (m, 2H); 3.74 (br s, 1H); 7.09-7.15 (m, 2H); 7.25 (d, 0.5H); 7.28-7.36 (m, 3H); 7.55 (d, 0.5H); 7.86 and 7.88 (2 s, 2H).

N—((4-((Dimethylamino)(phenyl)methyl)cyclohexyl)methyl)-5-(2,4,6-trichloro-N-methylphenylsulfonamido)pentanamide

Example 7

N,N'-Carbonyldiimidazole (248 mg, 1.45 mmol) was added to a solution of 5-(2,4,6-trichloro-N-methylphenylsulfonamido)pentanoic acid S10 (495 mg, 1.32 mmol) in anhydrous THF (10 ml), and stirring was carried out for 1 h at room temperature. A solution of 1-(4-(aminomethyl)cyclohexyl)-N,N-dimethyl-1-phenylmethanamine A12 (357 mg, 1.45 mmol) in anhydrous THF (10 ml) was then added. The reaction mixture was stirred for 18 h at room temperature and then concentrated in vacuo; 5% sodium hydrogen carbonate solution (50 ml) was added to the residue, and extraction with ethyl acetate (3×50 ml) was carried out. The combined organic phases were dried over sodium sulfate and concentrated in vacuo. The crude product was purified by flash chromatography with chloroform/methanol (9:1).
Yield: 638 mg (80%)
$^1$H-NMR (DMSO-$d_6$): 0.60-1.95 (m, 13H); 1.99 (s, 6H); 2.05 (t, 2H); 2.82 (s, 3H), 2.85-2.99 (m, 2H); 3.00 (d, 1H); 3.21 (t, 2H); 7.15-7.40 (m, 5H); 7.68 (t, 1H), 7.85 (s, 2H).

N—((4-((Dimethylamino)(phenyl)methyl)cyclohexyl)methyl)-2-(1-(3-(trifluoromethyl)phenylsulfonyl)piperidin-2-yl)acetamide

Example 8

N,N'-Carbonyldiimidazole (188 mg, 1.1 mmol) was added to a solution of 2-(1-(3-(trifluoromethyl)phenylsulfonyl)piperidin-2-yl)acetic acid S8 (351 mg, 1 mmol) in anhydrous THF (10 ml), and stirring was carried out for 1 h at room temperature. A solution of 1-(4-(aminomethyl)cyclohexyl-N,N-dimethyl-1-phenylmethanamine A12 (271 mg, 1.1 mmol) in anhydrous THF (10 ml) was then added to the mixture, and stirring was carried out for 18 h at room temperature. The reaction mixture was concentrated in vacuo, 5% sodium hydrogen carbonate solution was added to the residue, and extraction with ethyl acetate (3×30 ml) was carried out. The combined organic phases were dried over sodium sulfate and concentrated in vacuo. The crude product was purified by flash chromatography with chloroform/methanol (9:1).

Yield: 298 mg (51%)

$^1$H-NMR (DMSO-d$_6$): 0.50-1.90 (m, 16H); 1.98 (s, 6H); 2.19 (dd, 1H), 2.43 (dd, 1H); 2.65-2.85 (m, 1.5H); 2.85-3.10 (m, 1.5H); 3.68 (br d, 1H); 4.43 (m, 1H); 7.05-7.38 (m, 5H); 7.70-7.88 (m, 2H); 7.95-8.20 (m, 2H).

Automated Synthesis

Method A

On an Accelerator SLT106 from Chemspeed, 105 μmol of CDI solution (0.105 M in DCM, 1 ml) were first introduced at room temperature into the reactors, the appropriate acid solution (0.05 M in DCM, 2 ml) was added, and the whole was agitated for 1 h at room temperature. 100 μmol of the appropriate amine (0.1 M in DCM, 1 ml) were then added at room temperature, and the whole was agitated for a further 12 h at RT.

When the reaction was complete, 3 ml of water were added, the whole was agitated for 15 min, and then the organic phase was separated. The solvent was removed in a Genevac vacuum centrifuge and the products were purified by means of HPLC.

Method B

Using the installation from Zymark, 100 μmol of acid solution (0.05 M in DCM, 2 ml) were placed in a dry screw-cap jar at RT, and 105 μmol of CDI solution (0.105 M in DCM, 1 ml) were added thereto. After a stirring time of 1 hour at RT, 100 μmol of the appropriate amine (0.1 M in DCM) were added to the reaction solution by means of a pipette. The reaction solution was stirred for 16 h at RT. Then 3 ml of water were added and thorough mixing was carried out for 30 min. The magnetic stirrer bar was filtered off and the vessel was rinsed with 1.5 ml of DCM.

The aqueous phase was removed and discarded. 3 ml of dist. H$_2$O and 0.5 ml of DCM were added to the organic phase, and the mixture was vortexed and mixed thoroughly and intensively. After centrifugation, the aqueous phase was separated off and discarded. The organic phase was extracted a second time in an analogous manner with 3 ml of sat. NaCl solution. Then the organic phase was removed, placed in a test tube and dried over a MgSO$_4$ cartridge. The solution was concentrated in a vacuum centrifuge (GeneVac), and the products were purified by means of HPLC.

Method C

In parallel synthesis, the acid structural unit (50 mg, 1 eq.) was dissolved in DCM (3 ml/mmol), and the amine structural unit (1.2 eq.), EDCI (1.5 eq.), HOBt (1 eq.) and DIPEA (2 eq.) were added thereto. The resulting crude products were purified using a parallel purification system from Biotage.

The following compounds were synthesised by these methods. The target mass was confirmed in all cases as M+1 by mass spectroscopy:

| No. | Amine | Acid | Method | Mass + 1 | Name |
|---|---|---|---|---|---|
| 9 | A1 | S15 | A | 576.3 | N-[4-(Dimethylamino-phenyl-methyl)-cyclohexyl]-2-[2-(4-methoxy-benzenesulfonyl)-1,2,3,4-tetrahydro-isoquinolin-1-yl]-acetamide |
| 10 | A1 | S1 | A | 614.2 | 2-[2-(3,4-Dichloro-benzenesulfonyl)-1,2,3,4-tetrahydro-isoquinolin-1-yl]-N-[4-(dimethylamino-phenyl-methyl)-cyclohexyl]-acetamide |
| 11 | A1 | S3 | A | 574.2 | 2-[(3,4-Dichloro-benzenesulfonyl)-methyl-amino]-N-[4-(dimethylamino-phenyl-methyl)-cyclohexyl]-benzamide |
| 12 | A1 | S6 | A | 634.2 | 2-[(3,4-Dichloro-benzenesulfonyl)-methyl-amino]-4,5,6,7-tetrahydro-benzo[b]thiophene-3-carboxylic acid [4-(dimethylamino-phenyl-methyl)-cyclohexyl]-amide |
| 13 | A3 | S15 | A | 594.3 | N-{4-[Dimethylamino-(3-fluoro-phenyl)-methyl]-cyclohexyl}-2-[2-(4-methoxy-benzenesulfonyl)-1,2,3,4-tetrahydro-isoquinolin-1-yl]-acetamide |
| 14 | A2 | S15 | A | 594.3 | N-{4-[Dimethylamino-(4-fluoro-phenyl)-methyl]-cyclohexyl}-2-[2-(4-methoxy-benzenesulfonyl)-1,2,3,4-tetrahydro-isoquinolin-1-yl]-acetamide |
| 15 | A4 | S15 | A | 582.2 | N-[4-(Dimethylamino-thiophen-2-yl-methyl)-cyclohexyl]-2-[2-(4-methoxy-benzenesulfonyl)-1,2,3,4-tetrahydro-isoquinolin-1-yl]-acetamide |
| 16 | A14 | S15 | A | 608.3 | N-{4-[Dimethylamino-(3-fluoro-phenyl)-methyl]-cyclohexylmethyl}-2-[2-(4-methoxy-benzene-sulfonyl)-1,2,3,4-tetrahydro-isoquinolin-1-yl]-acetamide |
| 17 | A12 | S15 | A | 590.3 | N-[4-(Dimethylamino-phenyl-methyl)-cyclohexyl-methyl]-2-[2-(4-methoxy-benzenesulfonyl)-1,2,3,4-tetrahydro-isoquinolin-1-yl]-acetamide |
| 18 | A17 | S15 | A | 618.3 | N-[4-(1-Dimethylamino-3-phenyl-propyl)-cyclohexyl-methyl]-2-[2-(4-methoxy-benzenesulfonyl)-1,2,3,4-tetrahydro-isoquinolin-1-yl]-acetamide |
| 19 | A13 | S15 | A | 608.3 | N-{4-[Dimethylamino-(4-fluoro-phenyl)-methyl]-cyclohexylmethyl}-2-[2-(4-methoxy-benzene-sulfonyl)-1,2,3,4-tetrahydro-isoquinolin-1-yl]-acetamide |
| 20 | A15 | S15 | A | 624.3 | N-{4-[(4-Chloro-phenyl)-dimethylamino-methyl]-cyclohexylmethyl}-2-[2-(4-methoxy-benzene-sulfonyl)-1,2,3,4-tetrahydro-isoquinolin-1-yl]-acetamide |

-continued

| No. | Amine | Acid | Method | Mass + 1 | Name |
|---|---|---|---|---|---|
| 21 | A16 | S15 | A | 596.3 | N-[4-(Dimethylamino-thiophen-2-yl-methyl)-cyclohexylmethyl]-2-[2-(4-methoxy-benzenesulfonyl)-1,2,3,4-tetrahydro-isoquinolin-1-yl]-acetamide |
| 22 | A25 | S15 | A | 638.3 | N-(2-{4-[(4-Chloro-phenyl)-dimethylamino-methyl]-cyclohexyl}-ethyl)-2-[2-(4-methoxy-benzenesulfonyl)-1,2,3,4-tetrahydro-isoquinolin-1-yl]-acetamide |
| 23 | A24 | S15 | A | 622.3 | N-(2-{4-[Dimethylamino-(3-fluoro-phenyl)-methyl]-cyclohexyl}-ethyl)-2-[2-(4-methoxy-benzenesulfonyl)-1,2,3,4-tetrahydro-isoquinolin-1-yl]-acetamide |
| 24 | A23 | S15 | A | 622.3 | N-(2-{4-[Dimethylamino-(4-fluoro-phenyl)-methyl]-cyclohexyl}-ethyl)-2-[2-(4-methoxy-benzenesulfonyl)-1,2,3,4-tetrahydro-isoquinolin-1-yl]-acetamide |
| 25 | A26 | S15 | A | 610.3 | N-{2-[4-(Dimethylamino-thiophen-2-yl-methyl)-cyclohexyl]-ethyl}-2-[2-(4-methoxy-benzenesulfonyl)-1,2,3,4-tetrahydro-isoquinolin-1-yl]-acetamide |
| 26 | A3 | S1 | A | 632.2 | 2-(2-(3,4-Dichlorophenylsulfonyl)-1,2,3,4-tetrahydroisoquinolin-1-yl)-N-(4-((dimethylamino)(3-fluorophenyl)methyl)cyclohexyl)acetamide |
| 27 | A2 | S1 | A | 632.2 | 2-(2-(3,4-Dichlorophenylsulfonyl)-1,2,3,4-tetrahydroisoquinolin-1-yl)-N-(4-((dimethylamino)(4-fluorophenyl)methyl)cyclohexyl)acetamide |
| 28 | A14 | S1 | A | 646.2 | 2-[2-(3,4-Dichloro-benzenesulfonyl)-1,2,3,4-tetrahydro-isoquinolin-1-yl]-N-{4-[dimethylamino-(3-fluoro-phenyl)-methyl]-cyclohexylmethyl}-acetamide |
| 29 | A12 | S1 | A | 628.2 | 2-[2-(3,4-Dichloro-benzenesulfonyl)-1,2,3,4-tetrahydro-isoquinolin-1-yl]-N-[4-(dimethylamino-phenyl-methyl)-cyclohexylmethyl]-acetamide |
| 30 | A17 | S1 | A | 656.2 | 2-[2-(3,4-Dichloro-benzenesulfonyl)-1,2,3,4-tetrahydro-isoquinolin-1-yl]-N-[4-(1-dimethylamino-3-phenyl-propyl)-cyclohexylmethyl]-acetamide |
| 31 | A13 | S1 | A | 646.2 | 2-[2-(3,4-Dichloro-benzenesulfonyl)-1,2,3,4-tetrahydro-isoquinolin-1-yl]-N-{4-[dimethylamino-(4-fluoro-phenyl)-methyl]-cyclohexylmethyl}-acetamide |
| 32 | A15 | S1 | A | 662.2 | N-{4-[(4-Chloro-phenyl)-dimethylamino-methyl]-cyclohexylmethyl}-2-[2-(3,4-dichloro-benzene-sulfonyl)-1,2,3,4-tetrahydro-isoquinolin-1-yl]-acetamide |
| 33 | A25 | S1 | A | 676.2 | N-(2-{4-[(4-Chloro-phenyl)-dimethylamino-methyl]-cyclohexyl}-ethyl)-2-[2-(3,4-dichloro-benzene-sulfonyl)-1,2,3,4-tetrahydro-isoquinolin-1-yl]-acetamide |
| 34 | A24 | S1 | A | 660.2 | 2-[2-(3,4-Dichloro-benzenesulfonyl)-1,2,3,4-tetrahydro-isoquinolin-1-yl]-N-(2-{4-[dimethylamino-(3-fluoro-phenyl)-methyl]-cyclohexyl}-ethyl)-acetamide |
| 35 | A23 | S1 | A | 660.2 | 2-[2-(3,4-Dichloro-benzenesulfonyl)-1,2,3,4-tetrahydro-isoquinolin-1-yl]-N-(2-{4-[dimethylamino-(4-fluoro-phenyl)-methyl]-cyclohexyl}-ethyl)-acetamide |
| 36 | A3 | S4 | A | 592.2 | 2-[(3,4-Dichloro-benzenesulfonyl)-methyl-amino]-N-{4-[dimethylamino-(3-fluoro-phenyl)-methyl]-cyclohexyl}-benzamide |
| 37 | A2 | S4 | A | 592.2 | 2-[(3,4-Dichloro-benzenesulfonyl)-methyl-amino]-N-{4-[dimethylamino-(4-fluoro-phenyl)-methyl]-cyclohexyl}-benzamide |
| 38 | A12 | S4 | A | 588.2 | 2-[(3,4-Dichloro-benzenesulfonyl)-methyl-amino]-N-[4-(dimethylamino-phenyl-methyl)-cyclohexylmethyl]-benzamide |
| 39 | A17 | S4 | A | 616.2 | 2-[(3,4-Dichloro-benzenesulfonyl)-methyl-amino]-N-[4-(1-dimethylamino-3-phenyl-propyl)-cyclohexyl-methyl]-benzamide |
| 40 | A13 | S4 | A | 606.2 | 2-[(3,4-Dichloro-benzenesulfonyl)-methyl-amino]-N-{4-[dimethylamino-(4-fluoro-phenyl)-methyl]-cyclohexylmethyl}-benzamide |
| 41 | A15 | S4 | A | 622.1 | N-{4-[(4-Chloro-phenyl)-dimethylamino-methyl]-cyclohexylmethyl}-2-[(3,4-dichloro-benzenesulfonyl)-methyl-amino]-benzamide |
| 42 | A16 | S4 | A | 594.1 | 2-[(3,4-Dichloro-benzenesulfonyl)-methyl-amino]-N-[4-(dimethylamino-thiophen-2-yl-methyl)-cyclohexyl-methyl]-benzamide |
| 43 | A25 | S4 | A | 636.2 | N-(2-{4-[(4-Chloro-phenyl)-dimethylamino-methyl]-cyclohexyl}-ethyl)-2-[(3,4-dichloro-benzenesulfonyl)-methyl-amino]-benzamide |
| 44 | A24 | S4 | A | 620.2 | 2-[(3,4-Dichloro-benzenesulfonyl)-methyl-amino]-N-(2-{4-[dimethylamino-(3-fluoro-phenyl)-methyl]-cyclohexyl}-ethyl)-benzamide |

| No. | Amine | Acid | Method | Mass + 1 | Name |
|---|---|---|---|---|---|
| 45 | A23 | S4 | A | 620.2 | 2-[(3,4-Dichloro-benzenesulfonyl)-methyl-amino]-N-(2-{4-[dimethylamino-(4-fluoro-phenyl)-methyl]-cyclohexyl}-ethyl)-benzamide |
| 46 | A12 | S5 | A | 648.2 | 2-[(3,4-Dichloro-benzenesulfonyl)-methyl-amino]-4,5,6,7-tetrahydro-benzo[b]thiophene-3-carboxylic acid [4-(dimethylamino-phenyl-methyl)-cyclohexyl-methyl]-amide |
| 47 | A13 | S5 | A | 666.2 | 2-[(3,4-Dichloro-benzenesulfonyl)-methyl-amino]-4,5,6,7-tetrahydro-benzo[b]thiophene-3-carboxylic acid {4-[dimethylamino-(4-fluoro-phenyl)-methyl]-cyclohexylmethyl}-amide |
| 48 | A15 | S5 | A | 682.1 | 2-[(3,4-Dichloro-benzenesulfonyl)-methyl-amino]-4,5,6,7-tetrahydro-benzo[b]thiophene-3-carboxylic acid {4-[(4-chloro-phenyl)-dimethylamino-methyl]-cyclohexylmethyl}-amide |
| 49 | A16 | S5 | A | 654.1 | 2-[(3,4-Dichloro-benzenesulfonyl)-methyl-amino]-4,5,6,7-tetrahydro-benzo[b]thiophene-3-carboxylic acid [4-(dimethylamino-thiophen-2-yl-methyl)-cyclohexylmethyl]-amide |
| 50 | A25 | S5 | A | 696.2 | N-(2-(4-((4-Chlorophenyl)(dimethylamino)methyl)-cyclohexyl)ethyl)-2-(3,4-dichloro-N-methylphenyl-sulfonamido)-4,5,6,7-tetrahydrobenzo[b]thiophene-3-carboxamide |
| 51 | A24 | S5 | A | 680.2 | 2-(3,4-Dichloro-N-methylphenylsulfonamido)-N-(2-(4-((dimethylamino)(3-fluorophenyl)methyl)cyclohexyl)-ethyl)-4,5,6,7-tetrahydrobenzo[b]thiophene-3-carboxamide |
| 52 | A23 | S5 | A | 680.2 | 2-(3,4-Dichloro-N-methylphenylsulfonamido)-N-(2-(4-((dimethylamino)(4-fluorophenyl)methyl)cyclohexyl)-ethyl)-4,5,6,7-tetrahydrobenzo[b]thiophene-3-carboxamide |
| 53 | A26 | S5 | A | 668.2 | 2-(3,4-Dichloro-N-methylphenylsulfonamido)-N-(2-(4-((dimethylamino)(thiophen-2-yl)methyl)cyclohexyl)-ethyl)-4,5,6,7-tetrahydrobenzo[b]thiophene-3-carboxamide |
| 54 | A11 | S12 | C | 671.2 | 2-[1-(3,4-Dichloro-benzenesulfonyl)-3-oxo-1,2,3,4-tetrahydro-quinoxalin-2-yl]-N-[4-(morpholin-4-yl-phenyl-methyl)-cyclohexyl]-acetamide |
| 55 | A18 | S11 | C | 637.2 | 2-[1-(2,4-Dichloro-benzenesulfonyl)-3-oxo-piperazin-2-yl]-N-[4-(morpholin-4-yl-phenyl-methyl)-cyclohexyl-methyl]-acetamide |
| 56 | A19 | S11 | C | 665.2 | 2-[1-(2,4-Dichloro-benzenesulfonyl)-3-oxo-piperazin-2-yl]-N-[4-(1-morpholin-4-yl-3-phenyl-propyl)-cyclohexylmethyl]-acetamide |
| 57 | A21 | S11 | C | 649.2 | 2-[1-(2,4-Dichloro-benzenesulfonyl)-3-oxo-piperazin-2-yl]-N-[4-(3-phenyl-1-pyrrolidin-1-yl-propyl)-cyclohexylmethyl]-acetamide |
| 58 | A20 | S11 | C | 621.2 | 2-[1-(2,4-Dichloro-benzenesulfonyl)-3-oxo-piperazin-2-yl]-N-[4-(phenyl-pyrrolidin-1-yl-methyl)-cyclohexyl-methyl]-acetamide |
| 59 | A7 | S11 | C | 649.2 | 2-[1-(2,4-Dichloro-benzenesulfonyl)-3-oxo-piperazin-2-yl]-N-[4-(3-phenyl-1-piperidin-1-yl-propyl)-cyclo-hexyl]-acetamide |
| 60 | A6 | S11 | C | 651.2 | 2-[1-(2,4-Dichloro-benzenesulfonyl)-3-oxo-piperazin-2-yl]-N-[4-(1-morpholin-4-yl-3-phenyl-propyl)-cyclohexyl]-acetamide |
| 61 | A8 | S11 | C | 636.2 | 2-[1-(2,4-Dichloro-benzenesulfonyl)-3-oxo-piperazin-2-yl]-N-{4-[(4-methyl-piperazin-1-yl)-phenyl-methyl]-cyclohexyl}-acetamide |
| 62 | A29 | S11 | C | 609.2 | 4-(2,4-Dichloro-benzenesulfonyl)-3-{2-[4-(morpholin-4-yl-phenyl-methyl)-piperidin-1-yl]-2-oxo-ethyl}-piperazin-2-one |
| 63 | A30 | S11 | C | 623.2 | 4-(2,4-Dichlorophenylsulfonyl)-3-(2-(2-(1-morpholino-2-phenylethyl)piperidin-1-yl)-2-oxoethyl)piperazin-2-one |
| 64 | A18 | S12 | C | 685.2 | 2-[1-(3,4-Dichloro-benzenesulfonyl)-3-oxo-1,2,3,4-tetrahydro-quinoxalin-2-yl]-N-[4-(morpholin-4-yl-phenyl-methyl)-cyclohexylmethyl]-acetamide |
| 65 | A19 | S12 | C | 713.2 | 2-[1-(3,4-Dichloro-benzenesulfonyl)-3-oxo-1,2,3,4-tetrahydro-quinoxalin-2-yl]-N-[4-(1-morpholin-4-yl-3-phenyl-propyl)-cyclohexylmethyl]-acetamide |
| 66 | A21 | S12 | C | 697.2 | 2-[1-(3,4-Dichloro-benzenesulfonyl)-3-oxo-1,2,3,4-tetrahydro-quinoxalin-2-yl]-N-[4-(3-phenyl-1-pyrrolidin-1-yl-propyl)-cyclohexylmethyl]-acetamide |
| 67 | A20 | S12 | C | 669.2 | 2-[1-(3,4-Dichloro-benzenesulfonyl)-3-oxo-1,2,3,4-tetrahydro-quinoxalin-2-yl]-N-[4-(phenyl-pyrrolidin-1-yl-methyl)-cyclohexylmethyl]-acetamide |

-continued

| No. | Amine | Acid | Method | Mass + 1 | Name |
|---|---|---|---|---|---|
| 68 | A7 | S12 | C | 697.2 | 2-[1-(3,4-Dichloro-benzenesulfonyl)-3-oxo-1,2,3,4-tetrahydro-quinoxalin-2-yl]-N-[4-(3-phenyl-1-piperidin-1-yl-propyl)-cyclohexyl]-acetamide |
| 69 | A6 | S12 | C | 699.2 | 2-[1-(3,4-Dichloro-benzenesulfonyl)-3-oxo-1,2,3,4-tetrahydro-quinoxalin-2-yl]-N-[4-(1-morpholin-4-yl-3-phenyl-propyl)-cyclohexyl]-acetamide |
| 70 | A8 | S12 | C | 684.2 | 2-[1-(3,4-Dichloro-benzenesulfonyl)-3-oxo-1,2,3,4-tetrahydro-quinoxalin-2-yl]-N-{4-[(4-methyl-piperazin-1-yl)-phenyl-methyl]-cyclohexyl}-acetamide |
| 71 | A29 | S12 | C | 657.2 | 4-(3,4-Dichloro-benzenesulfonyl)-3-{2-[4-(morpholin-4-yl-phenyl-methyl)-piperidin-1-yl]-2-oxo-ethyl}-3,4-dihydro-1H-quinoxalin-2-one |
| 72 | A30 | S12 | C | 671.2 | 4-(3,4-Dichlorophenylsulfonyl)-3-(2-(4-(1-morpholino-2-phenylethyl)piperidin-1-yl)-2-oxoethyl)-3,4-dihydroquinoxalin-2(1H)-one |
| 73 | A18 | S13 | C | 608.2 | 2-[1-(3,4-Dichloro-benzenesulfonyl)-pyrrolidin-2-yl]-N-[4-(morpholin-4-yl-phenyl-methyl)-cyclohexyl-methyl]-acetamide |
| 74 | A19 | S13 | C | 636.2 | 2-[1-(3,4-Dichloro-benzenesulfonyl)-pyrrolidin-2-yl]-N-[4-(1-morpholin-4-yl-3-phenyl-propyl)-cyclohexyl-methyl]-acetamide |
| 75 | A21 | S13 | C | 620.2 | 2-[1-(3,4-Dichloro-benzenesulfonyl)-pyrrolidin-2-yl]-N-[4-(3-phenyl-1-pyrrolidin-1-yl-propyl)-cyclohexyl-methyl]-acetamide |
| 76 | A20 | S13 | C | 592.2 | 2-[1-(3,4-Dichloro-benzenesulfonyl)-pyrrolidin-2-yl]-N-[4-(phenyl-pyrrolidin-1-yl-methyl)-cyclohexyl-methyl]-acetamide |
| 77 | A7 | S13 | C | 620.2 | 2-(1-(3,4-Dichlorophenylsulfonyl)pyrrolidin-2-yl)-N-(4-(3-phenyl-1-(piperidin-1-yl)propyl)cyclohexyl)-acetamide |
| 78 | A6 | S13 | C | 622.2 | 2-(1-(3,4-Dichlorophenylsulfonyl)pyrrolidin-2-yl)-N-(4-(1-morpholino-3-phenylpropyl)cyclohexyl)acetamide |
| 79 | A8 | S13 | C | 607.2 | 2-[1-(3,4-Dichloro-benzenesulfonyl)-pyrrolidin-2-yl]-N-{4-[(4-methyl-piperazin-1-yl)-phenyl-methyl]-cyclohexyl}-acetamide |
| 80 | A29 | S13 | C | 580.2 | 2-[1-(3,4-Dichloro-benzenesulfonyl)-pyrrolidin-2-yl]-1-[4-(morpholin-4-yl-phenyl-methyl)-piperidin-1-yl]-ethanone |
| 81 | A30 | S13 | C | 594.2 | 2-(1-(3,4-Dichlorophenylsulfonyl)pyrrolidin-2-yl)-1-(4-(1-morpholino-2-phenylethyl)piperidin-1-yl)ethanone |
| 82 | A18 | S14 | C | 622.2 | 2-[1-(3,4-Dichloro-benzenesulfonyl)-piperidin-2-yl]-N-[4-(morpholin-4-yl-phenyl-methyl)-cyclohexylmethyl]-acetamide |
| 83 | A19 | S14 | C | 650.3 | 2-[1-(3,4-Dichloro-benzenesulfonyl)-piperidin-2-yl]-N-[4-(1-morpholin-4-yl-3-phenyl-propyl)-cyclohexyl-methyl]-acetamide |
| 84 | A21 | S14 | C | 634.3 | 2-[1-(3,4-Dichloro-benzenesulfonyl)-piperidin-2-yl]-N-[4-(3-phenyl-1-pyrrolidin-1-yl-propyl)-cyclohexyl-methyl]-acetamide |
| 85 | A20 | S14 | C | 606.2 | 2-[1-(3,4-Dichloro-benzenesulfonyl)-piperidin-2-yl]-N-[4-(phenyl-pyrrolidin-1-yl-methyl)-cyclohexylmethyl]-acetamide |
| 86 | A7 | S14 | C | 634.3 | 2-[1-(3,4-Dichloro-benzenesulfonyl)-piperidin-2-yl]-N-[4-(3-phenyl-1-piperidin-1-yl-propyl)-cyclohexyl]-acetamide |
| 87 | A6 | S14 | C | 636.2 | 2-[1-(3,4-Dichloro-benzenesulfonyl)-piperidin-2-yl]-N-[4-(1-morpholin-4-yl-3-phenyl-propyl)-cyclohexyl]-acetamide |
| 88 | A8 | S14 | C | 621.2 | 2-[1-(3,4-Dichloro-benzenesulfonyl)-piperidin-2-yl]-N-{4-[(4-methyl-piperazin-1-yl)-phenyl-methyl]-cyclohexyl}-acetamide |
| 89 | A29 | S14 | C | 594.2 | 2-[1-(3,4-Dichloro-benzenesulfonyl)-piperidin-2-yl]-1-[4-(morpholin-4-yl-phenyl-methyl)-piperidin-1-yl]-ethanone |
| 90 | A30 | S14 | C | 608.2 | 2-(1-(3,4-Dichlorophenylsulfonyl)piperidin-2-yl)-1-(4-(1-morpholino-2-phenylethyl)piperidin-1-yl)ethanone |
| 91 | A1 | S6 | B | 586.2 | 1-(3,4-Dichlorophenylsulfonyl)-N-(4-((dimethyl-amino)(phenyl)methyl)cyclohexyl)indoline-2-carboxamide |
| 92 | A3 | S6 | B | 604.2 | 1-(3,4-Dichlorophenylsulfonyl)-N-(4-((dimethyl-amino)(3-fluorophenyl)methyl)cyclohexyl)indoline-2-carboxamide |
| 93 | A5 | S6 | B | 614.2 | 1-(3,4-Dichlorophenylsulfonyl)-N-(4-(1-(dimethyl-amino)-3-phenylpropyl)cyclohexyl)indoline-2-carboxamide |
| 94 | A2 | S6 | B | 604.2 | 1-(3,4-Dichlorophenylsulfonyl)-N-(4-((dimethyl-amino)(4-fluorophenyl)methyl)cyclohexyl)indoline-2-carboxamide |

-continued

| No. | Amine | Acid | Method | Mass + 1 | Name |
|---|---|---|---|---|---|
| 95 | A12 | S6 | B | 600.2 | 1-(3,4-Dichlorophenylsulfonyl)-N-((4-((dimethyl-amino)(phenyl)methyl)cyclohexyl)methyl)indoline-2-carboxamide |
| 96 | A17 | S6 | B | 628.2 | 1-(3,4-Dichlorophenylsulfonyl)-N-((4-(1-(dimethyl-amino)-3-phenylpropyl)cyclohexyl)methyl)indoline-2-carboxamide |
| 97 | A27 | S6 | B | 642.2 | 1(3,4-Dichlorophenylsulfonyl)-N-(2-(4-(1-(dimethyl-amino)-3-phenylpropyl)cyclohexyl)ethyl)indoline-2-carboxamide |
| 98 | A22 | S2 | B | 616.2 | 2-(2-(3,4-Dichloro-N-methylphenylsulfonamido)-phenyl)-N-(2-(4-((dimethylamino)(phenyl)-methyl)cyclohexyl)ethyl)acetamide |
| 99 | A27 | S2 | B | 644.2 | 2-(2-(3,4-Dichloro-N-methylphenylsulfonamido)-phenyl)-N-(2-(4-(1-(dimethylamino)-3-phenylpropyl)-cyclohexyl)ethyl)acetamide |
| 100 | A22 | S9 | B | 570.3 | N-(2-(4-((Dimethylamino)(phenyl)methyl)cyclohexyl)-ethyl)-1-(4-methoxy-N-methylphenylsulfonamido)-cyclohexanecarboxamide |
| 101 | A11 | S11 | C | 623.2 | 2-(1-(2,4-Dichlorophenylsulfonyl)-3-oxopiperazin-2-yl)-N-(4-(morpholino(phenyl)methyl)cyclohexyl)-acetamide |
| 102 | A9 | S11 | C | 607.2 | 2-(1-(2,4-Dichlorophenylsulfonyl)-3-oxopiperazin-2-yl)-N-(4-(phenyl(pyrrolidin-1-yl)methyl)cyclohexyl)-acetamide |
| 103 | A9 | S12 | C | 655.2 | 2-(1-(3,4-Dichlorophenylsulfonyl)-3-oxo-1,2,3,4-tetrahydroquinoxalin-2-yl)-N-(4-(phenyl(pyrrolidin-1-yl)methyl)cyclohexyl)acetamide |
| 104 | A11 | S13 | C | 594.2 | 2-(1-(3,4-Dichlorophenylsulfonyl)pyrrolidin-2-yl)-N-(4-(morpholino(phenyl)methyl)cyclohexyl)acetamide |
| 105 | A9 | S13 | C | 578.2 | 2-(1-(3,4-Dichlorophenylsulfonyl)pyrrolidin-2-yl)-N-(4-(phenyl(pyrrolidin-1-yl)methyl)cyclohexyl)acetamide |
| 106 | A11 | S14 | C | 608.2 | 2-(1-(3,4-Dichlorophenylsulfonyl)piperidin-2-yl)-N-(4-(morpholino(phenyl)methyl)cyclohexyl)acetamide |
| 107 | A9 | S14 | C | 592.2 | 2-(1-(3,4-Dichlorophenylsulfonyl)piperidin-2-yl)-N-(4-(phenyl(pyrrolidin-1-yl)methyl)cyclohexyl)acetamide |
| 108 | A33 | S8 | C | 607.3 | 1-(4-((4-Methylpiperazin-1-yl)(phenyl)methyl)-piperidin-1-yl)-2-(1-(3-(trifluoromethyl)-phenyl-sulfonyl)piperidin-2-yl)ethanone |
| 109 | A32 | S8 | C | 625.3 | 1-(4-((4-Fluorophenyl)(4-methylpiperazin-1-yl)methyl)piperidin-1-yl)-2-(1-(3-(trifluoromethyl)-phenylsulfonyl)piperidin-2-yl)ethanone |
| 110 | A31 | S16 | C | 629.3 | N-(3-(4-((3-Fluorophenyl)(4-methylpiperazin-1-yl)methyl)piperidin-1-yl)-3-oxo-1-phenylpropyl)-naphthalene-2-sulfonamide |
| 111 | A34 | S8 | C | 621.3 | 1-(4-(1-(4-Methylpiperazin-1-yl)-2-phenylethyl)-piperidin-1-yl)-2-(1-(3-(trifluoromethyl)phenyl-sulfonyl)piperidin-2-yl)ethanone |
| 112 | A35 | S8 | C | 621.3 | 1-(4-(1-(4-Methylpiperazin-1-yl)-3-phenylpropyl)-piperidin-1-yl)-2-(1-(3-(trifluoromethyl)phenyl-sulfonyl)piperidin-2-yl)ethanone |
| 113 | A35 | S16 | C | 635.3 | N-(3-(4-(1-(4-Methylpiperazin-1-yl)-3-phenylpropyl)-piperidin-1-yl)-3-oxo-1-phenylpropyl)naphthalene-2-sulfonamide |
| 114 | A33 | S16 | C | 639.3 | N-(3-(4-((4-Methylpiperazin-1-yl)(phenyl)methyl)-piperidin-1-yl)-3-oxo-1-phenylpropyl)naphthalene-2-sulfonamide |
| 115 | A31 | S8 | C | 611.3 | 1-(4-((3-Fluorophenyl)(4-methylpiperazin-1-yl)-methyl)piperidin-1-yl)-2-(1-(3-(trifluoromethyl)-phenylsulfonyl)piperidin-2-yl)ethanone |
| 116 | A34 | S16 | C | 625.3 | N-(3-(4-(1-(4-Methylpiperazin-1-yl)-2-phenylethyl)-piperidin-1-yl)-3-oxo-1-phenylpropyl)naphthalene-2-sulfonamide |
| 117 | A32 | S16 | C | 626.3 | N-(3-(4-((4-Fluorophenyl)(4-methylpiperazin-1-yl)-methyl)piperidin-1-yl)-3-oxo-1-phenylpropyl)-naphthalene-2-sulfonamide |
| 118 | A34 | S17 | C | 629.3 | 3-(1-(4-Chloro-2,5-dimethylphenylsulfonyl)piperidin-2-yl)-1-(4-(1-(4-methylpiperazin-1-yl)-2-phenylethyl)-piperidin-1-yl)propan-1-one |
| 119 | A35 | S17 | C | 630.3 | 3-(1-(4-Chloro-2,5-dimethylphenylsulfonyl)piperidin-2-yl)-1-(4-(1-(4-methylpiperazin-1-yl)-3-phenylpropyl)piperidin-1-yl)propan-1-one |
| 120 | A31 | S17 | C | 643.3 | 3-(1-(4-Chloro-2,5-dimethylphenylsulfonyl)piperidin-2-yl)-1-(4-((3-fluorophenyl)(4-methylpiperazin-1-yl)methyl)piperidin-1-yl)propan-1-one |
| 121 | A32 | S17 | C | 633.3 | 3-(1-(4-Chloro-2,5-dimethylphenylsulfonyl)piperidin-2-yl)-1-(4-((4-fluorophenyl)(4-methylpiperazin-1-yl)methyl)piperidin-1-yl)propan-1-one |

-continued

| No. | Amine | Acid | Method | Mass + 1 | Name |
|---|---|---|---|---|---|
| 122 | A33 | S17 | C | 633.3 | 3-(1-(4-Chloro-2,5-dimethylphenylsulfonyl)piperidin-2-yl)-1-(4-((4-methylpiperazin-1-yl)(phenyl)methyl)-piperidin-1-yl)propan-1-one |

Studies of the Effectiveness of the Compounds According to the Invention

Method for determining the affinity for the human µ-opiate receptor

The receptor affinity for the human µ-opiate receptor is determined in a homogeneous batch on microtitre plates. To this end, serial dilutions of the substances to be tested are incubated for 90 minutes at room temperature with a receptor membrane preparation (15-40 µg of protein/250 µl of incubation batch) of CHO-K1 cells, which express the human µ-opiate receptor (RB-HOM receptor membrane preparation from PerkinElmer Life Sciences, Zaventem, Belgium), in the presence of 1 nmol/l of the radioactive ligand [$^3$H]-naloxone (NET719, PerkinElmer Life Sciences, Zaventem, Belgium) and 1 mg of WGA-SPA beads (wheatgerm agglutinin SPA beads from Amersham/Pharmacia, Freiburg, Germany) in a total volume of 250 µl. The incubation buffer used is 50 mmol/l of Tris-HCl supplemented with 0.06 wt. % bovine serum albumin. In order to determine non-specific binding, 100 µmol/l of naloxone is additionally added. When the ninety-minute incubation time has ended, the microtitre plates are centrifuged off for 20 minutes at 1000 g and the radioactivity is measured in a β-counter (Microbeta-Trilux, PerkinElmer Wallac, Freiburg, Germany). The percentage displacement of the radioactive ligand from its binding to the human µ-opiate receptor at a concentration of the test substances of 1 µmol/l is determined and stated as the percentage inhibition of specific binding. On the basis of the percentage displacement by different concentrations of the test substances, $IC_{50}$ inhibitory concentrations, which effect 50% displacement of the radioactive ligand, are calculated. $K_i$ values for the test substances are obtained by conversion by means of the Cheng-Prusoff equation.

Functional Study on the Human Bradykinin Receptor 1 (B1R)

The agonistic or antagonistic action of substances can be determined on the bradykinin receptor 1 (B1R) of the species human and rat using the following assay. According to this assay, the $Ca^{2+}$ influx through the channel is quantified with the aid of a $Ca^{2+}$-sensitive dye (Fluo-4 type, Molecular Probes Europe BV, Leiden, Netherlands) using a Fluorescent Imaging Plate Reader (FLIPR, Molecular Devices, Sunnyvale, USA).

Method:

Chinese hamster ovary cells (CHO K1 cells) which have been stably transfected with the human B1R gene (hB1R cells) or with the B1R gene of the rat (rB1R cells) are used. For functional studies, the cells are plated out on black 96-well plates having a clear base (BD Biosciences, Heidelberg, Germany or Greiner, Frickenhausen, Germany) in a density of 20,000-35,000 cells/well. The cells are incubated overnight at 37° C. and with 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany), with 10 vol. % FBS (fetal bovine serum, Gibco Invitrogen GmbH, Karlsruhe, Germany or PAN Biotech GmbH, Aidenbach, Germany).

On the following day, the cells are loaded for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed twice with HBSS buffer, and HBSS buffer additionally containing 0.1% BSA (bovine serum albumin; Sigma-Aldrich, Taufkirchen, Germany), 5.6 mM glucose and 0.05% gelatin (Merck KGaA, Darmstadt, Germany) is added to the plates. After incubation for a further 20 minutes at room temperature, the plates are inserted into the FLIPR for $Ca^{2+}$ measurement. Alternatively, washing is carried out with buffer A (15 mM HEPES, 80 mM NaCl, 5 mM KCl, 1.2 mM $CaCl_2$, 0.7 mM $MgSO_4$, 2 g/l glucose, 2.5 mM probenecid) followed by loading with buffer A with added 2.5 µM Fluo-4 and 0.025% Pluronic F127 (Sigma-Aldrich, Taufkirchen, Germany). The cells are then washed twice with buffer A and incubated for 30 minutes at room temperature with buffer A additionally containing 0.05% BSA and 0.05% gelatin and are then inserted into the FLIPR for $Ca^{2+}$ measurement.

The $Ca^{2+}$-dependent fluorescence is measured before and after the addition of substances ($\lambda_{ex}$=488 nm, $\lambda_{em}$=540 nm). Quantification is carried out by measuring the highest fluorescence intensity (FC, fluorescence counts) over time.

FLIPR Assay:

The FLIPR protocol consists of two substance additions. Test substances (10 µM) are first pipetted onto the cells and the $Ca^{2+}$ influx is compared with the control (hB1R: Lys-Des-Arg$^9$-bradykinin>=0.5 nM; rB1R: Des-Arg$^9$-bradykinin 10 µM). This gives the activation in %, based on the $Ca^{2+}$ signal after addition of Lys-Des-Arg$^9$-bradykinin (>=0.5 nM) or Des-Arg$^9$-bradykinin (10 µM).

After 10-20 minutes' incubation, Lys-Des-Arg$^9$-bradykinin (hB1R) or Des-Arg$^9$-bradykinin (rB1R) is applied in the concentration of the $EC_{80}$, and the influx of $Ca^{2+}$ is likewise determined.

Antagonists lead to suppression of the $Ca^{2+}$ influx. The % inhibition compared with the maximum achievable inhibition is calculated.

In order to determine the $IC_{50}$ value, the substances are added in various concentrations. Duplicate or triplicate determinations (n=2 or n=3) are carried out, and these are repeated in at least one further independent experiment (N>=2).

| Example | B1R antagonism, human [10 µM] % inhibition | B1R antagonism, rat [10 µM] % inhibition | µ-Opioid receptor [1 µM] % inhibition |
|---|---|---|---|
| 1 | 71.5 | 56 | 94 |
| 2 | 55.6 | 43 | 97 |
| 3 | 80.8 | 58 | 71 |
| 4 | 54.8 | 95 | 100 |
| 5 | 100.8 | 60 | 89 |
| 6 | 75.1 | 41 | 29 |
| 7 | 101.5 | 59 | 96 |
| 8 | 71.4 | 9 | 94 |

| Example | B1R antagonism, human [10 μM] % inhibition | B1R antagonism, rat [10 μM] % inhibition | μ-Opioid receptor [1 μM] % inhibition |
|---|---|---|---|
| 9 | 105 | 0 | |
| 10 | 70.1 | 0 | |
| 11 | 85.45 | 107 | |
| 12 | — | 0 | |
| 13 | 64.4 | 76 | |
| 14 | 86.9 | 75 | |
| 15 | 44.6 | 57 | |
| 16 | 35.5 | 57 | |
| 17 | 36.6 | 41 | |
| 18 | 58.8 | 73 | |
| 19 | 42.7 | 41 | |
| 20 | 38.8 | 28 | |
| 21 | 52.9 | 41 | |
| 22 | 70.3 | 34 | |
| 23 | 64 | 57 | |
| 24 | 82.2 | 67 | |
| 25 | 79.5 | 68 | |
| 26 | 97.4 | 73 | |
| 27 | 102.6 | 78 | |
| 28 | 26.3 | 34 | |
| 29 | 64.5 | 45 | |
| 30 | 75.7 | 58 | |
| 31 | 54. | 48 | |
| 32 | 10.7 | 15 | |
| 33 | 42.2 | 18 | |
| 34 | 71.2 | 41 | |
| 35 | 79.5 | 49 | |
| 36 | 64.1 | 67 | |
| 37 | 82.2 | 64 | |
| 38 | 17.9 | 15 | |
| 39 | 79.3 | 42 | |
| 40 | 17.1 | 20 | |
| 41 | 22. | 25 | |
| 42 | | 3 | |
| 43 | 28.9 | 11 | |
| 44 | 46.5 | 18 | |
| 45 | 75.7 | 26 | |
| 46 | — | −9 | |
| 47 | — | 12 | |
| 48 | — | 19 | |
| 49 | — | 19 | |
| 50 | — | 11 | |
| 51 | — | 1 | |
| 52 | — | −22 | |
| 53 | — | 12 | |
| 54 | 105 | 44 | 12 |
| 55 | 102.9 | 26 | 24 |
| 56 | 103.6 | 20 | 11 |
| 57 | 103.9 | 27 | 25 |
| 58 | 103.8 | 11 | 70 |
| 59 | 104.1 | 27 | 61 |
| 60 | 103.7 | 8 | 54 |
| 61 | 103.8 | 39 | 34 |
| 62 | — | 27 | 4 |
| 63 | 28.6 | −3 | 47 |
| 64 | 104.2 | 29 | 10 |
| 65 | 103.3 | 24 | 9 |
| 66 | 102.1 | 96 | 11 |
| 67 | 103.8 | 104 | 64 |
| 68 | 103.9 | 37 | 30 |
| 69 | 104.8 | 19 | 7 |
| 70 | 104 | 98 | 11 |
| 71 | 104.5 | 32 | 12 |
| 72 | 101.6 | 30 | 26 |
| 73 | 76.3 | 36 | 17 |
| 74 | 54.7 | 19 | 7 |
| 75 | 91.7 | 2 | 65 |
| 76 | 80.4 | 9 | 84 |
| 77 | 101.7 | 1 | 35 |
| 78 | 78.3 | 10 | 18 |
| 79 | 96.8 | 33 | 47 |
| 80 | 16.7 | 15 | 7 |
| 81 | 65.3 | 56 | 16 |
| 82 | 23.5 | 7 | 23 |
| 83 | 37 | −3 | 22 |
| 84 | 95.4 | 19 | 90 |
| 85 | 92.7 | 22 | 95 |
| 86 | 100.7 | 30 | 54 |
| 87 | 96.8 | 25 | 38 |
| 88 | 101 | 61 | 58 |
| 89 | 16.4 | 26 | 8.5 |
| 90 | 14.4 | 17 | 12 |
| 91 | 17.8 | 8 | |
| 92 | 26 | −13 | |
| 93 | 15.5 | −24 | |
| 94 | — | −19 | |
| 95 | 18.6 | −15 | |
| 96 | — | 12 | |
| 97 | 16 | 11 | |
| 98 | 66.8 | −8 | |
| 99 | 83.3 | −7 | |
| 100 | — | −2 | |
| 101 | 103.6 | 31 | 4 |
| 102 | 104.3 | 12 | 35 |
| 103 | 103.4 | 37 | 71 |
| 104 | 32.8 | 13 | 11 |
| 105 | 99.5 | 24 | 76 |
| 106 | 48.3 | 19 | 21 |
| 107 | 102.3 | 26 | 78 |
| 108 | 97 | 78 | 6 |
| 109 | 102 | 99 | 5 |
| 110 | 102 | 100 | 3 |
| 111 | 94 | 61 | −2 |
| 112 | 90 | 61 | 28 |
| 113 | 97 | 39 | 21 |
| 114 | 93 | 71 | 40 |
| 115 | 87 | 52 | 11 |
| 116 | 102 | 93 | 7 |
| 117 | — | | 47 |
| 118 | 101 | 93 | 3 |
| 119 | 102 | 97 | 52 |
| 120 | 105 | 73 | 41 |
| 121 | 105 | 58 | 6 |
| 122 | 98 | 40 | 47 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted sulfonamide compound corresponding to formula I:

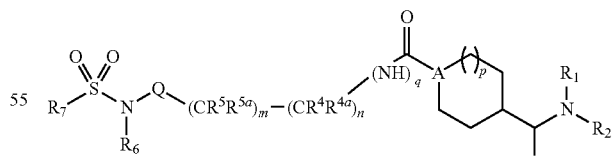

wherein
m represents 0, 1 or 2,
n represents 0, 1 or 2,
p represents 1,
q represents 0 or 1,
A represents CH—NH—, CH—CH$_2$—NH— or CH—CH$_2$—CH$_2$—NH, wherein individual hydrogen atoms can also be replaced by C$_{1-5}$-alkyl, $R^1$ and $R^2$ each independently denote H; $C_{1-6}$-alkyl; or phenyl linked via a $C_{1-3}$-alkyl chain, with the proviso that $R^1$ and $R^2$ are not both H;

$R^3$ represents aryl or heteroaryl, in each case unsubstituted or mono- or poly-substituted; or aryl linked via a $C_{1-3}$-alkyl chain and in each case unsubstituted or mono- or poly-substituted;

$R^4$ and $R^{4a}$ each independently represent H, $C_{1-6}$-alkyl, in each case saturated or unsaturated, branched or unbranched, unsubstituted or mono- or poly-substituted; F; Cl; aryl, in each case unsubstituted or mono- or poly-substituted; or aryl linked via a $C_{1-3}$-alkyl chain and in each case unsubstituted or mono- or poly-substituted;

$R^5$ and $R^{5a}$ each independently represent H; or $C_{1-6}$-alkyl, in each case saturated or unsaturated, branched or unbranched, unsubstituted or mono- or poly-substituted; OH, $OC_{1-6}$-alkyl, F, Cl, phenoxy or benzyloxy;

Q denotes a single bond, —$CH_2$— or —$CH_2$—$CH_2$—;

$R^6$ represents H; $C_{1-6}$-alkyl, in each case saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; aryl or $C_{3-8}$-cycloalkyl linked via a $C_{1-3}$-alkyl chain; or $R^6$ together with Q and including the adjacent nitrogen represents

[structures]

$R^7$ represents aryl or heteroaryl, in each case unsubstituted or mono- or poly-substituted;

wherein substituents of mono- or poly-substituted alkyl or cycloalkyl groups are selected from the group consisting of F, Cl, Br, I, CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl and benzyl; and wherein substituents of mono- or poly-substituted aryl or heteroaryl groups are selected from the group consisting of F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, —O—$C_{1-6}$-alkyl-OH, C(=O)$C_{1-6}$-alkyl, $CO_2H$, $CH_2SO_2$-phenyl, $CO_2$—$C_{1-6}$-alkyl, $OCF_3$, $CF_3$,

[structures]

$C_{1-6}$-alkyl, phenyl, pyridyl, thienyl and furyl;

or a salt thereof with a physiologically acceptable acid.

2. A substituted sulfonamide compound according to claim 1, wherein said compound is present in the form of an isolated stereoisomer.

3. A substituted sulfonamide compound according to claim 1, wherein said compound is present in the form of a mixture of stereoisomers.

4. A substituted sulfonamide compound according to claim 1, wherein said compound is present in the form of a racemic mixture.

5. A substituted sulfonamide compound according to claim 1, wherein $R^1$ and $R^2$ each independently denote H; $CH_3$; $C_2H_5$; or phenyl linked via a $C_{1-3}$-alkyl chain, with the provisio that $R^1$ and $R^2$ are not both H.

6. A substituted sulfonamide compound according to claim 1, wherein $R^3$ represents 2-thienyl, 4-fluorophenyl, 3-fluorophenyl, 4-chlorophenyl, phenethyl, phenyl or benzyl.

7. A substituted sulfonamide compound according to claim 1, wherein $R^4$ and $R^{4a}$ each represent H.

8. A substituted sulfonamide compound according to claim 1, wherein $R^5$ and $R^{5a}$ each represent H.

9. A substituted sulfonamide compound according to claim 1, wherein $R^6$ represents methyl, ethyl or benzyl and Q represents a single bond.

10. A substituted sulfonamide compound according to claim 9, wherein $R^6$ denotes methyl.

11. A substituted sulfonamide compound according to claim 1, wherein the group

[structure]

of formula I represents

[structures]

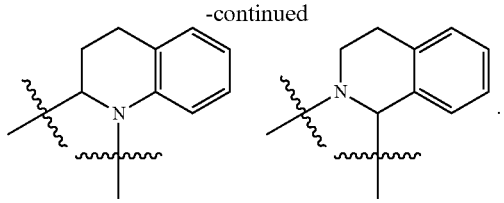

12. A substituted sulfonamide compound according to claim 1, wherein the group

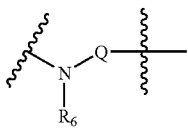

of formula I represents

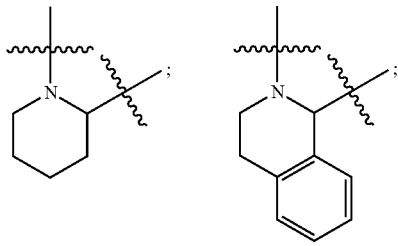

m represents 0, 1 or 2;
n represents 0;
q represents 0; and
$R^5$ and $R^5a$ each represent H;
or
Q represents a single bond;
m represents 0, 1 or 2;
n represents 1 or 2;
q represents 0;
$R^4$ and $R^{4a}$ each represent H;
$R^5$ and $R^{5a}$ each represent H; and
$R^6$ represents H or $C_{1-6}$-alkyl.

13. A substituted sulfonamide compound according to claim 1, wherein

A represents NH—CH, NH—$CH_2$—CH or NH—$CH_2$—$CH_2$—CH, wherein individual hydrogen atoms can also be replaced by $C_{1-5}$-alkyl;
$R^1$ and $R^2$ each independently represent $C_{1-6}$-alkyl and
$R^3$ represents aryl, which optionally may be linked via a $C_{1-3}$-alkyl group, wherein the aryl is in each case unsubstituted or mono- or poly-substituted by identical or different substituents independently selected from the group consisting of methyl, ethyl, methoxy, ethoxy, F, Cl, Br, CN, $CF_3$, $OCF_3$ and OH.

14. A compound according to claim 13, wherein $R^1$ and $R^2$ each independently represent methyl, ethyl, n-propyl, isopropyl, n-butyl, sec-butyl, isobutyl or tert-butyl, and
$R^3$ represents phenyl or furanyl.

15. A substituted sulfonamide compound according to claim 1, wherein the group

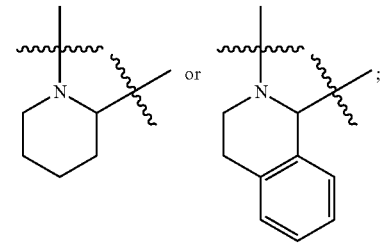

in formula I represents m represents 1 or 2;
n and q each represent 0;
$R^5$ and $R^{5a}$ each represent H;
A represents NH—CH or NH—$CH_2$—CH;
$R^1$ and $R^2$ each independently represent $C_{1-6}$-alkyl; and
$R_3$ represents phenyl, wherein the phenyl is in each case unsubstituted or mono- or poly-substituted by identical or different substituents independently selected from the group consisting of methyl, ethyl, methoxy, ethoxy, F, Cl, Br, CN, $CF_3$, $OCF_3$ and OH,

16. A substituted sulfonamide compound according to claim 15, wherein:

m represents 1;
A represents NH—CH;
$R^1$ and $R^2$ each independently represent methyl, ethyl, n-propyl, isopropyl, n-butyl, sec-butyl, isobutyl or tert-butyl; or
the phenyl group in $R_3$ is mono- or polysubstituted by substituents independently selected from the group consisting of methyl, methoxy, F, Cl, Br, CN, $CF_3$ and OH.

17. A substituted sulfonamide compound according to claim 1, wherein $R^7$ represents 2,4-dichlorophenyl, 2,4,6-trichlorophenyl, 4-methoxyphenyl, 3-trifluoromethylphenyl, 2,6-dimethyl-4-methoxyphenyl or 3,4-dichlorophenyl.

18. A substituted sulfonamide compound according to claim 1, wherein said compound is selected from the group consisting of:

(1) N-(3-{3-[4-(dimethylaminophenylmethyl)cyclohexyl]ureido}propyl)-4-methoxy-2,3,6,N-tetramethylbenzenesulfonamide;

(5) 5-[methyl-(2,4,6-trichloro-benzenesulfonyl)-amino]-pentanecarboxylic acid [4-(dimethylamino-phenyl-methyl)-cyclohexyl]-amide;

(7) 5-[methyl-(2,4,6-trichloro-benzenesulfonyl)-amino]-pentanecarboxylic acid [4-(dimethylamino-phenyl-methyl)-cyclohexylmethyl]-amide;

(8) N-[4-(dimethylamino-phenyl-methyl)-cyclohexylmethyl]-2-[1-(3-trifluoro-methyl-benzenesulfonyl)-piperidin-2-yl]-acetamide;

(9) N-[4-(dimethylamino-phenyl-methyl)-cyclohexyl]-2-[2-(4-methoxy-benzene-sulfonyl)-1, 2, 3,4-tetrahydro-isoquinolin-1-yl]-acetamide;

(10) 2-[2-(3,4-dichloro-benzenesulfonyl)-1,2,3,4-tetrahydro-isoquinolin-1-yl]-N-[4-(dimethylamino-phenyl-methyl)-cyclohexyl]-acetamide;

(13) N-{4-[dimethylamino-(3-fluoro-phenyl)-methyl]-cyclohexyl}-2-[2-(4-methoxy-benzenesulfonyl)-1,2,3,4-tetrahydro-isoquinolin-1-yl]-acetamide;
(14) N-{4-[dimethylamino-(4-fluoro-phenyl)-methyl]-cyclohexyl}-2-[2-(4-methoxy-benzenesulfonyl)-1,2,3,4-tetrahydro-isoquinolin-l-yl]-acetamide;
(15) N-[4-(dimethylamino-thiophen-2-yl-methyl)-cyclohexyl]-2-[2-(4-methoxy-benzenesulfonyl)-1,2,3,4-tetrahydro-isoquinolin-1-yl]-acetamide;
(16) N-{4-[dimethylamino-(3-fluoro-phenyl)-methyl]-cyclohexylmethyl}-2-[2-(4-methoxy-benzenesulfonyl)-1,2,3,4-tetrahydro-isoquinolin-1-yl]-acetamide;
(17) N-[4-(dimethylamino-phenyl-methyl)-cyclohexylmethyl]-2-[2-(4-methoxy-benzenesulfonyl)-1,2,3,4-tetrahydro-isoquinolin-l-yl]-acetamide;
(18) N-[4-(1-dimethylamino-3-phenyl-propyl)-cyclohexylmethyl]-2-[2-(4-methoxy-benzenesulfonyl)-1,2,3,4-tetrahydro-isoquinolin-1-yl]-acetamide;
(19) N-{4-[dimethylamino-(4-fluoro-phenyl)-methyl]-cyclohexylmethyl}-2-[2-(4-methoxy-benzenesulfonyl)-1,2,3,4-tetrahydro-isoquinolin-1-yl]-acetamide;
(20) N-{4-[(4-chloro-phenyl)-dimethylamino-methyl]-cyclohexylmethyl}-2-[2-(4-methoxy-benzenesulfonyl)-1,2,3,4-tetrahydro-isoquinolin-1-yl]-acetamide;
(21) N-[4-(dimethylamino-thiophen-2-yl-methyl)-cyclohexylmethyl]-2-[2-(4-methoxy-benzenesulfonyl)-1,2,3,4-tetrahydro-isoquinolin-1-yl]-acetamide;
(22) N-(2-{4-[(4-chloro-phenyl)-dimethylamino-methyl]-cyclohexyl}-ethyl)-2-[2-(4-methoxy-benzenesulfonyl)-1,2,3,4-tetrahydro-isoquinolin-1-yl]-acetamide;
(23) N-(2-{4-[dimethylamino-(3-fluoro-phenyl)-methyl]-cyclohexyl}-ethyl)-2-[2-(4-methoxy-benzenesulfonyl)-1,2,3,4-tetrahydro-isoquinolin-1-yl]-acetamide;
(24) N-(2-{4-[dimethylamino-(4-fluoro-phenyl)-methyl]-cyclohexyl}-ethyl)-2-[2-(4-methoxy-benzenesulfonyl)-1,2,3,4-tetrahydro-isoquinolin-l-yl]-acetamide;
(25) N-{2-[4-(dimethylamino-thiophen-2-yl-methyl)-cyclohexyl]-ethyl}-2-[2-(4-methoxy-benzenesulfonyl)-1,2,3,4-tetrahydro-isoquinolin-1-yl]-acetamide;
(26) 2-(2-(3,4-dichlorophenylsulfonyl)-1,2,3,4-tetrahydroisoquinolin-1 -yl)-N-(4-((dimethylamino) (3-fluorophenyl)methyl)cyclohexyl)acetamide;
(27) 2-(2-(3,4-dichlorophenylsulfonyl)-1,2,3,4-tetrahydroisoquinolin- 1-yl)-N-(4-((dimethylamino) (4-fluorophenyl)methyl)cyclohexyl)acetamide;
(28) 2-[2-(3,4-dichloro-benzenesulfonyl)-1,2,3,4-tetrahydro-isoquinolin-1-yl]-N-{4-[ dimethylamino-(3-fluorophenyl)-methyl]-cyclohexylmethyl}-acetamide;
(29) 2-[2-(3,4-dichloro-benzenesulfonyl)-1,2,3,4-tetrahydro-isoquinolin-1-yl]-N-[4-(dimethylamino-phenyl-methyl)-cyclohexylmethyl]-acetamide;
(30) 2-[2-(3,4-dichloro-benzenesulfonyl)-1,2,3,4-tetrahydro-isoquinolin- 1-yl] -N- [4-(1-dimethylamino- 3-phenyl-propyl)-cyclohexylmethyl]-acetamide;
(31) 2-[2-(3,4-dichloro-benzenesulfonyl)- 1,2,3,4-tetrahydro-isoquinolin-1-yl]-N-{4-[dimethylamino-(4-fluorophenyl)-methyl]-cyclohexylmethyl}-acetamide;
(32) N-{4-[(4-chloro-phenyl)-dimethylamino-methyl]-cyclohexylmethyl}1-2-[2-(3,4-dichloro-benzenesulfonyl)-1,2,3,4-tetrahydro-isoquinolin-l-yl]-acetamide;
(33) N-(2-{4-[(4-chloro-phenyl)-dimethylamino-methyl]-cyclohexyl}-ethyl)-2-[2-(3,4-dichloro-benzene sulfonyl)-1,2,3,4-tetrahydro-isoquinolin- 1-yl]-acetamide;
(34) 2-[2-(3,4-dichloro-benzenesulfonyl)-1,2,3,4-tetrahydro-isoquinolin- 1-yl]-N-(2-{4-[dimethylamino-(3-fluoro-phenyl)-methyl]-cyclohexyl}-ethyl)-acetamide;
(35) 2-[2-(3,4-dichloro-benzenesulfonyl)-1,2,3,4-tetrahydro-isoquinolin-1-yl]-N-(2-{4-[dimethylamino-(4-fluoro-phenyl)-methyl]-cyclohexyl}-ethyl)-acetamide;
and salts thereof with a physiologically acceptable acid.

19. A pharmaceutical composition comprising a substituted sulfonamide compound according to claim 1, and at least one pharmaceutically acceptable carrier or auxiliary substance.

20. A process for preparing a substituted sulfonamide compound according to claim 1 corresponding to formula Ia, wherein q represents 0 and $R^1$ through $R^8$, $R^H$, $R^J$, A, Z, Q, m, n and p have the respective meanings given in claim 1,
said process comprising reacting a carboxylic acid corresponding to formula III with a primary or secondary amine corresponding to formula II

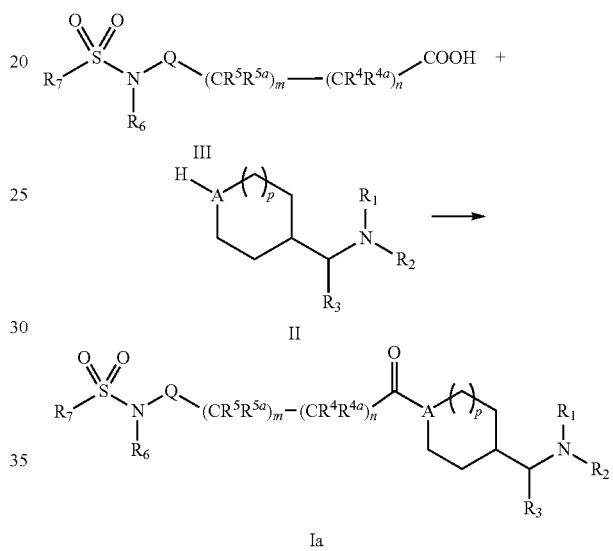

in the presence of a water-removing agent, and optionally in the presence of HOAt or HOBt and of an organic base, in an organic solvent.

21. A process according to claim 20, wherein:
the water removing agent is slected from the group consisting of sodium sulfate, magnesium sulfate, phosphorus oxide, CDI, DCC optionally bonded to a polymer, TBTU, EDCI, PyBOP and PFPTFA;
the organic base is DIPEA or pyridine, or
the organic solvent is selected from the group consisting of THF, dichloromethane, diethyl ether, dioxane, DMF or acetonitrile.

22. A method of treating or inhibiting pain in a subject, said method comprising administering to said subject a pharmaceutically effective amount of a substituted sulfonamide compound according to claim 1.

23. A method according to claim 22, wherein said pain is selected from the group consisting of acute pain, visceral pain, neuropathic pain, chronic pain and inflammatory pain.

24. A method of treating chronic inflammations in a subject, said method comprising administering to said subject a pharmaceutically effective amount of a substituted sulfonamide compound according to claim 1.

* * * * *